US010139405B2

(12) United States Patent
Deirmengian et al.

(10) Patent No.: US 10,139,405 B2
(45) Date of Patent: Nov. 27, 2018

(54) SYSTEM FOR DETECTING INFECTION IN SYNOVIAL FLUID

(71) Applicant: CD DIAGNOSTICS, INC., Claymont, DE (US)

(72) Inventors: Carl Deirmengian, Newtown Square, PA (US); Richard C. Birkmeyer, Landenberg, PA (US); Keith Kardos, Bethlehem, PA (US); Patrick Kilmartin, Rochester, NY (US); Alexander Cameron, Cherry Hill, NJ (US); Kevin Schiller, Phoenixville, PA (US); Eun Kyung Chung, Avondale, PA (US)

(73) Assignee: CD Diagnostics, Inc., Claymont, DE (US)

( * ) Notice: Subject to any disclaimer, the term of this patent is extended or adjusted under 35 U.S.C. 154(b) by 0 days.

(21) Appl. No.: 14/371,965

(22) PCT Filed: Oct. 22, 2012

(86) PCT No.: PCT/US2012/061350
§ 371 (c)(1),
(2) Date: Jul. 11, 2014

(87) PCT Pub. No.: WO2013/112216
PCT Pub. Date: Aug. 1, 2013

(65) Prior Publication Data
US 2015/0011412 A1 Jan. 8, 2015

Related U.S. Application Data

(60) Provisional application No. 61/590,234, filed on Jan. 24, 2012.

(51) Int. Cl.
*G01N 33/558* (2006.01)
*G01N 33/68* (2006.01)

(52) U.S. Cl.
CPC ....... *G01N 33/558* (2013.01); *G01N 33/6869* (2013.01); *G01N 33/6893* (2013.01); *G01N 2333/535* (2013.01); *G01N 2333/545* (2013.01); *G01N 2333/5412* (2013.01); *G01N 2333/5421* (2013.01); *G01N 2333/5428* (2013.01); *G01N 2800/10* (2013.01); *G01N 2800/26* (2013.01); *G01N 2800/60* (2013.01); *G01N 2800/7095* (2013.01)

(58) Field of Classification Search
CPC ............. G01N 33/558; G01N 33/6893; G01N 2333/535; G01N 2333/5412; G01N 2333/5421; G01N 2333/5428; G01N 2333/545; G01N 2800/10; G01N 2800/26; G01N 2800/60; G01N 2800/7095

See application file for complete search history.

(56) References Cited

U.S. PATENT DOCUMENTS

| | | | |
|---|---|---|---|
| 4,366,241 A | 12/1982 | Tom et al. | |
| 4,376,110 A | 3/1983 | David et al. | |
| 4,517,288 A | 5/1985 | Geigel et al. | |
| 4,837,168 A | 6/1989 | De Jaeger et al. | |
| 5,143,854 A | 9/1992 | Pirrung et al. | |
| 5,550,061 A * | 8/1996 | Stone | G01N 33/84 422/412 |
| 5,800,992 A | 9/1998 | Fodor et al. | |
| 5,837,832 A | 11/1998 | Chee et al. | |
| 5,948,692 A | 9/1999 | Miyauti et al. | |
| 5,953,727 A | 9/1999 | Akerblom et al. | |
| 5,972,594 A * | 10/1999 | Heine | G01N 33/68 435/4 |
| 6,248,598 B1 * | 6/2001 | Bogema | B01L 3/5023 422/412 |
| 6,365,352 B1 | 4/2002 | Yerramilli | |
| 6,433,012 B1 | 8/2002 | Tuse et al. | |
| 6,654,120 B2 | 11/2003 | Ban | |
| 6,716,641 B1 * | 4/2004 | Sundrehagen | G01N 33/558 435/287.1 |
| 7,344,893 B2 | 3/2008 | Kirkegaard et al. | |
| 7,598,080 B2 | 10/2009 | Deirmengian | |
| 2003/0077611 A1 | 4/2003 | Slepnev | |

(Continued)

FOREIGN PATENT DOCUMENTS

| EP | 0249418 A2 * | 12/1987 | ............. G01N 33/53 |
|---|---|---|---|
| EP | 1310567 | 5/2003 | |

(Continued)

OTHER PUBLICATIONS

Martins, Development of Internal Controls for the luminex instrument as part of a multiplex seven-analyte viral respiratory antibody profile, Clinical and Diagnostic laboratory Immunolog 2002, 9(1), 41-45.*
Varoga et al., The antimicrobial peptide HBD-2 and the Toll-like receptors-2 and -4 are induced in synovial membranes in case of septic arthritis, Virchows Arch (2009) 454:685-694.*
Greenbaum et al., Comparing protein abundance and mRNA expression levels on a genomic scale, Genome Biology 2003, 4:117.1-8.*
Paulsen et al., Detection of Antimicrobial peptides in human osteoarthritic cartilage and synovial membrane, Poster Session—Osteoarthritis—Hall E 47th Annual Meeting, Orthopaedic Research Society, Feb. 25-28, 2001, San Francisco, California, 0652.*

(Continued)

*Primary Examiner* — Andrea S Grossman
(74) *Attorney, Agent, or Firm* — Schwegman Lundberg & Woessner, P.A.

(57) ABSTRACT

The invention provides methods and systems for detecting a biomarker in a synovial fluid wherein the system also includes a control to ensure that the test sample is indeed synovial fluid. The biomarkers and the control for synovial fluid can be identified using proteomic methods, including but not limited to antibody based methods, such as an enzyme-linked immunosorbant assay (ELISA), a radioimmunoassay (RIA), or a lateral flow immunoassay.

14 Claims, 19 Drawing Sheets

(56) References Cited

U.S. PATENT DOCUMENTS

| | | | |
|---|---|---|---|
| 2003/0082512 A1 | 5/2003 | Yerramilli et al. | |
| 2004/0175769 A1* | 9/2004 | Hara | G01N 33/5308 435/7.9 |
| 2005/0037344 A1 | 2/2005 | Stuhlmuller et al. | |
| 2005/0250141 A1* | 11/2005 | Lambert | B82Y 5/00 435/6.11 |
| 2005/0287517 A1 | 12/2005 | Deppisch et al. | |
| 2006/0084096 A1 | 4/2006 | Boess et al. | |
| 2006/0294604 A1 | 12/2006 | Fridman et al. | |
| 2008/0317808 A1* | 12/2008 | Hollander | A61L 27/20 424/423 |
| 2009/0227692 A1* | 9/2009 | Li | G01N 33/57415 514/789 |
| 2009/0318301 A1* | 12/2009 | Deirmengian | 506/7 |
| 2010/0061983 A1 | 3/2010 | Loetscher et al. | |
| 2010/0324146 A1 | 12/2010 | Fairley | |
| 2012/0010096 A1 | 1/2012 | Wohlgemuth et al. | |
| 2012/0264645 A1 | 10/2012 | Lillard, Jr. | |

FOREIGN PATENT DOCUMENTS

| | | | |
|---|---|---|---|
| WO | 1993009668 | | 5/1993 |
| WO | 1999032660 | | 7/1999 |
| WO | 2010036930 | A1 | 4/2010 |
| WO | WO 2010036930 | A1 * 4/2010 | ....... G01N 33/56911 |
| WO | WO-2013112216 | A1 | 8/2013 |

OTHER PUBLICATIONS

Bast et al., Translational Crossroads for Biomarkers, Clin Cancer Res 2005; 11(17), 6103-6108.*
LaBaer et al., So you want to look for biomarkers, Journal of Proteome Research 2005; 4, 1053-1059.*
Baker, In Biomarkers We Trust, Nature Biotechnology 2005; 23(3) 297-304.*
Bohunicky, B. et al., "Biosensors: The New Wave in Cancer Diagnosis," Nanotechnology Science and Applications, vol. 4, No. 1, pp. 1-10, 2011.
Deirmengian, C. et al., "Synovial Fluid Biomarkers for Periprosthetic Infection," Clin. Orthop. Relat. Res., vol. 468, pp. 2017-2023, 2010.
International Search Report dated Mar. 12, 2013, for PCT International Application No. PCT/US2012/061350.
Altschul et al., "Issues in Searching Molecular Sequence Databases," Nature Genet., vol. 6, pp. 119-129, 1994.
Altschul, "A Protein Alignment Scoring System Sensitive at all Evolutionary Distances," J. Mol. Evol., vol. 36, pp. 290-300, 1993.
Golub et al., "Molecular Classification of Cancer: Class Discovery and Class Prediction by Gene Expression Monitoring," Science, vol. 286(5439), pp. 531-537, 1999.
Henikoff et al., "Amino Acid Substitute Matrices from Protein Blocks," Proc. Natl. Acad. Sci. USA, vol. 89, pp. 10915-10919, 1992.
Huse et al., "Generation of Large Combination Library of the Immunoglobulin Repertoire in Phage Lambda," Science, vol. 246, pp. 1275-1281, 1989.
Jungblut et al., "Protein Identification from 2-DE gels by MALDI Mass Spectrometry," Mass Spectr. Rev., vol. 16, pp. 145-162, 1997.
Karlin et al., "Methods for Assessing the Statistical Significance of Molecular Sequence Features by Using General Scoring Schemes," Proc. Natl. Acad. Sci. USA, vol. 87, pp. 2264-2268, 1990.
Kohler et al., "Continuous Cultures of Fused Cells Secretingt Antibody of Predefined Specificity," Nature, vol. 256, pp. 495-497, 1975.
Lockhart et al., "Expression Monitoring by Hybridization to High-Density Oligonucleotide Arrays," Nat. Biotechnol., vol. 14, pp. 1675-1680, 1996.
McGall et al., "Light-directed Synthesis of High-density Oligonucleotide Arrays Using Semiconductor Photoresists," Proc. Nat. Acad. Sci USA, vol. 93, pp. 13555-13560, 1996.

Ward et al., "Binding Activities of a Repertoire of Single Immunoglobulin Variable Domains Secreted from *Escherichia coli*," Nature, vol. 341, pp. 544-546, 1989.
Barnes, M.G. et al., "Gene Expression in Juvenile Arthritis and Spondyloarthropathy: Pro-angiogenic ELR+ Chemokine Genes Relate to Course of Arthritis," Rheumatology, vol. 43, No. 8, pp. 973-979, 2004.
Deirmengian, C. et al, "The Mark Coventry Award: White Blood Cell Gene Expression: A New Approach Toward the Study and Diagnosis of Infection," Clin. Orthop. Relat. Res., vol. 440, pp. 38-44, 2005.
Friese, M.A. et al., "Release of Endogenous Anti-Inflammatory Complement Regulators FHL-1 and Factor H Protects Synovial Fibroblasts during Rheumatoid Arthritis," Clin. Exp. Immunol., vol. 132, No. 3, pp. 485-495, 2003.
Heller, R.A. et al., "Discovery and Analysis of Inflammatory Disease-related Genes Using cDNA Microarrays," Proc. Natl. Acad. Sci. USA, vol. 94, No. 6, pp. 2150-2155, 1997.
O'Hara, R. et al., "Local Expression of the Serum Amyloid A and Formyl Peptide Receptor-like 1 Genes in Synovial Tissue is Associated with Matrix Metalloproteinase Production in Patients with Inflammatory Arthritis," Arthritis Rheum., vol. 50, No. 6, pp. 1788-1799, 2004.
Pufe, T. et al., "Expression of Pleiotrophin, an Embryonic Growth and Differentiation Factor, in Rheumatoid Arthritis," Arthritis Rheum., vol. 48, No. 3, pp. 660-667, 2003.
Stuhlmuller, B. et al., "Identification of Known and Novel Genes in Activated Monocytes from Patients with Rheumatoid Arthritis," Arthritis Rheum., vol. 43, No. 4, pp. 775-790, 2000.
Yerramilli, S. et al., "RNA Expression Patterns Change Dramatically in Human Neutrophils Exposed to Bacteria," Blood, vol. 97, No. 8, pp. 2457-2468, 2001.
Zanders, E.D. et al., "Analysis of Immune System Gene Expression in Small Rheumatoid Arthritis Biopsies Using a Combination of Subtractive Hybridization and High-Density cDNA Arrays," J. Immunol. Methods, vol. 233, No. 1-2, pp. 131-140, 2000.
"Gene Characterization Kits," Stratagene Catalog, p. 39, 1988.
Yum et al., "Involvement of Phosphoinositide 3-Kinases in Neutrophil Activation and the Development of Acute Lung Injury," J. Immunology, vol. 161, pp. 6601-6608, 2001.
Buck, C. et al., "Interleukin-6: A Sensitive Parameter for the Early Diagnosis of Neonatal Bacterial Infection," Pediatrics, vol. 93(1), pp. 54-58, 1994.
Hii, C.S.T. et al., "Regulation of Human Neutrophil-mediated Cartilage Proteoglycan Degradation by Phosphatidylinositol-3-kinase," Immunology, vol. 102(1), pp. 59-66, 2001.
Harada, A. et al., "Essential involvement of interleuikin-8 (IL-8) in acute inflammation," Journal of Leukocyte Biology, vol. 56, pp. 559-564, 1994.
"Application Serial No. 2012367247, Voluntary Amendment filed Sep. 15, 2014", 14 pgs.
"European Application Serial No. 12866897.7, Extended European Search Report dated Dec. 7, 2015", 10 pgs.
"European Application Serial No. 12866897.7, Partial European Search Report dated Aug. 14, 2015", 7 pgs.
"European Application Serial No. 12866897.7, Response filed Jul. 11, 2016 to Extended European Search Report dated Dec. 7, 2015", 7 pgs.
"International Application Serial No. PCT/US2012/061350, International Preliminary Report on Patentability dated Aug. 7, 2014", 8 pgs.
"International Application Serial No. PCT/US2012/061350, Invitation to Pay Additional Fees dated Jan. 9, 2013", 2 pgs.
Jacovides, Christina L., et al., "Molecular Markers for Diagnosis of Periprosthetic Joint Infection", The Journal of Arthroplasty, Churchill Livingstone, Amsterdam, NL, vol. 26, No. 6, XP028280934, ISSN: 0883-5403, DOI: 10.1016/J.ARTH.2011.03.025, (Mar. 11, 2011), 99-103.
Paulsen, Friedrich, et al., "Antimicrobial peptides are expressed and produced in healthy and inflamed human synovial membranes", Journal of Pathology, John Wiley & Sons Ltd, GB, vol . 198, No. 3, XP008115110, ISSN: 0022-3417, (Jan. 1, 2002), 369-377.

(56) References Cited

OTHER PUBLICATIONS

"European Application Serial No. 12866897.7, Communication Pursuant to Article 94(3) EPC dated Aug. 10, 2017", 4 pgs.
"European Application Serial No. 12866897.7, Response filed May 17, 2017 to Action dated Feb. 17, 2017", 29 pgs.
Birgit, Riepl, et al., "Tumor necrosis factor and norepinephrine lower the levels of human neutrophil peptides 1-3 secretion by mixed synovial tissue cultures in osteoarthritis and rheumatoid arthritis", Arthritis Research and Therapy, Biomed Central, val. 12, No. 3 R110, (Jun. 4, 2010), 9 pgs.
Bokarewa, M I, et al., "Intraarticular release and accumulation of defensins and bactericidal/permeability-increasing protein in patients with rheumatoid arthritis", Journal of Rheumatology, vol. 30, No. 8; XP055396032, (Aug. 1, 2003), 1719-1724.
"Australian Application Serial No. 2012367247, First Examiners Report dated Oct. 3, 2017", 5 pgs.
"Australian Application Serial No. 2012367247, Response filed Feb. 23, 2018 to Subsequent Examiners Report dated Dec. 21, 2017", 9 pgs.
"Australian Application Serial No. 2012367247, Response filed Dec. 6, 2017 to First Examiners Report dated Oct. 3, 2017", 9 pgs.
"Australian Application Serial No. 2012367247, Subsequent Examiners Report dated Dec. 21, 2017", 4 pgs.
"European Application Serial No. 12866897.7, Response filed Dec. 8, 2017 to Communication Pursuant to Article 94(3) EPC dated Aug. 10, 2017", 11 pgs.
Akobeng, Anthony K., "Understanding diagnostic tests 3: receiver operating characteristic curves", Acta Pæiatrica ISSN 0803-5253; 96, (2007), pp. 644-647.

\* cited by examiner

SYSTEM FOR DETECTING INFECTION IN SYNOVIAL FLUID

CROSS-REFERENCE TO RELATED APPLICATION

The present application is a 35 U.S.C § 371 national phase application of, and claims priority to, PCT Application No. PCT/US2012/061350, filed Oct. 22, 2012, which claims priority under 35 U.S.C. § 119(e) to U.S. Provisional Application No. 61/590,234, filed Jan. 24, 2012, all of which application are incorporated herein by reference in their entireties.

BACKGROUND OF THE INVENTION

Age, arthritis, total joint replacement, diabetes, skin infection and surgery are some of the predisposing risk factors to joint infection, also known as septic arthritis. While fungus and viruses can be contributors, the most critical source of joint infections is bacterial pathogens due to their rapid growth and destruction of joints. Joint infection, if not properly diagnosed and treated, can be catastrophic to the joint and in some cases lead to sepsis and death.

Total joint replacements present a particular challenge. The number of total joint replacements in the US is growing dramatically. The baby boomer population is rapidly progressing beyond the age of 50. The need for total joint replacement is increasing as this population remains active and is demanding treatments that will allow them to maintain their active lifestyles.

Joint pain is frequently misdiagnosed and is a significant contributor to rising medical costs. The most common causes of joint pain are crystals (gout, pseudogout), injury, infection, and rheumatoid arthritis. Currently, few tests are available to accurately diagnose the cause of joint pain. In many cases, a blood test is performed, which frequently yields vague and ambiguous results (sensitivity less than 80% and specificity less than 70%). Testing the joint fluid at the site of the pain is much more accurate because one is evaluating a specific response versus a general response.

Diagnostic information obtained via joint fluid analysis has been generally considered to be vital in an accurate diagnosis. However, there is no consensus as to which tests are most useful and which should be included in routine analysis. Joint infection is a particularly difficult problem to diagnose with current technology. Joint infection can be catastrophic to the health of the joint and can ultimately lead to sepsis that migrates to the rest of the body.

Thus, there is an urgent need in the art for compositions and methods for properly diagnosing joint pain. The present invention addresses this need.

SUMMARY OF THE INVENTION

The present invention provides a system for diagnosing joint infection in a subject, wherein the system detects the presence or absence of a biomarker for joint infection in synovial fluid obtained from the subject, wherein detection of the presence or absence of the biomarker diagnoses joint infection in the subject with at least 90% accuracy.

In one embodiment, the system comprises: a) a first region comprising a first detection reagent that detects the presence of the biomarker for joint infection in synovial fluid, wherein the first detector reagent specifically binds the biomarker, b) a second region comprising an internal control detector reagent for verification of synovial fluid, wherein the internal control detector reagent specifically binds a marker of synovial fluid; wherein joint infection is diagnosed when the biomarker and the marker of synovial fluid are detected.

In one embodiment, the joint infection is diagnosed when the marker for synovial fluid is detected at a higher intensity than the biomarker.

In one embodiment, the biomarker is selected from the group consisting of HNP1-3, ELA-2, BPI, NGAL, Resistin, Thrombospondin, Lactoferrin, IL-1β, IL-8, CRP, TNFα, IL-6, FINE, a2M, VEGF, FGF2, SKALP, IP-10, LMP, Orsomucoid, and any combination thereof.

In one embodiment, the marker of synovial fluid is selected from the group consisting of hyaluronic acid (HA), mucopolysaccharide, glucosamine, chondroitin sulfate cartilage oligomeric matrix protein, lumican, lubricin, and any combination thereof.

In one embodiment, the system of the invention detects a desired biomarker with a sensitivity and specificity of at least 90% for joint infection.

In one embodiment, the internal control detector reagent is aggrecan.

The invention also provides a method of diagnosing joint infection in a subject comprising detecting the presence or absence of a biomarker in synovial fluid obtained from a joint in the subject. In one embodiment, the method comprises applying synovial fluid obtained from a joint in the subject to a system, wherein the system comprises a molecule that specifically binds a biomarker for joint infection and a control detector molecule that specifically binds a marker of synovial fluid, wherein detection of the presence or absence of the biomarker and the detection of the marker for synovial fluid diagnoses joint infection in the subject.

In one embodiment, the method comprises a) contacting the synovial fluid obtained from the joint in the subject with an assay buffer, b) applying the synovial fluid so contacted to a system comprising: i) a first region comprising a first detection reagent that detects the presence of a biomarker for infection in synovial fluid, wherein the first detector reagent specifically binds the biomarker, and ii) a second region comprising an internal control detector reagent for verification of synovial fluid, wherein the internal control detector reagent specifically binds a marker of synovial fluid; c) diagnosing joint infection in the patient when the biomarker and marker for synovial fluid are detected.

In one embodiment, joint infection is diagnosed when the second region is detected at a higher intensity than the first region.

In one embodiment, the biomarker is selected from the group consisting of HNP1-3, ELA-2, BPI, NGAL, Resistin, Thrombospondin, Lactoferrin, IL-1β, IL-8, CRP, TNFα, IL-6, FINE, a2M, VEGF, FGF2, SKALP, IP-10, LMP, Orsomucoid, and any combination thereof.

In one embodiment, the marker of synovial fluid is selected from the group consisting of hyaluronic acid (HA), mucopolysaccharide, glucosamine, chondroitin sulfate cartilage oligomeric matrix protein, lumican, lubricin, and any combination thereof.

In one embodiment, the system has a sensitivity and specificity of at least 90% for joint infection.

In one embodiment, the control detector reagent is aggrecan.

In one embodiment, the assay buffer dilutes the synovial fluid to enhance the ability to pipette and transfer the synovial fluid.

In one embodiment, the assay buffer comprises an agent that lyses cellular components present in the synovial fluid.

In one embodiment, the agent is a non-ionic surfactant.

In one embodiment, the assay buffer comprises an agent that preserves the synovial fluid and stabilizes biomarkers present in the synovial fluid.

In one embodiment, the assay buffer comprises an agent that inhibits an interfering component present in the synovial fluid.

In one embodiment, the assay buffer maintains a pH in the range of about 6-8.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

DETAILED DESCRIPTION

Figure 1:
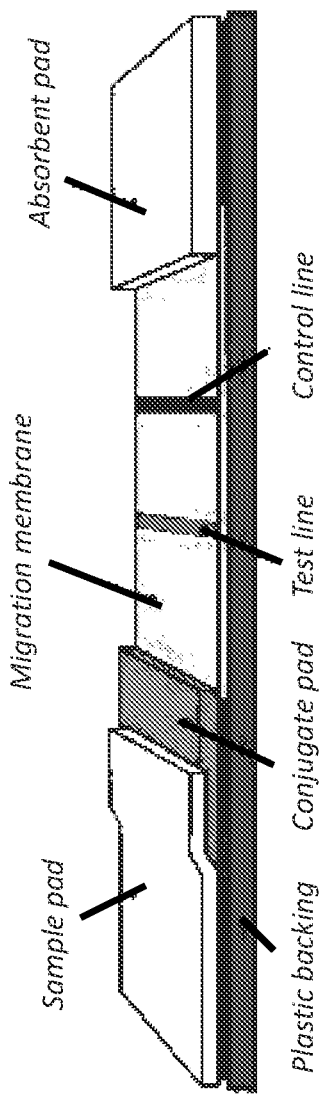
FIG. 1 is an image of an exemplary system for detecting a biomarker in a joint fluid. The image shows the basic components of the system and their relationship to each other. The system includes bottom or plastic backing. The system also includes a test line and a control line.

The present invention relates to a system for conveniently detecting the presence or absence of a biomarker associated with inflammation, as well as determining variable levels of the biomarker in a sample, preferably a synovial fluid sample.

In one embodiment, the invention provides a system for conveniently detecting the presence or absence of a biomarker associated with inflammation in a joint. The inflammation can be in a native joint or a replacement joint. In some instances, the inflammation is associated with an infection.

In one embodiment, the invention relates to an immunoassay device that can be used for detecting a biomarker in a specimen, and an immunoassay method using the same.

In another embodiment, the system of the invention may comprise any method known in the art to effectively detect a biomarker in a sample. Suitable methods include, but are not limited to, immunoassays, enzyme assays, mass spectrometry, biosensors, and chromatography. Thus, the system of the invention includes the use of any type of instrumentality to detect a desired biomarker.

The invention relates to the discovery that one or more genes and corresponding polypeptides, wherein the polypeptides have significant amino acid sequence similarity with a family of proteins that includes the markers of the invention disclosed herein occurs in the synovial fluid of a patient afflicted with infection in a joint of the patient. These polypeptides bind specifically with antibodies that are raised against proteins of that family. Occurrence of these polypeptides in a patient's synovial fluid derived from the infected joint is a diagnostic that the patient is afflicted with infection in the joint. The amount of the polypeptides decreases with effective treatment of the infection of the joint. Thus, the polypeptides can also be used to assess the efficacy of any type of therapy directed to the infected joint.

Accordingly, the system of the invention provides a new and convenient platform for monitoring pathology and response to a particular treatment. In one embodiment, the system of the invention provides a platform for detecting a marker of infection in a joint, preferably periprosthetic joint infection, with at least 80% sensitivity, preferably at least 90%. In one embodiment, the system of the invention provides a platform for detecting a marker of infection in a joint, preferably periprosthetic joint infection with at least 80% specificity, preferably at least 90%. In yet another embodiment, the system allows for the detection of the desired marker with at least 80% sensitivity, preferably at least 90% and at least 80% specificity, preferably at least 90%. In yet another embodiment, the system allows for the detection of the desired marker with at least 80% accuracy, preferably at least 90%.

In one embodiment, the system of the invention can be used to diagnose joint pain, preferably diagnosing the source of inflammation that is associated with the joint pain. In one embodiment, the system of the invention can be used to diagnose joint pain associated with inflammation. In some instances, inflammation in the joint can be caused by bacterial infection. In other instances, the inflammation is associated with periprosthetic joint infection. In one embodiment, joint infection is diagnosed by detecting the presence of the markers of the invention in a sample, such as synovial fluid.

In some instances, the system of the invention may take the form of a user-friendly point-of-use or point-of-care platform, for example a lateral flow device, having a sample application region and a readable detection region to indicate the presence or absence of the biomarker or variable levels of the biomarker. In one embodiment, the readable detection region includes a test line and a control line, wherein the test line detects the biomarker associated with the disease or disorder, and the control line detects the presence or absence of a marker associated with the fluid being tested. Preferably, the fluid being tested is synovial fluid and the marker for synovial fluid includes, but is not limited to, hyaluronic acid (HA), mucopolysaccharide, glucosamine, chondroitin sulfate cartilage oligomeric matrix protein, lumican, lubricin, and the like. In one embodiment, HA is detected in synovial fluid using an agent that binds to HA. Preferably, the agent that binds to HA is an anti-HA antibody, more preferably, the agent that binds HA is aggrecan.

In one embodiment, a comparison of the control line to the test line yields the test result from the diagnostic system of the invention. In some instances, a valid result occurs when the control line is detected at a higher intensity level than the test line. For example, a valid result occurs when the control line is darker than the test line. That is, the control line represents an internal control for the diagnostic system of the invention for verifying that the sample being evaluated is synovial fluid.

In one embodiment, the control line is a reference line that insures that the test has been run correctly. The control line is also used as a reference when the reader determines if the result is positive or negative. For example, the system of the invention is useful for the diagnosis of infection in a joint when the control line is detected at a higher intensity than the test line. In some instances, if the test line is darker than the control line then the test is said to have an invalid result. If the test line is lighter than the control line then the test is said to have a valid result.

In one embodiment, the system of the invention detects a biomarker by way of a lateral flow immunoassay that utilizes strips of cellulose membrane onto which antibodies and other reagents are applied. For example, the test sample moves along the strip due to capillary action and reacts with the reagents at different points along the strip. The end result is the appearance or absence of a detectable line or spot.

In one embodiment, the lateral flow device can be in the form of a cartridge that can be read by a machine. Preferably, the machine is automated.

In one embodiment, the biomarkers of the invention can be detected in a system that takes the form of a laboratory test, for example a type of numbered well plate (e.g., 96 well plate).

DEFINITIONS

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting. The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type.

As used herein the terms "alteration," "defect," "variation," or "mutation," refers to a mutation in a gene in a cell that affects the function, activity, expression (transcription or translation) or conformation of the polypeptide that it encodes. Mutations encompassed by the present invention can be any mutation of a gene in a cell that results in the enhancement or disruption of the function, activity, expression or conformation of the encoded polypeptide, including the complete absence of expression of the encoded protein and can include, for example, missense and nonsense mutations, insertions, deletions, frameshifts and premature terminations. Without being so limited, mutations encompassed by the present invention may alter splicing the mRNA (splice site mutation) or cause a shift in the reading frame (frameshift).

The term "amplification" refers to the operation by which the number of copies of a target nucleotide sequence present in a sample is multiplied.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations. κ and λ light chains refer to the two major antibody light chain isotypes.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

By the term "applicator," as the term is used herein, is meant any device including, but not limited to, a hypodermic syringe, a pipette, an iontophoresis device, a patch, and the like, for administering the compositions of the invention to a subject.

"Aggregation" means a massing together or clustering of independent but similar units, such as particles, parts, or bodies.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequence or a partial nucleotide sequence encoding a protein that elicits an immune response, therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

The term "auto-antigen" means, in accordance with the present invention, any self-antigen which is mistakenly recognized by the immune system as being foreign. Auto-antigens comprise, but are not limited to, cellular proteins, phosphoproteins, cellular surface proteins, cellular lipids, nucleic acids, glycoproteins, including cell surface receptors.

As used herein, "biomarker" in the context of the present invention encompasses, without limitation, proteins, nucleic acids, and metabolites, together with their polymorphisms, mutations, variants, modifications, subunits, fragments, protein-ligand complexes, and degradation products, protein-ligand complexes, elements, related metabolites, and other analytes or sample-derived measures. Biomarkers can also include mutated proteins or mutated nucleic acids. Biomarkers also encompass non-blood borne factors or non-analyte physiological markers of health status, such as clinical parameters, as well as traditional laboratory risk factors. Biomarkers also include any calculated indices created mathematically or combinations of any one or more of the foregoing measurements, including temporal trends and differences.

As used herein, a "biosensor" is an analytical device for the detection of an analyte in a sample. Biosensors can comprise a recognition element, which can recognize or capture a specific analyte, and a transducer, which transmits the presence or absence of an analyte into a detectable signal.

As used herein, the term "data" in relation to one or more biomarkers, or the term "biomarker data" generally refers to data reflective of the absolute and/or relative abundance (level) of a product of a biomarker in a sample. As used herein, the term "dataset" in relation to one or more biomarkers refers to a set of data representing levels of each of one or more biomarker products of a panel of biomarkers in a reference population of subjects. A dataset can be used to generate a formula/classifier of the invention. According to one embodiment, the dataset need not comprise data for each biomarker product of the panel for each individual of the reference population. For example, the "dataset" when used in the context of a dataset to be applied to a formula can refer to data representing levels of products of each biomarker for each individual in one or more reference populations, but as would be understood can also refer to data representing levels of products of each biomarker for 99%, 95%, 90%, 85%, 80%, 75%, 70% or less of the individuals in each of said one or more reference populations and can still be useful for purposes of applying to a formula.

The term "control or reference standard" describes a material comprising none, or a normal, low, or high level of one of more of the marker (or biomarker) expression products of one or more the markers (or biomarkers) of the invention, such that the control or reference standard may serve as a comparator against which a sample can be compared.

As used herein, a "detector molecule" is a molecule that may be used to detect a compound of interest. Non-limiting examples of a detector molecule are molecules that bind specifically to a compound of interest, such as, but not limited to, an antibody, a cognate receptor, and a small molecule.

By the phrase "determining the level of marker (or biomarker) expression" is meant an assessment of the degree of expression of a marker in a sample at the nucleic acid or protein level, using technology available to the skilled artisan to detect a sufficient portion of any marker expression product.

"Differentially increased expression" or "up regulation" refers to biomarker product levels which are at least 10% or more, for example, 20%, 30%, 40%, or 50%, 60%, 70%, 80%, 90% higher or more, and/or 1.1 fold, 1.2 fold, 1.4 fold, 1.6 fold, 1.8 fold, 2.0 fold higher or more, and any and all whole or partial increments therebetween than a control.

"Differentially decreased expression" or "down regulation" refers to biomarker product levels which are at least 10% or more, for example, 20%, 30%, 40%, or 50%, 60%, 70%, 80%, 90% lower or less, and/or 2.0 fold, 1.8 fold, 1.6 fold, 1.4 fold, 1.2 fold, 1.1 fold or less lower, and any and all whole or partial increments therebetween than a control.

A "disease" is a state of health of an animal wherein the animal cannot maintain homeostasis, and wherein if the disease is not ameliorated then the animal's health continues to deteriorate.

As used herein, an "immunoassay" refers to a biochemical test that measures the presence or concentration of a substance in a sample, such as a biological sample, using the reaction of an antibody to its cognate antigen, for example the specific binding of an antibody to a protein. Both the presence of the antigen or the amount of the antigen present can be measured.

As used herein, an "instructional material" includes a publication, a recording, a diagram, or any other medium of expression which can be used to communicate the usefulness of a component of the invention in a kit for detecting biomarkers disclosed herein. The instructional material of the kit of the invention can, for example, be affixed to a container which contains the component of the invention or be shipped together with a container which contains the component. Alternatively, the instructional material can be shipped separately from the container with the intention that the instructional material and the component be used cooperatively by the recipient.

The term "label" when used herein refers to a detectable compound or composition that is conjugated directly or indirectly to a probe to generate a "labeled" probe. The label may be detectable by itself (e.g. radioisotope labels or fluorescent labels) or, in the case of an enzymatic label, may catalyze chemical alteration of a substrate compound or composition that is detectable (e.g., avidin-biotin). In some instances, primers can be labeled to detect a PCR product.

The "level" of one or more biomarkers means the absolute or relative amount or concentration of the biomarker in the sample.

A "marker," as the term is used herein, refers to a molecule that can be detected. Therefore, a marker according to the present invention includes, but is not limited to, a nucleic acid, a polypeptide, a carbohydrate, a lipid, an inorganic molecule, an organic molecule, or a radiolabel, each of which may vary widely in size and properties. A "marker" as used herein can also mean a "biomarker." A "marker" can be detected using any means known in the art or by a previously unknown means that only becomes apparent upon consideration of the marker by the skilled artisan. A marker may be detected using a direct means, or by a method including multiple steps of intermediate processing and/or detection. The term "tag" is also used interchangeably with the term "marker," but the term "tag" may also be used, in certain aspects, to include markers that are associated with one or more other molecules.

The term "marker (or biomarker) expression" as used herein, encompasses the transcription, translation, post-translation modification, and phenotypic manifestation of a gene, including all aspects of the transformation of information encoded in a gene into RNA or protein. By way of non-limiting example, marker expression includes transcription into messenger RNA (mRNA) and translation into protein, as well as transcription into types of RNA such as transfer RNA (tRNA) and ribosomal RNA (rRNA) that are not translated into protein.

The terms "microarray" and "array" refers broadly to both "DNA microarrays" and "DNA chip(s)," and encompasses all art-recognized solid supports, and all art-recognized methods for affixing nucleic acid molecules thereto or for synthesis of nucleic acids thereon. Preferred arrays typically comprise a plurality of different nucleic acid probes that are coupled to a surface of a substrate in different, known locations. These arrays, also described as "microarrays" or colloquially "chips" have been generally described in the art, for example, U.S. Pat. Nos. 5,143,854, 5,445,934, 5,744, 305, 5,677,195, 5,800,992, 6,040,193, 5,424,186 and Fodor et al., 1991, Science, 251:767-777, each of which is incorporated by reference in its entirety for all purposes. Arrays may generally be produced using a variety of techniques, such as mechanical synthesis methods or light directed synthesis methods that incorporate a combination of photolithographic methods and solid phase synthesis methods. Techniques for the synthesis of these arrays using mechanical synthesis methods are described in, e.g., U.S. Pat. Nos. 5,384,261, and 6,040,193, which are incorporated herein by reference in their entirety for all purposes. Although a planar array surface is preferred, the array may be fabricated on a surface of virtually any shape or even a multiplicity of surfaces. Arrays may be nucleic acids on beads, gels, polymeric surfaces, fibers such as fiber optics, glass or any other appropriate substrate. (See U.S. Pat. Nos. 5,770,358, 5,789, 162, 5,708,153, 6,040,193 and 5,800,992, which are hereby incorporated by reference in their entirety for all purposes.) Arrays may be packaged in such a manner as to allow for diagnostic use or can be an all-inclusive device; e.g., U.S. Pat. Nos. 5,856,174 and 5,922,591 incorporated in their entirety by reference for all purposes. Arrays are commercially available from, for example, Affymetrix (Santa Clara, Calif.) and Applied Biosystems (Foster City, Calif.), and are directed to a variety of purposes, including genotyping, diagnostics, mutation analysis, marker expression, and gene expression monitoring for a variety of eukaryotic and prokaryotic organisms. The number of probes on a solid support may be varied by changing the size of the individual features. In one embodiment the feature size is 20 by 25 microns square, in other embodiments features may be, for example, 8 by 8, 5 by 5 or 3 by 3 microns square, resulting in about 2,600,000, 6,600,000 or 18,000,000 individual probe features.

"Measuring" or "measurement," or alternatively "detecting" or "detection," means assessing the presence, absence, quantity or amount (which can be an effective amount) of either a given substance within a clinical or subject-derived sample, including the derivation of qualitative or quantitative concentration levels of such substances, or otherwise evaluating the values or categorization of a subject's clinical parameters.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

"Polypeptide," as used herein refers to a polymer in which the monomers are amino acid residues which are joined together through amide bonds. When the amino acids are alpha-amino acids, either the L-optical isomer or the D-optical isomer can be used, the L-isomers being preferred. The terms "polypeptide" or "protein" or "peptide" as used herein are intended to encompass any amino acid sequence and include modified sequences such as glycoproteins. The term "polypeptide" or "protein" or "peptide" is specifically intended to cover naturally occurring proteins, as well as those which are recombinantly or synthetically produced. It should be noted that the term "polypeptide" or "protein" includes naturally occurring modified forms of the proteins, such as glycosylated forms.

A "reference level" of a biomarker means a level of the biomarker that is indicative of a particular disease state, phenotype, or lack thereof, as well as combinations of disease states, phenotypes, or lack thereof. A "positive" reference level of a biomarker means a level that is indicative of a particular disease state or phenotype. A "negative" reference level of a biomarker means a level that is indicative of a lack of a particular disease state or phenotype.

"Sample" or "biological sample" as used herein means a biological material isolated from an individual. The biological sample may contain any biological material suitable for detecting the desired biomarkers, and may comprise cellular and/or non-cellular material obtained from the individual.

The term "solid support," "support," and "substrate" as used herein are used interchangeably and refer to a material or group of materials having a rigid or semi-rigid surface or surfaces. In one embodiment, at least one surface of the solid support will be substantially flat, although in some embodiments it may be desirable to physically separate synthesis regions for different compounds with, for example, wells, raised regions, pins, etched trenches, or the like. According to other embodiments, the solid support(s) will take the form of beads, resins, gels, microspheres, or other geometric configurations. See U.S. Pat. No. 5,744,305 for exemplary substrates.

As used herein, the term "wild-type" refers to a gene or gene product isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product that displays modifications in sequence and/or functional properties (i.e., altered characteristics) when compared to the wild-type gene or gene product. It is noted that naturally occurring mutants can be isolated; these are identified by the fact that they have altered characteristics (including altered nucleic acid sequences) when compared to the wild-type gene or gene product.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The present invention relates to systems and methods for conveniently monitoring the presence or absence of a biomarker in a joint fluid, as well as determining variable levels of the biomarker joint fluid. Preferably, the joint fluid is synovial fluid.

The invention provides methods and systems for detecting a biomarker in a synovial fluid wherein the system also includes a control in order to ensure that the test sample is indeed synovial fluid. The biomarkers and the control for synovial fluid may be identified by any suitable assay. A suitable assay may include one or more of an enzyme assay, an immunoassay, mass spectrometry, chromatography, electrophoresis, a biosensor, an antibody microarray, or any combination thereof. If an immunoassay is used it may be an enzyme-linked immunosorbant immunoassay (ELISA), a sandwich assay, a competitive assay, a radioimmunoassay (RIA), a lateral flow immunoassay, a Western Blot, an immunoassay using a biosensor, an immunoprecipitation assay, an agglutination assay, a turbidity assay or a nephelometric assay.

Accordingly, the invention includes any platform for detecting a desired biomarker in a biological sample such as synovial fluid. In one embodiment, the system provides a convenient point-of-care device which can quickly detect the presence or absence of a biomarker in an at home or clinical setting. One non-limiting example of a point of care device is a lateral flow immunoassay, which utilizes strips of a membrane, preferably a cellulose membrane, onto which antibodies and other reagents are applied. The sample moves along the strip due to capillary action and reacts with the reagents at different points along the strip. The end result is the appearance or absence of a colored line or spot, which can be compared to a control line. In some instances, the control line is useful for the detection of a marker of synovial fluid (e.g., hyaluronic acid) in order to ensure that the sample tested is indeed synovial fluid. Preferably, the marker of synovial fluid is present at a concentration significantly different in synovial fluid compared to the amount in other common matrices (i.e. blood) so as to validate that the sample tested is synovial fluid.

In one embodiment, the system may include a base or support layer and an absorbent matrix comprising at least one absorbent layer through which a liquid sample can flow along a flow path by force or by capillary action. The base layer may also be absorbent and be in fluid communication with the absorbent matrix, such that the flow path of liquid sample passes through both the absorbent matrix and the base layer. The flow path includes at least two regions, where the first region is a sample application region, and the second region is a detection region.

In one embodiment, the biomarkers of the invention can be detected in a system that takes the form of a laboratory test, for example a type of numbered well plate (e.g., 96 well plate). In one embodiment, the lateral flow device can be in the form of a cartridge that can be read by a machine. Preferably, the machine is automated.

Processing of Synovial Fluid

Synovial fluid is a biological fluid that is found in the synovial cavity of the joints (e.g., knee, hip, shoulder) of the human body between the cartilage and synovium of facing articulating surfaces. Synovial fluid provides nourishment to the cartilage and also serves as a lubricant for the joints. The cells of the cartilage and synovium secrete fluid and the fluid lubricates and reduces friction between the articulating surfaces.

Human synovial fluid is comprised of approximately 85% water. It is derived from the dialysate of blood plasma, which itself is made up of water, dissolved proteins, glucose, clotting factors, mineral ions, hormones, etc. The proteins, albumin and globulins, are present in synovial fluid and are believed to play an important role in the lubrication of the joint area. Other proteins are also found in human synovial fluid, including the glycoproteins such as alpha-1-acid glycoprotein (AGP), alpha-1-antitrypsin (A1AT) and lubricin.

Another compound that is present in human synovial fluid is hyaluronic acid. Hyaluronic acid is also believed to play a role in lubrication. Human synovial fluid further includes other compounds, such as polysaccharides and phospholipids. The phospholipid, dipalmitoylphosphatidylcholine (DPPC), is also present in human synovial fluid. DPPC is generally regarded as surfactant and is also believed to play a role in the lubrication of the joint.

Synovial fluid can be withdrawn from a desired joint for use in the diagnostic system of the invention. The synovial fluid withdrawn can be analyzed in order to obtain clues for the local condition and to receive information about the disease present in the joint. Physical and chemical properties, inflammation markers, presence of leukocytes, antibodies, and the likes can be investigated to diagnose infection in the joint.

Accordingly, the invention provides compositions and methods for detecting the presence of an infection marker in synovial fluid for the diagnosis of the type of infection in a joint as well as a control marker that is associated with the synovial fluid being evaluated. Preferably, control marker for synovial fluid includes, but is not limited to, hyaluronic acid (HA), mucopolysaccharide, glucosamine, chondroitin sulfate cartilage oligomeric matrix protein, lumican, lubricin, and the like.

In one embodiment, the concentration of these synovial fluid markers can be used as a normalizing factor in the systems and assays of the present invention.

Synovial fluid is inherently viscous and presents significant issues when the sample is aspirated or pipetted. Without wishing to be bound by any particular theory, the ideal diluent for synovial fluid contains a buffer capable of maintaining a pH in the range of 6-8. Preferably, the buffer contains saline as a base (i.e. phosphate, Tris). In one embodiment, the buffer contains a detergent that is capable of lysing the cellular material in the synovial fluid sample.

Detergents are amphipathic molecules, meaning they contain both a nonpolar "tail" having aliphatic or aromatic character and a polar "head." Ionic character of the polar head group forms the basis for broad classification of detergents; they may be ionic (charged, either anionic or cationic), nonionic (uncharged) or zwitterionic (having both positively and negatively charged groups but with a net charge of zero). Detergent molecules allow the dispersion (miscibility) of water-insoluble, hydrophobic compounds into aqueous media, including the extraction and solubilization of membrane proteins.

In one embodiment, the buffer of the invention comprises one or more non-ionic detergents, including, but not limited to, N-octyl-β-D-glucopyranside, N-octyl-β-D-maltoside, ZWITTERGENT 3.14, deoxycholate; n-Dodecanoylsucrose; n-Dodecyl-β-D-glucopyranoside; n-Dodecyl-β-D-maltoside; n-Octyl-β-D-glucopyranoside; n-Octyl-β-D-maltopyranoside; n-Octyl-β-D-thioglucopyranoside; n-Decanoylsucrose; n-Decyl-β-D-maltopyranoside; n-Decyl-β-D-thiomaltoside; n-Heptyl-β-D-glucopyranoside; n-Heptyl-β-D-thioglucopyranoside; n-Hexyl-β-D-glucopyranoside; n-Nonyl-β-D-glucopyranoside; n-Octanoylsucrose; n-Octyl-β-D-glucopyranoside; n-Undecyl-β-D-maltoside; APO-10; APO-12; Big CHAP; Big CHAP, Deoxy; BRIJ® 35; $C_{12}E_5$; $C_{12}E_6$; $C_{12}E_8$; $C_{12}E_9$; Cyclohexyl-n-ethyl-β-D-maltoside; Cyclohexyl-n-hexyl-β-D-maltoside; Cyclohexyl-n-methyl-β-D-maltoside; Digitonin; ELUGENT™; GENAPOL® C-100; GENAPOL® X-080; GENAPOL® X-100; HECAMEG; MEGA-10; MEGA-8; MEGA-9; NOGA; NP-40; PLURONIC® F-127; TRITON® X-100; TRITON® X-114; TWEEN® 20; or TWEEN® 80. Additionally, an ionic detergent can be used with the methods of the invention, including, but not limited to BATC, Cetyltrimethylammonium Bromide, Chenodeoxycholic Acid, Cholic Acid, Deoxycholic Acid, Glycocholic Acid, Glycodeoxycholic Acid, Glycolithocholic Acid, Lauroylsarcosine, Taurochenodeoxycholic Acid, Taurocholic Acid, Taurodehydrocholic Acid, Taurolithocholic Acid, Tauroursodeoxycholic Acid, and TOPPA. Zwitterionic detergents can also be used with the compositions and methods of the invention, including, but not limited to, amidosulfobetaines, CHAPS, CHAPSO, carboxybetaines, and methylbetaines. Anionic detergents can also be used with the compositions and methods of the invention, including, but not limited to, e.g. SDS, N-lauryl sarcosine, sodium deoxycholate, alkylaryl sulphonates, long chain (fatty) alcohol sulphates, olefine sulphates and sulphonates, alpha olefine sulphates and sulphonates, sulphated monoglycerides, sulphated ethers, sulphosuccinates, alkane sulphonates, phosphate esters, alkyl isethionates, and sucrose esters.

Generally any suitable liquid may be used as a solvent in the buffer of the present invention. The liquid may be organic or inorganic and may be a pure liquid, a mixture of liquids or a solution of substances in the liquid and may contain additional substances to enhance the properties of the solvent. Any liquid that is suitable for solubilizing the cellular components of body samples in total or in parts may be regarded as a lysis buffer as used herein.

In one embodiment, the solvent is designed, so that cells, cell debris, nucleic acids, polypeptides, lipids and other biomolecules potentially present in the sample are dissolved. In further embodiments of the present invention, the solvent may be designed to assure differential lysis of specific components of the body sample, leaving other components undissolved.

In some instances, the lysis buffer of the invention comprises one or more agents that prevent the degradation of components within the sample. Such components may for example comprise enzyme inhibitors such as proteinase inhibitors, RNAse inhibitors, DNAse inhibitors, nuclease (e.g. endonucleases and exonucleases) inhibitors, etc. Proteinase inhibitors may e.g. comprise inhibitors of serine proteinases, inhibitors of cysteine proteinases, inhibitors of aspartic proteinases, inhibitors of acidic proteinases, inhibitors of alkaline proteinases or inhibitors of neutral proteinases.

In one embodiment, the ideal diluent for processing synovial fluid contains a buffer capable of maintaining a pH in the range of about 5 to about 9, preferably about 6 to about 8, more preferably about 6.5 to about 7.5. Suitable, but non-limiting, buffers include HEPES, PIPES, Tris-Hydrochloride (Tris-HCl), and MOPS.

Optional components for the diluent may be included as part of the composition or as an adjuvant to be added separately, depending on what subsequent purification procedures are performed. Optional components include a defoaming agent at a concentration of about 1%; enzymes such as lysozyme, lyticase, zymolyase, neuraminidase, streptolysin, cellulysin, mutanolysin, chitinase, glucalase or lysostaphin may be used, at a concentration of about 0.1 to 5 mg/ml; one or more inorganic salts such as sodium chloride, potassium chloride, magnesium chloride, calcium chloride, lithium chloride, or praseodymium chloride at a concentration of about 1 mM to 5M; protease inhibitors (e.g., phenylmethylsulfonyl fluoride, trypsin inhibitor, aprotinin, pepstatin A), reducing reagents (e.g., 2-mercaptoethanol and dithiothreitil) at concentrations of 0.1 to 10 mM; chelating agents (e.g., disodium ethylenediaminetetraacetic acid ($Na_2$EDTA), EGTA, CDTA, most preferably at a concentration of about 1 mM or less); one or more ribonucleases (RNase A, T1, T2, and the like) at concentrations ranging from 1 to 400 ug/ml, or any combination of the foregoing. DNase I concentrations may range from 1 to 100 units (10,000 units/mg). Preservatives such as Proclin 950 can be added to the diluent in order to preserve the solution comprising synovial fluid from degradation.

The diluent may also include the addition of heterophilic and Rf factor blocking agents to remove the impact of anti-species antibodies and Rf factor that may exist in the clinical sample. Reagents and methods of the present disclosure generally inhibit interferents from interfering with analysis for a particular analyte. Therefore, it is desirable to substantially suppress a false positive or a false negative signal caused by an interferent, if present, in a sample. In one aspect, such interferents may be, e.g., a heterophilic antibody, a rheumatoid factor, a lipoprotein, a fibrin, a clotting factor, an IgE, a human antibody to allergens, a human anti-mouse immunoglobulin, a human anti-goat immunoglobulin, a human anti-bovine immunoglobulin, a human anti-dog immunoglobulin and a human anti-rabbit immunoglobulin, etc.

Generally, interfering factors (interferents) such as heterophilic antibodies can arise from iatrogenic and noniatrogenic causes. The former may result from the normal response of the human immune system to an administered "foreign" protein antigen. The use of diagnostic or pharmaceutical reagents may lead to the introduction of such proteins and subsequent generation of such antibodies. For example, mouse monoclonal antibodies are foreign proteins in humans and in vivo they may trigger an immune response to produce human anti-mouse antibodies. In many circumstances where mouse monoclonal antibodies have been administered to subjects, those subjects have developed human anti-mouse antibody response.

Accordingly, it is desirable to process synovial fluid and to arrive at an assay buffer that: 1) dilutes the synovial fluid sample to enhance the ability to pipette/transfer the sample, 2) lyses all of the cellular components in the synovial fluid sample, 3) preserves the synovial fluid sample and stabilizes the biomarkers therefrom, and 4) complexes/removes interfering substances from the synovial fluid sample.

In some instances, it is desirable to centrifuge (e.g., spin) the synovial fluid sample prior to assaying the sample. For example, if there is some contamination of the synovial fluid with blood, it is desirable to spin the sample prior to processing in the assay. However in other instances, spinning the synovial fluid is an option whether or not the synovial fluid is contaminated. This is because the results presented herein demonstrate that the differences in the measured level of a biomarker in some instances is not great enough to impact clinical decisions such as where the cutoff is set or whether or not a sample is deemed to be positive or negative for an infection.

Identifying a Marker or Biomarker

The invention includes methods for the identification of differentially expressed markers between samples of non-infected joint and infected joint, as well as methods for the detection of the expression products of differentially expressed markers of non-infected joint and infected joint. In one embodiment, the joint can be a native joint (e.g., RA, Gout, Pseudogout) or a replacement joint. In one embodiment, the invention provides a method for detecting periprosthetic infection, also known as "septic failure."

The invention contemplates the identification of differentially expressed markers by whole genome nucleic acid microarray, to identify markers differentially expressed between non-infected joint and infected joint. The invention further contemplates using methods known to those skilled in the art to detect and to measure the level of differentially expressed marker expression products, such as RNA and protein, to measure the level of one or more differentially expressed marker expression products.

In one embodiment, the invention includes a gene signature differential analysis method designed to detect genes present in one sample set, and absent in another. Genes with differential expression in cells from sites of infection or inflammation versus normal tissue are better diagnostic and therapeutic targets than genes that do not change in expression.

Analysis for the purpose of monitoring differential gene expression may be focused on a variety of tissues and fluids, and may also be used to detect or measure a number of different molecular targets. When a cell expresses a gene, it transcribes the appropriate RNA, which is ultimately translated into a protein. The relevant protein may then be localized to a variety of intracellular or extracellular locations.

Methods of detecting or measuring gene expression may utilize methods that focus on cellular components (cellular examination), or methods that focus on examining extracellular components (fluid examination). Because gene expression involves the ordered production of a number of different molecules, a cellular or fluid examination may be used to detect or measure a variety of molecules including RNA, protein, and a number of molecules that may be modified as a result of the protein's function. Typical diagnostic methods focusing on nucleic acids include amplification techniques such as PCR and RT-PCR (including quantitative variants), and hybridization techniques such as in situ hybridization, microarrays, blots, and others. Typical diagnostic methods focusing on proteins include binding techniques such as ELISA, imunohistochemistry, microarray and functional techniques such as enzymatic assays.

The practice of the present invention may also employ software and systems. Computer software products of the invention typically include computer readable medium having computer-executable instructions for performing the logic steps of the method of the invention. Suitable computer readable medium include floppy disk, CD-ROM/DVD/DVD-ROM, hard-disk drive, flash memory, ROM/RAM, magnetic tapes and etc. The computer executable instructions may be written in a suitable computer language or combination of several languages. Basic computational biology methods are described in, for example Setubal and Meidanis et al., Introduction to Computational Biology Methods (PWS Publishing Company, Boston, 1997); Salzberg, Searles, Kasif, (Ed.), Computational Methods in Molecular Biology, (Elsevier, Amsterdam, 1998); Rashidi and Buehler, Bioinformatics Basics: Application in Biological Science and Medicine (CRC Press, London, 2000) and Ouelette and Bzevanis Bioinformatics: A Practical Guide for Analysis of Gene and Proteins (Wiley & Sons, Inc., 2nd ed., 2001). See U.S. Pat. No. 6,420,108.

The present invention may also make use of various computer program products and software for a variety of purposes, such as probe design, management of data, analysis, and instrument operation. See, U.S. Pat. Nos. 5,593,839, 5,795,716, 5,733,729, 5,974,164, 6,066,454, 6,090,555, 6,185,561, 6,188,783, 6,223,127, 6,229,911 and 6,308,170. Additionally, the present invention may have preferred embodiments that include methods for providing genetic information over networks such as the Internet as shown in US Pub No 20020183936.

The genes identified as being differentially expressed may be assessed in a variety of nucleic acid detection assays to detect or quantify the expression level of a gene or multiple genes in a given sample. For example, traditional Northern blotting, nuclease protection, RT-PCR, microarray, and differential display methods may be used for detecting gene expression levels. Methods for assaying for mRNA include Northern blots, slot blots, dot blots, and hybridization to an ordered array of oligonucleotides. Any method for specifically and quantitatively measuring a specific protein or mRNA or DNA product can be used. However, methods and assays are most efficiently designed with array or chip hybridization-based methods for detecting the expression of a large number of genes. Any hybridization assay format may be used, including solution-based and solid support-based assay formats.

The protein products of the genes identified herein can also be assayed to determine the amount of expression. Methods for assaying for a protein include Western blot, immunoprecipitation, and radioimmunoassay. The proteins analyzed may be localized intracellularly (most commonly an application of immunohistochemistry) or extracellularly (most commonly an application of immunoassays such as ELISA).

Biological samples may be of any biological tissue or fluid containing leukocytes. Frequently the sample will be a "clinical sample" which is a sample derived from a patient. Typical clinical samples include, but are not limited to, synovial fluid, sputum, blood, blood-cells (e.g., white cells), tissue or fine needle biopsy samples, urine, peritoneal fluid, cerebrospinal fluid, abscesses, and pleural fluid, or cells therefrom. Biological samples may also include sections of tissues, such as frozen sections or formalin fixed sections taken for histological purposes. Periprosthetic tissues are often analyzed for evidence of infection.

Controls groups may either be normal (i.e., not infected or not-inflamed tissue, for example) or samples from known types or stages of infection or inflammation or other disease. As described below, comparison of the expression patterns of the sample to be tested with those of the controls can be used to diagnose infection in the joint. In some instances, the control groups are only for the purposes of establishing initial cutoffs for the assays of the invention. Therefore, in some instances, the systems and methods of the invention can diagnose infection in a joint without the need to compare with a control group.

Biomarkers

In one embodiment, the system disclosed herein includes application of synovial fluid obtained from a test sample to a system for the detection of one or more biomarkers that are upregulated in inflammation in a joint, preferably by at least two-fold increase compared to a normal joint. In some instances, the inflammation is associated with an infection (e.g., joint infection). Joint infection can be in a native joint or a replacement joint. Preferably, the joint infection is a periprosthetic joint infection. Such biomarkers include, but are not limited to, IL-1a (Interleukin 1-alpha), IL-1β (Interleukin 1-beta), IL-1ra (Interleukin 1 receptor antagonist), IL-4 (Interleukin 4), IL-5 (Interleukin 5), IL-6 (Interleukin 6), IL-8 (Interleukin 8), IL-10 (Interleukin 10), IL-17 (Interleukin 17), ENA-78 (Epithelial cell-derived neutrophil-activating peptide 78), FGF-Basic (Fibroblast growth factor basic), G-CSF (Granulocyte colony-stimulating factor), GM-CSF (Granulocyte monocyte colony-stimulating factor), IFN-g (Interferon gamma), MCP-1 (Monocyte chemotactic protein 1), MIP-1a (Macrophage inflammatory protein 1-alpha), MIP-1B (Macrophage inflammatory protein 1-beta), Rantes (Regulated upon Activation, Normal T-cell Expressed, and Secreted), TNF-a (Tumor necrosis factor alpha), Tpo (Thrombopoietin), VEGF (Vascular endothelial growth factor), SKALP (Skin derived antileukoproteinase), SLP-1 (Secretory leukocyte peptidase inhibitor), CRP (C-Reactive Protein), a-2M (Alpha-2-macroglobulin), LE (Leucocyte Esterase), PCT (Procalcitonin), LBP (Liposaccaride binding protein), CGRP (Calictonin gene-related peptide), and the like. Exemplary biomarkers that are upregulated in septic as compared to aseptic inflammation include those listed in U.S. Pat. No. 7,598,080, which is incorporated by reference herein in its entirety. Septic inflammation in the joint can be caused by an infection of viral, bacterial, or parasitic origin.

In one embodiment, the system disclosed herein includes application of a synovial fluid from a test sample to a system for the detection of one or more biomarker that is upregulated in joint infection. The joint infection can be in a native joint or a replacement joint. Preferably, the joint infection is a periprosthetic joint infection. Such biomarkers include, but are not limited to, IL-1β, IL-6, IL-8, TNFα, G-CSF, IL-1a, VEGF, IP-10, BFGF (aka FGF2), CRP, a2M, SKALP, FINE Enzyme assay, Lactoferrin, Lipocalin-2/NGAL, Neutrophil Elastase-2 (ELA2), Resistin, Thrombospondin-1 (TSP-1), HNP1-3, and BPI.

In another embodiment, the system disclosed herein includes application of synovial fluid obtained from a test sample to system for the detection of one or more biomarkers that are down regulated in joint infection, preferably by at least two-fold increase compared to a normal joint. The joint infection can be in a native joint or a replacement joint. Preferably, the joint infection is a periprosthetic joint infection. Exemplary biomarkers that are down regulated in septic as compared to aseptic inflammation include those listed in U.S. Pat. No. 7,598,080. In some instances, biomarkers that are downregulated in septic inflammation include biomarkers that are upregulated in gout. Such biomarkers include, but are not limited to, fatty acid binding protein 5 (psoriasis-associated), CD36 antigen (collagen type I receptor, thrombospondin receptor), CD9 antigen (p24), lipase A (lysosomal acid, cholesterol esterase (Wolman disease)), glycoprotein (transmembrane) nmb, Fc fragment of IgE (high affinity I, receptor for; alpha polypeptide), potassium channel tetramerisation domain containing 12, membrane-spanning 4-domains (subfamily A, member 4), legumain, fibronectin 1, V-set and immunoglobulin domain containing 4, v-maf musculoaponeurotic fibrosarcoma oncogene homolog B (avian), chondroitin sulfate proteoglycan 2 (versican), histamine N-methyltransferase, disabled homolog 2, mitogen-responsive phosphoprotein (*Drosophila*), cytochrome P450 (family 1, subfamily B, polypeptide 1), carboxypeptidase, vitellogenic-like, serine dehydratase, high mobility group nucleosomal binding domain 3, annexin A4, and the like.

The present invention is partly based on the discovery that the cells in an inflamed knee, despite appearing the same irrespective of the source of the inflammation, have different and diagnostic gene expression profiles. For example, a diagnostic gene expression signature and corresponding protein expression signature can be obtained by comparing results in cells present in synovial fluid from patients with confirmed bacterial infection as compared to patients with aseptic loosening or patients with inflammation that is not caused by infection (e.g., gout). Controls may include normal synovial fluid (i.e., not infected or not-inflamed synovial fluid, for example) or synovial fluid obtained from joints having known types or stages of infection or inflammation. As described elsewhere herein, comparison of the expression patterns of the sample to be tested with those of the controls is used to establish initial cutoffs for the systems of the invention.

The system of the invention can be used to detect at least one, two, three, four, five, or at least ten different biomarkers. In some examples, the system includes determining a proteomic profile. In other examples, the system of the invention includes detecting a proteomic profile including at least 1, 2, 3, 4, 5, 6, 7, 8, 9, 10, or all of these proteins, including any of the proteins set forth in herein or those listed in U.S. Pat. No. 7,598,080. In one embodiment of the invention, the system can detect nucleic acids that encode the protein biomarker or biomarkers of the invention.

In one embodiment, the invention provides a system for detecting a biomarker of infection in a joint, preferably periprosthetic joint infection, with at least 90%, 91%, 92%, 93%, 94%, 95%, 96%, 97%, 98%, 99%, 100% sensitivity; at least 90%, 91%, 92%, 93%, 94%, 95%, 96%, 97%, 98%, 99%, 100% specificity; or both at least 90%, 91%, 92%, 93%, 94%, 95%, 96%, 97%, 98%, 99%, 100% sensitivity and specificity. In one embodiment, the invention provides a system for detecting a biomarker of infection in joint with at least 90%, 91%, 92%, 93%, 94%, 95%, 96%, 97%, 98%, 99%, 100% accuracy.

In one embodiment, the system is able to detect HNP1-3 as a marker for periprosthetic joint infection with at least 90% sensitivity and specificity. The cut-off value (derived by ROC analysis) for HNP1-3 as a marker is about 5000 ng/ml, preferably about 6000 ng/ml, preferably about 7000 ng/ml, preferably about 8000 ng/ml, preferably about 9000 ng/ml, preferably about 10000 ng/ml, most preferably about 7720 ng/ml. The cut-off range for HNP1-3 as a marker for periprosthetic joint infection with at least 90% sensitivity and specificity is about 1000 ng/ml-19000 ng/ml, preferably about 2000 ng/ml-16000 ng/ml, preferably about 3000 ng/ml-13000 ng/ml, most preferably about 3334 ng/ml-10946 ng/ml.

In one embodiment, the system is able to detect ELA-2 as a marker for periprosthetic joint infection with at least 90% sensitivity and specificity. The cut-off value (derived by ROC analysis) for ELA-2 as a marker is about 600 ng/ml, preferably about 700 ng/ml, preferably about 800 ng/ml, preferably about 900 ng/ml, preferably about 1000 ng/ml, preferably about 1100 ng/ml, preferably about 1200 ng/ml, most preferably about 942 ng/ml. The cut-off range for ELA-2 as a marker for periprosthetic joint infection with at least 90% sensitivity and specificity is about 400 ng/ml-28000 ng/ml, preferably about 500 ng/ml-25000 ng/ml, preferably about 600 ng/ml-22000 ng/ml, most preferably about 721 ng/ml-19000 ng/ml.

In one embodiment, the system is able to detect NGAL as a marker for periprosthetic joint infection with at least 90% sensitivity and specificity. The cut-off value (derived by ROC analysis) for NGAL as a marker is about 1400 ng/ml, preferably about 1500 ng/ml, preferably about 1600 ng/ml, preferably about 1700 ng/ml, preferably about 1800 ng/ml, preferably about 1900 ng/ml, most preferably about 1644 ng/ml. The cut-off range for NGAL as a marker for periprosthetic joint infection with at least 90% sensitivity and specificity is about 800 ng/ml-3600 ng/ml, preferably about 900 ng/ml-3500 ng/ml, preferably about 1000 ng/ml-3400 ng/ml, most preferably about 1100 ng/ml-3200 ng/ml.

In one embodiment, the system is able to detect Resistin as a marker for periprosthetic joint infection with at least 90% sensitivity and specificity. The cut-off value (derived by ROC analysis) for Resistin as a marker is about 50 ng/ml, preferably about 60 ng/ml, preferably about 70 ng/ml, preferably about 80 ng/ml, preferably about 90 ng/ml, preferably about 100 ng/ml, preferably about 110 ng/ml, most preferably about 82.9 ng/ml. The cut-off range for Resistin as a marker for periprosthetic joint infection with at least 90% sensitivity and specificity is about 30 ng/ml-150 ng/ml, preferably about 40 ng/ml-140 ng/ml, preferably about 50 ng/ml-130 ng/ml, most preferably about 53 ng/ml-112 ng/ml.

In one embodiment, the system is able to detect Thrombospondin as a marker for periprosthetic joint infection with at least 90% sensitivity and specificity. The cut-off value (derived by ROC analysis) for Thrombospondin as a marker is about 100 ng/ml, preferably about 110 ng/ml, preferably about 120 ng/ml, preferably about 130 ng/ml, preferably about 140 ng/ml, preferably about 150 ng/ml, preferably about 160 ng/ml, most preferably about 136 ng/ml. The cut-off range for Thrombospondin as a marker for periprosthetic joint infection with at least 90% sensitivity and specificity is about 100 ng/ml-170 ng/ml, preferably about 110 ng/ml 160 ng/ml, preferably about 120 ng/ml-150 ng/ml, most preferably about 131 ng/ml-141 ng/ml.

In one embodiment, the system is able to detect Lactoferrin as a marker for periprosthetic joint infection with at least 90% sensitivity and specificity. The cut-off value (derived by ROC analysis) for Lactoferrin as a marker is about 2700 ng/ml, preferably about 2800 ng/ml, preferably about 2900 ng/ml, preferably about 3000 ng/ml, preferably about 3100 ng/ml, preferably about 3200 ng/ml, preferably about 3300 ng/ml, most preferably about 2993 ng/ml. The cut-off range for Lactoferrin as a marker for periprosthetic joint infection with at least 90% sensitivity and specificity is about 900 ng/ml-5000 ng/ml, preferably about 1000 ng/ml-4900 ng/ml, preferably about 1100 ng/ml-4800 ng/ml, most preferably about 1200 ng/ml-4700 ng/ml.

In one embodiment, the system is able to detect IL-1β as a marker for periprosthetic joint infection with at least 90% sensitivity and specificity. The cut-off value (derived by ROC analysis) for IL-1β as a marker is about 20 pg/ml, preferably about 25 pg/ml, preferably about 30 pg/ml, preferably about 35 pg/ml, preferably about 40 pg/ml, preferably about 45 pg/ml, preferably about 50 pg/ml, most preferably about 33.25 pg/ml. The cut-off range for IL-1β as a marker for periprosthetic joint infection with at least 90% sensitivity and specificity is about 15 pg/ml-50 pg/ml, preferably about 20 pg/ml 45 pg/ml, preferably about 25 pg/ml-40 pg/ml, most preferably about 30 pg/ml-35 pg/ml.

In one embodiment, the system is able to detect IL-8 as a marker for periprosthetic joint infection with at least 90% sensitivity and specificity. The cut-off value (derived by ROC analysis) for IL-8 as a marker is about 6500 pg/ml, preferably about 6600 pg/ml, preferably about 6700 pg/ml, preferably about 6800 pg/ml, preferably about 6900 pg/ml, preferably about 7000 pg/ml, preferably about 7100 pg/ml, most preferably about 6797 pg/ml. The cut-off range for IL-8 as a marker for periprosthetic joint infection with at least 90% sensitivity and specificity is about 6500 pg/ml-7100 pg/ml, preferably about 6600 pg/ml-7000 pg/ml, preferably about 6700 pg/ml-6900 pg/ml, most preferably about 6725 pg/ml-6860 pg/ml.

In one embodiment, the system is able to detect IL-1β as a marker for periprosthetic joint infection with at least 90% sensitivity and specificity. The cut-off value (derived by ROC analysis) for IL-1β as a marker is about 20 pg/ml, preferably about 9 pg/ml, preferably about 12 pg/ml, preferably about 15 pg/ml, preferably about 19 pg/ml, preferably about 22 pg/ml, preferably about 25 pg/ml, most preferably about 16.25 pg/ml. The cut-off range for IL-1β as a marker for periprosthetic joint infection with at least 90% sensitivity and specificity is about 4 pg/ml-26 pg/ml, preferably about 6 pg/ml-24 pg/ml, preferably about 8 pg/ml-22 pg/ml, most preferably about 10 pg/ml-20 pg/ml.

In one embodiment, the system is able to detect CRP as a marker for periprosthetic joint infection with at least 90% sensitivity and specificity. The cut-off value (derived by ROC analysis) for CRP as a marker is about 8000 ng/ml, preferably about 9000 ng/ml, preferably about 10000 ng/ml, preferably about 11000 ng/ml, preferably about 12000 ng/ml, preferably about 13000 ng/ml, preferably about 14000 ng/ml, most preferably about 11412 ng/ml. The cut-off range for CRP as a marker for periprosthetic joint infection with at least 90% sensitivity and specificity is about 8000 ng/ml-15000 ng/ml, preferably about 9000 ng/ml-14000 ng/ml, preferably about 10000 ng/ml-13000 ng/ml, most preferably about 11000 ng/ml-12000 ng/ml.

In one embodiment, the system is able to detect TNFα as a marker for periprosthetic joint infection with at least 90% sensitivity and specificity. The cut-off value (derived by ROC analysis) for TNFα as a marker is about 40 pg/ml, preferably about 50 pg/ml, preferably about 60 pg/ml, preferably about 70 pg/ml, preferably about 80 pg/ml, preferably about 90 pg/ml, preferably about 100 pg/ml, most preferably about 66.42 pg/ml. The cut-off range for TNFα as a marker for periprosthetic joint infection with at least 90% sensitivity and specificity is about 46 pg/ml-120 pg/ml, preferably about 59 pg/ml-110 pg/ml, preferably about 62 pg/ml-100 pg/ml, most preferably about 65 pg/ml-88 pg/ml.

In one embodiment, the system is able to detect IL-6 as a marker for periprosthetic joint infection with at least 90% sensitivity and specificity. The cut-off value (derived by ROC analysis) for IL-6 as a marker is about 2900 pg/ml, preferably about 3000 pg/ml, preferably about 3100 pg/ml, preferably about 3200 pg/ml, preferably about 3300 pg/ml, preferably about 3400 pg/ml, preferably about 3500 pg/ml, most preferably about 3102 pg/ml. The cut-off range for IL-6 (Biorad) as a marker for periprosthetic joint infection with at least 90% sensitivity and specificity is about 2300 pg/ml-3700 pg/ml, preferably about 2400 pg/ml-3600 pg/ml, preferably about 2500 pg/ml-3500 pg/ml, most preferably about 2615 pg/ml-3400 pg/ml.

In one embodiment, the system is able to detect IL-6 as a marker for periprosthetic joint infection with at least 90% sensitivity and specificity. The cut-off value (derived by ROC analysis) for IL-6 as a marker is about 1000 pg/ml, preferably about 1500 pg/ml, preferably about 2000 pg/ml, preferably about 3000 pg/ml, preferably about 4000 pg/ml, preferably about 5000 pg/ml, preferably about 6000 pg/ml, most preferably about 3472 pg/ml. The cut-off range for IL-6 as a marker for periprosthetic joint infection with at least 90% sensitivity and specificity is about 1600 pg/ml-5900 pg/ml, preferably about 1700 pg/ml-5600 pg/ml, preferably about 1800 pg/ml-5300 pg/ml, most preferably about 1965 pg/ml-5000 pg/ml.

In one embodiment, the system is able to detect Human neutrophil elastase (HNE) as a marker for periprosthetic joint infection with at least 90% sensitivity and specificity. The cut-off value (derived by ROC analysis) for HNE as a marker is about 400 ng/ml, preferably about 450 ng/ml, preferably about 500 ng/ml, preferably about 550 ng/ml, preferably about 600 ng/ml, preferably about 650 ng/ml, preferably about 700 ng/ml, most preferably about 552.8 ng/ml. The cut-off range for HNE as a marker for periprosthetic joint infection with at least 90% sensitivity and specificity is about 400 ng/ml-700 ng/ml, preferably about 450 ng/ml-650 ng/ml, preferably about 500 ng/ml-600 ng/ml, most preferably about 521 ng/ml-584 ng/ml.

In one embodiment, the system is able to detect alpha(2)-macroglobulin (a2M) as a marker for periprosthetic joint infection with at least 90% sensitivity and specificity. The cut-off value (derived by ROC analysis) for a2M as a marker is about 40 pg/ml, preferably about 50 pg/ml, preferably about 60 pg/ml, preferably about 70 pg/ml, preferably about 80 pg/ml, preferably about 90 pg/ml, preferably about 100 pg/ml, most preferably about 73.45 pg/ml. The cut-off range for a2M as a marker for periprosthetic joint infection with at least 90% sensitivity and specificity is about 65 pg/ml-90 pg/ml, preferably about 70 pg/ml-85 pg/ml, preferably about 75 pg/ml-80 pg/ml, most preferably about 70 pg/ml-76 pg/ml.

In one embodiment, the system is able to detect VEGF as a marker for periprosthetic joint infection with at least 90% sensitivity and specificity. The cut-off value (derived by ROC analysis) for VEGF as a marker is about 1800 pg/ml, preferably about 2100 pg/ml, preferably about 2400 pg/ml, preferably about 2700 pg/ml, preferably about 3000 pg/ml, preferably about 3300 pg/ml, preferably about 3700 pg/ml, most preferably about 2565 pg/ml. The cut-off range for VEGF as a marker for periprosthetic joint infection with at least 90% sensitivity and specificity is about 1900 pg/ml-3700 pg/ml, preferably about 2100 pg/ml-3700 pg/ml, preferably about 2300 pg/ml-3500 pg/ml, most preferably about 2500 pg/ml-3300 pg/ml.

In one embodiment, the system is able to detect FGF2 as a marker for periprosthetic joint infection with at least 90% sensitivity and specificity. The cut-off value (derived by ROC analysis) for FGF2 as a marker is about 0.5 pg/ml, preferably about 1 pg/ml, preferably about 4 pg/ml, preferably about 8 pg/ml, preferably about 12 pg/ml, preferably about 16 pg/ml, preferably about 20 pg/ml, most preferably about 2.25 pg/ml. The cut-off range for FGF2 as a marker for periprosthetic joint infection with at least 90% sensitivity and specificity is about 0.4 pg/ml-16 pg/ml, preferably about 0.6 pg/ml-16 pg/ml, preferably about 0.8 pg/ml-14 pg/ml, most preferably about 1 pg/ml-12 pg/ml.

In one embodiment, the system is able to detect G-CSF as a marker for periprosthetic joint infection with at least 90% sensitivity and specificity. The cut-off value (derived by ROC analysis) for G-CSF as a marker is about 40 pg/ml, preferably about 60 pg/ml, preferably about 80 pg/ml, preferably about 100 pg/ml, preferably about 120 pg/ml, preferably about 140 pg/ml, preferably about 160 pg/ml, most preferably about 94.35 pg/ml. The cut-off range for G-CSF as a marker for periprosthetic joint infection with at least 90% sensitivity and specificity is about 55 pg/ml-160 pg/ml, preferably about 60 pg/ml-140 pg/ml, preferably about 65 pg/ml-120 pg/ml, most preferably about 74 pg/ml-100 pg/ml.

In one embodiment, the system is able to detect SKALP as a marker for periprosthetic joint infection with at least 90% sensitivity and specificity. The cut-off value (derived by ROC analysis) for SKALP as a marker is about 1500 pg/ml, preferably about 2000 pg/ml, preferably about 2500 pg/ml, preferably about 3000 pg/ml, preferably about 3500 pg/ml, preferably about 4000 pg/ml, preferably about 4500 pg/ml, most preferably about 3721 pg/ml. The cut-off range for SKALP as a marker for periprosthetic joint infection with at least 90% sensitivity and specificity is about 1500 pg/ml-5000 pg/ml, preferably about 1700 pg/ml-4500 pg/ml, preferably about 1900 pg/ml-4000 pg/ml, most preferably about 2100 pg/ml-3800 pg/ml.

In one embodiment, the system is able to detect IP-10 as a marker for periprosthetic joint infection with at least 90% sensitivity and specificity. The cut-off value (derived by ROC analysis) for IP-10 as a marker is about 3500 pg/ml, preferably about 4000 pg/ml, preferably about 4500 pg/ml, preferably about 5000 pg/ml, preferably about 5500 pg/ml, preferably about 6000 pg/ml, preferably about 6500 pg/ml, most preferably about 5003 pg/ml. The cut-off range for IP-10 as a marker for periprosthetic joint infection with at least 90% sensitivity and specificity is about 3000 pg/ml-7000 pg/ml, preferably about 3500 pg/ml-6500 pg/ml, preferably about 4000 pg/ml-6000 pg/ml, most preferably about 4500 pg/ml-5800 pg/ml.

In one aspect, the present disclosure relates to immunoassays for assessing (e.g., detecting or quantifying) at least one biomarker of interest in a test sample, where the sensitivity of the immunoassay is improved relative to, specifically is from about three to about fifteen times, especially, from about two to about ten times, higher than, the sensitivity of conventional immunoassays known in the art.

Controls with respect to the presence or absence of the biomarker or differential expression of the biomarker may either be normal (i.e., not infected or not-inflamed tissue, for example) or samples from known types or stages of infection or inflammation or other disease. As described elsewhere herein, comparison of the expression patterns of the sample to be tested with those of the controls can be used to diagnose the disease or disorder. In this context, the control or control group is used for purposes of establishing initial cutoffs for the systems and assay of the invention. Therefore, mere detection of a biomarker of the invention without the requirement of comparison to a control group can diagnose the disease or disorder in the joint. In this manner, the system according to the present invention may be used for qualitative (yes/no answer); semi-quantitative (−/+/++/+++/++++) or quantitative answer.

Changes in the levels of expression of the biomarker are associated with pathogenesis. Thus, changes in the expression levels of particular biomarkers serve as signposts for the presence of and progression of infection in the joint. For example, it is the differences in expression of particular biomarkers that are used to determine whether the infection in the joint is caused by an aseptic or spetic inflammation.

Disease

The incidence of prosthetic joint infection is higher after a revision arthroplasty which may be due to the long operation time, scar formation, or recrudescence of unrecognized infection present at the initial surgery. In certain cases where antibiotic treatment is not effective, it may mean removing the implant outright, and cleaning the implant and infected area before replacing the joint, which is costly, both in terms of expenses, time and the patient's condition. The procedure involves a surgical incision, drainage of the area, hardware removal and debridement of all devitalized tissue in conjunction with long term bed rest, pharmacological treatment followed by replacement of the joint.

In one embodiment of the invention, detection of a marker in a sample identifies a subject from which the sample was obtained, as having or not having a particular pathology. For example, the invention provides the ability to detect a marker in a synovial fluid sample, wherein detection of the marker identifies whether inflammation in the joint of the subject is caused by an infection not.

In one embodiment, the invention provides a system for quickly diagnosing whether the inflammation in the joint is caused by an infection or not. Determination of the source of inflammation enables the physician to apply the appropriate therapy to ameliorate the inflammation. For example, if the subject has a bacterial infection in the joint, the patient is treated with anti-bacterial. Alternatively, if the diagnosis indicates that the inflammation is not caused by a bacterial infection, the physician can apply the appropriate type of therapy to treat aseptic inflammation.

Detecting a Biomarker

The concentration of the biomarker in a sample may be determined by any suitable assay. A suitable assay may include one or more of the following methods, an enzyme assay, an immunoassay, mass spectrometry, chromatography, electrophoresis or an antibody microarray, or any combination thereof. Thus, as would be understood by one skilled in the art, the system and methods of the invention may include any method known in the art to detect a biomarker in a sample.

The invention described herein also relates to methods for a multiplex analysis platform. In one embodiment, the method comprises an analytical method for multiplexing analytical measurements of markers. In another embodiment, the method comprises a set of compatible analytical strategies for multiplex measurements of markers and/or metabolites in synovial fluid.

In one embodiment, the sample of the invention is a biological sample. The biological sample can originate from solid or fluid samples. The sample of the invention may comprise synovial fluid, urine, whole blood, blood serum, blood plasma, sweat, cerebrospinal fluid, mucous, saliva, lymph, bronchial aspirates, milk and the like. Preferably the sample is synovial fluid.

Immunoassays

In one embodiment, the systems and methods of the invention can be performed in the form of various immunoassay formats, which are well known in the art. Immunoassays, in their most simple and direct sense, are binding assays involving binding between antibodies and antigen. Many types and formats of immunoassays are known and all are suitable for detecting the disclosed biomarkers. Examples of immunoassays are enzyme linked immunosorbent assays (ELISAs), enzyme linked immunospot assay (ELISPOT), radioimmunoassays (RIA), radioimmune precipitation assays (RIPA), immunobead capture assays, Western blotting, dot blotting, gel-shift assays, Flow cytometry, protein arrays, multiplexed bead arrays, magnetic capture, in vivo imaging, fluorescence resonance energy transfer (FRET), fluorescence recovery/localization after photobleaching (FRAP/FLAP), a sandwich assay, a competitive assay, an immunoassay using a biosensor, an immunoprecipitation assay, an agglutination assay, a turbidity assay, a nephlelometric assay, etc.

In general, immunoassays involve contacting a sample suspected of containing a molecule of interest (such as the disclosed biomarkers) with an antibody to the molecule of interest or contacting an antibody to a molecule of interest (such as antibodies to the disclosed biomarkers) with a molecule that can be bound by the antibody, as the case may be, under conditions effective to allow the formation of immunocomplexes. Contacting a sample with the antibody to the molecule of interest or with the molecule that can be bound by an antibody to the molecule of interest under conditions effective and for a period of time sufficient to allow the formation of immune complexes (primary immune complexes) is generally a matter of simply bringing into contact the molecule or antibody and the sample and incubating the mixture for a period of time long enough for the antibodies to form immune complexes with, i.e., to bind to, any molecules (e.g., antigens) present to which the antibodies can bind. In many forms of immunoassay, the sample-antibody composition, such as a tissue section, ELISA plate, dot blot or Western blot, can then be washed to remove any non-specifically bound antibody species, allowing only those antibodies specifically bound within the primary immune complexes to be detected.

Immunoassays can include methods for detecting or quantifying the amount of a molecule of interest (such as the disclosed biomarkers or their antibodies) in a sample, which methods generally involve the detection or quantitation of any immune complexes formed during the binding process. In general, the detection of immunocomplex formation is well known in the art and can be achieved through the application of numerous approaches. These methods are generally based upon the detection of a label or marker, such as any radioactive, fluorescent, biological or enzymatic tags or any other known label. See, for example, U.S. Pat. Nos. 3,817,837; 3,850,752; 3,939,350; 3,996,345; 4,277,437; 4,275,149 and 4,366,241, each of which is incorporated herein by reference in its entirety and specifically for teachings regarding immunodetection methods and labels.

As used herein, a label can include a fluorescent dye, a member of a binding pair, such as biotin/streptavidin, a metal (e.g., gold), or an epitope tag that can specifically interact with a molecule that can be detected, such as by producing a colored substrate or fluorescence. Substances suitable for detectably labeling proteins include fluorescent dyes (also known herein as fluorochromes and fluorophores) and enzymes that react with colorometric substrates (e.g., horseradish peroxidase). The use of fluorescent dyes is generally preferred in the practice of the invention as they can be detected at very low amounts. Furthermore, in the case where multiple antigens are reacted with a single array, each antigen can be labeled with a distinct fluorescent compound for simultaneous detection. Labeled spots on the array are detected using a fluorimeter, the presence of a signal indicating an antigen bound to a specific antibody.

Fluorophores are compounds or molecules that luminesce. Typically fluorophores absorb electromagnetic energy at one wavelength and emit electromagnetic energy at a second wavelength.

There are two main types of immunoassays, homogeneous and heterogeneous. In homogeneous immunoassays, both the immunological reaction between an antigen and an antibody and the detection are carried out in a homogeneous reaction. Heterogeneous immunoassays include at least one separation step, which allows the differentiation of reaction products from unreacted reagents. A variety of immunoassays can be used to detect one or more of the proteins disclosed or incorporated by reference herein.

ELISA is a heterogeneous immunoassay, which can be used in the methods disclosed herein. The assay can be used to detect protein antigens in various formats. In the "sandwich" format the antigen being assayed is held between two different antibodies. In this method, a solid surface is first coated with a solid phase antibody. The test sample, containing the antigen (e.g., a diagnostic protein), or a composition containing the antigen, such as a synovial fluid sample from a subject of interest, is then added and the antigen is allowed to react with the bound antibody. Any unbound antigen is washed away. A known amount of enzyme-labeled antibody is then allowed to react with the bound antigen. Any excess unbound enzyme-linked antibody is washed away after the reaction. The substrate for the enzyme used in the assay is then added and the reaction between the substrate and the enzyme produces a color change. The amount of visual color change is a direct measurement of specific enzyme-conjugated bound antibody, and consequently the antigen present in the sample tested.

ELISA can also be used as a competitive assay. In the competitive assay format, the test specimen containing the antigen to be determined is mixed with a precise amount of enzyme-labeled antigen and both compete for binding to an anti-antigen antibody attached to a solid surface. Excess free enzyme-labeled antigen is washed off before the substrate for the enzyme is added. The amount of color intensity resulting from the enzyme-substrate interaction is a measure of the amount of antigen in the sample tested. A heterogeneous immunoassay, such as an ELISA, can be used to detect any of the proteins disclosed or incorporated by reference herein.

Homogeneous immunoassays include, for example, the Enzyme Multiplied Immunoassay Technique (EMIT), which typically includes a biological sample comprising the biomarkers to be measured, enzyme-labeled molecules of the biomarkers to be measured, specific antibody or antibodies binding the biomarkers to be measured, and a specific enzyme chromogenic substrate. In a typical EMIT, excess of specific antibodies is added to a biological sample. If the biological sample contains the proteins to be detected, such proteins bind to the antibodies. A measured amount of the corresponding enzyme-labeled proteins is then added to the mixture. Antibody binding sites not occupied by molecules of the protein in the sample are occupied with molecules of the added enzyme-labeled protein. As a result, enzyme activity is reduced because only free enzyme-labeled protein can act on the substrate. The amount of substrate converted from a colorless to a colored form determines the amount of free enzyme left in the mixture. A high concentration of the protein to be detected in the sample causes higher absorbance readings. Less protein in the sample results in less enzyme activity and consequently lower absorbance readings. Inactivation of the enzyme label when the antigen-enzyme complex is antibody-bound makes the EMIT a useful system, enabling the test to be performed without a separation of bound from unbound compounds as is necessary with other immunoassay methods. A homogenous immunoassay, such as an EMIT, can be used to detect any of the proteins disclosed or incorporated by reference herein.

In many immunoassays, as described elsewhere herein, detection of antigen is made with the use of antigens specific antibodies as detector molecules. However, immunoassays and the systems and methods of the present invention are not limited to the use of antibodies as detector molecules. Any substance that can bind or capture the antigen within a given sample may be used. Aside from antibodies, suitable substances that can also be used as detector molecules include but are not limited to enzymes, peptides, proteins, and nucleic acids. Further, there are many detection methods known in the art in which the captured antigen may be detected. In some assays, enzyme-linked antibodies produce a color change. In other assays, detection of the captured antigen is made through detecting fluorescent, luminescent, chemiluminescent, or radioactive signals. The system and methods of the current invention is not limited to the particular types of detectable signals produced in an immunoassay.

Immunoassay kits are also included in the invention. These kits include, in separate containers (a) monoclonal antibodies having binding specificity for the polypeptides used in the diagnosis of inflammation or the source of inflammation; and (b) and anti-antibody immunoglobulins. This immunoassay kit may be utilized for the practice of the various methods provided herein. The monoclonal antibodies and the anti-antibody immunoglobulins can be provided in an amount of about 0.001 mg to 100 grams, and more preferably about 0.01 mg to 1 gram. The anti-antibody immunoglobulin may be a polyclonal immunoglobulin, protein A or protein G or functional fragments thereof, which may be labeled prior to use by methods known in the art. In several embodiments, the immunoassay kit includes two, three or four of: antibodies that specifically bind a protein disclosed or incorporated herein.

In one embodiment, the immunoassay kit of the invention can comprise (a) a sample pad, (b) a conjugated label pad, the conjugated label pad having a detectable label, a portion of the conjugated label pad and a portion of the sample pad forming a first interface, (c) a lateral-flow assay comprising a membrane, a portion of the membrane and a portion of the conjugated label pad forming a second interface, and (d) at least one antibody bound to the membrane, the first interface allowing fluid to flow from the sample pad to the conjugated label pad and contact the detectable label wherein the biomarker present in the sample forms an biomarker-conjugated label complex, the second interface allowing fluid to flow from the conjugated label pad to the membrane and to contact the at least one membrane-bound antibody to form to an biomarker-antibody complex and cause the detectable label to form a detectable signal.

Biosensors

In one embodiment, the biomarkers of the invention are detected using biosensors, e.g. with sensor systems with amperometric, electrochemical, potentiometric, conductimetric, impedance, magnetic, optical, acoustic or thermal transducers.

Generally, biosensors include a biosensor recognition element which can include proteins, nucleic acids, antibodies, etc. that bind to a particular biomarker and a transducer which converts a molecular signal (i.e. binding of biomarker to recognition element) into an electric or digital signal that can be quantified, displayed, and analyzed. Biosensors may also include a reader device which translates the signal into a user-friendly display of the results. Examples of potential components that comprise an exemplary biosensor are described in Bohunicky et al. (2011, Nanotechnology Science and Applications, 4: 1-10), which is hereby incorporated by reference in its entirety.

A biosensor may incorporate a physical, chemical or biological detection system. In one embodiment, a biosensor is a sensor with a biological recognition system, e.g. based on a nucleic acid, such as an oligonucleotide probe or aptamer, or a protein such as an enzyme, binding protein, receptor protein, transporter protein or antibody. In one embodiment, the biological recognition system may comprise traditional immunoassays described elsewhere herein. In another element, the recognition element (e.g. protein, nucleic acid, antibody, etc.) may be unlabeled and binding of the biomarker to the element is directly observed and converted into a signal by the transducer.

The method for detection of the biomarker in a biosensor may comprise immunological, electrical, thermal, magnetic, optical (e.g. hologram) or acoustic technologies. Using such biosensors, it is possible to detect the target biomarker at the anticipated concentrations found in biological samples.

The biosensor may incorporate detection methods and systems as described herein for detection of the biomarker. Biosensors may employ electrical (e.g. amperometric, potentiometric, conductimetric, or impedance detection systems), calorimetric (e.g. thermal), magnetic, optical (e.g. hologram, luminescence, fluorescence, colorimetry), or mass change (e.g. piezoelectric, acoustic wave) technologies. In a biosensor according to the invention the level of one, two, three, or more biomarkers can be detected by one or more methods selected from: direct, indirect or coupled enzymatic, spectrophotometric, fluorimetric, luminometric, spectrometric, polarimetric and chromatographic techniques. Particularly preferred biosensors comprise one or more enzymes used directly or indirectly via a mediator, or using a binding, receptor or transporter protein, coupled to an electrical, optical, acoustic, magnetic or thermal transducer. Using such biosensors, it is possible to detect the level of target biomarkers at the anticipated concentrations found in biological samples.

In one embodiment of a biosensor, a biomarker of the invention can be detected using a biosensor incorporating technologies based on "smart" holograms, or high frequency acoustic systems, such systems are particularly amenable to "bar code" or array configurations. In smart hologram sensors (Smart Holograms Ltd, Cambridge, UK), a holographic image is stored in a thin polymer film that is sensitized to react specifically with the biomarker. On exposure, the biomarker reacts with the polymer leading to an alteration in the image displayed by the hologram. The test result readout can be a change in the optical brightness, image, color and/or position of the image. For qualitative and semi-quantitative applications, a sensor hologram can be read by eye, thus removing the need for detection equipment. A simple color sensor can be used to read the signal when quantitative measurements are required. Opacity or color of the sample does not interfere with operation of the sensor. The format of the sensor allows multiplexing for simultaneous detection of several substances. Reversible and irreversible sensors can be designed to meet different requirements, and continuous monitoring of a particular biomarker of interest is feasible.

Biosensors to detect the biomarker of the invention may include acoustic, surface plasmon resonance, holographic and microengineered sensors. Imprinted recognition elements, thin film transistor technology, magnetic acoustic resonator devices and other novel acousto-electrical systems may be employed in biosensors for detection of the biomarkers of the invention.

Suitably, biosensors for detection of the biomarker of the invention are coupled, i.e. they combine biomolecular recognition with appropriate means to convert detection of the presence, or quantitation, of the biomarker in the sample into a signal. Biosensors can be adapted for "alternate site" diagnostic testing, e.g. in the ward, outpatients' department, surgery, home, field and workplace.

Methods involving detection and/or quantification of the biomarker of the invention can be performed using benchtop instruments, or can be incorporated onto disposable, diagnostic or monitoring platforms that can be used in a non-laboratory environment, e.g. in the physician's office or at the patient's bedside.

Mass Spectrometry and Chromatography

In one embodiment, the systems and methods of the invention can be performed in the form of various mass spectrometry (MS) or chromatography formats, which are well known in the art. As such, the levels of biomarkers present in a sample can be determined by mass spectrometry. Generally, any mass spectrometric techniques that can obtain precise information on the mass of peptides, and preferably also on fragmentation and/or (partial) amino acid sequence of selected peptides, are useful herein. Suitable peptide MS techniques and systems are well-known per se (see, e.g., Methods in Molecular Biology, vol. 146: "Mass Spectrometry of Proteins and Peptides", by Chapman, ed., Humana Press 2000, ISBN 089603609x; Biemann 1990. Methods Enzymol 193: 455-79; or Methods in Enzymology, vol. 402: "Biological Mass Spectrometry", by Burlingame, ed., Academic Press 2005, ISBN 9780121828073) and may be used herein.

The terms "mass spectrometry" or "MS" as used herein refer to methods of filtering, detecting, and measuring ions based on their mass-to-charge ratio, or "m/z." In general, one or more molecules of interest are ionized, and the ions are subsequently introduced into a mass spectrographic instrument where, due to a combination of magnetic and electric fields, the ions follow a path in space that is dependent upon mass ("m") and charge ("z"). For examples see U.S. Pat. Nos. 6,204,500, 6,107,623, 6,268,144, 6,124,137; Wright et al., 1999, Prostate Cancer and Prostatic Diseases 2: 264-76; Merchant et al., 2000, Electrophoresis 21: 1164-67, each of which is hereby incorporated by reference in its entirety, including all tables, figures, and claims. Mass spectrometry methods are well known in the art and have been used to quantify and/or identify biomolecules, such as proteins and hormones (Li et al., 2000, Tibtech. 18:151-160; Starcevic et. al., 2003, J. Chromatography B, 792: 197-204; Kushnir et. al., 2006, Clin. Chem. 52:120-128; Rowley et al., 2000, Methods 20: 383-397; Kuster et al., 1998, Curr. Opin. Structural Biol. 8: 393-400). Further, mass spectrometric techniques have been developed that permit at least partial de novo sequencing of isolated proteins (Chait et al., 1993, Science, 262:89-92; Keough et al., 1999, Proc. Natl. Acad. Sci. USA. 96:7131-6; Bergman, 2000, EXS 88:133-44). Various methods of ionization are known in the art. For examples, Atmospheric Pressure Chemical Ionization (APCI) Chemical Ionization (CI) Electron Impact (EI) Electrospray Ionization (ESI) Fast Atom Bombardment (FAB) Field Desorption/Field Ionization (FD/FI) Matrix Assisted Laser Desorption Ionization (MALDI) and Thermospray Ionization (TSP).

The levels of biomarkers present in a sample can be determined by MS such as matrix-assisted laser desorption/ionization time-of-flight (MALDI-TOF) MS; MALDI-TOF post-source-decay (PSD); MALDI-TOF/TOF; surface-enhanced laser desorption/ionization time-of-flight mass spectrometry (SELDI-TOF) MS; tandem mass spectrometry (e.g., MS/MS, MS/MS/MS etc.); electrospray ionization mass spectrometry (ESI-MS); ESI-MS/MS; ESI-MS/(MS)n (n is an integer greater than zero); ESI 3D or linear (2D) ion trap MS; ESI triple quadrupole MS; ESI quadrupole orthogonal TOF (Q-TOF); ESI Fourier transform MS systems; desorption/ionization on silicon (DIOS); secondary ion mass spectrometry (SIMS); atmospheric pressure chemical ionization mass spectrometry (APCI-MS); APCI-MS/MS; APCI-(MS)$^n$; atmospheric pressure photoionization mass spectrometry (APPI-MS); APPI-MS/MS; APPI-(MS)$^n$; liquid chromatography-mass spectrometry (LC-MS), gas chromatography-mass spectrometry (GC-MS); high performance liquid chromatography-mass spectrometry (HPLC-MS); capillary electrophoresis-mass spectrometry; and nuclear magnetic resonance spectrometry. Peptide ion fragmentation in tandem MS (MS/MS) arrangements may be achieved using manners established in the art, such as, e.g., collision induced dissociation (CID). See for example, U.S. Patent Application Nos: 20030199001, 20030134304, 20030077616, which are herein incorporated by reference in their entirety. Such techniques may be used for relative and absolute quantification and also to assess the ratio of the biomarker according to the invention with other biomarkers that may be present. These methods are also suitable for clinical screening, prognosis, monitoring the results of therapy, identifying patients most likely to respond to a particular therapeutic treatment, for drug screening and development, and identification of new targets for drug treatment.

In certain embodiments, a gas phase ion spectrophotometer is used. In other embodiments, laser-desorption/ionization mass spectrometry is used to analyze the sample. Modern laser desorption/ionization mass spectrometry ("LDI-MS") can be practiced in two main variations: matrix assisted laser desorption/ionization ("MALDI") mass spectrometry and surface-enhanced laser desorption/ionization ("SELDI"). In MALDI, the analyte is mixed with a solution containing a matrix, and a drop of the liquid is placed on the surface of a substrate. The matrix solution then co-crystallizes with the biological molecules. The substrate is inserted into the mass spectrometer. Laser energy is directed to the substrate surface where it desorbs and ionizes the biological molecules without significantly fragmenting them. See, e.g., U.S. Pat. No. 5,118,937, and U.S. Pat. No. 5,045,694. In SELDI, the substrate surface is modified so that it is an active participant in the desorption process. In one variant, the surface is derivatized with adsorbent and/or capture reagents that selectively bind the biomarker of interest. In another variant, the surface is derivatized with energy absorbing molecules that are not desorbed when struck with the laser. In another variant, the surface is derivatized with molecules that bind the protein of interest and that contain a photolytic bond that is broken upon application of the laser. SELDI is a powerful tool for identifying a characteristic "fingerprint" of proteins and peptides in body fluids and tissues for a given condition, e.g. drug treatments and diseases. This technology utilizes protein chips to capture proteins/peptides and a time-of-flight mass spectrometer (tof-MS) to quantitate and calculate the mass of compounds ranging from small molecules and peptides of less than 1,000 Da up to proteins of 500 kDa. Quantifiable differences in protein/peptide patterns can be statistically evaluated using automated computer programs which represent each protein/peptide measured in the biofluid spectrum as a coordinate in multi-dimensional space. The SELDI system also has a capability of running hundreds of samples in a single experiment. In addition, all the signals from SELDI mass spectrometry are derived from native proteins/peptides (unlike some other proteomics technologies which require protease digestion), thus directly reflecting the underlying physiology of a given condition.

In MALDI and SELDI, the derivatizing agent generally is localized to a specific location on the substrate surface where the sample is applied. See, e.g., U.S. Pat. No. 5,719,060 and WO 98/59361. The two methods can be combined by, for example, using a SELDI affinity surface to capture an analyte and adding matrix-containing liquid to the captured analyte to provide the energy absorbing material. For additional information regarding mass spectrometers, see, e.g., Principles of Instrumental Analysis, 3rd edition., Skoog, Saunders College Publishing, Philadelphia, 1985; and Kirk-Othmer Encyclopedia of Chemical Technology, 4th ed. Vol. 15 (John Wiley & Sons, New York 1995), pp. 1071-1094. Detection and quantification of the biomarker will typically depend on the detection of signal intensity. For example, in certain embodiments, the signal strength of peak values from spectra of a first sample and a second sample can be compared (e.g., visually, by computer analysis etc.), to determine the relative amounts of particular biomarker. Software programs such as the Biomarker Wizard program (Ciphergen Biosystems, Inc., Fremont, Calif.) can be used to aid in analyzing mass spectra. The mass spectrometers and their techniques are well known to those of skill in the art.

In an embodiment, detection and quantification of biomarkers by mass spectrometry may involve multiple reaction monitoring (MRM), such as described among others by Kuhn et al. 2004 (Proteomics 4: 1175-86).

In an embodiment, MS peptide analysis methods may be advantageously combined with upstream peptide or protein separation or fractionation methods, such as for example with the chromatographic and other methods described herein below.

Chromatography can also be used for measuring biomarkers. As used herein, the term "chromatography" encompasses methods for separating chemical substances, referred to as such and vastly available in the art. In a preferred approach, chromatography refers to a process in which a mixture of chemical substances (analytes) carried by a moving stream of liquid or gas ("mobile phase") is separated into components as a result of differential distribution of the analytes, as they flow around or over a stationary liquid or solid phase ("stationary phase"), between said mobile phase and said stationary phase. The stationary phase may be usually a finely divided solid, a sheet of filter material, or a thin film of a liquid on the surface of a solid, or the like. Chromatography is also widely applicable for the separation of chemical compounds of biological origin, such as, e.g., amino acids, proteins, fragments of proteins or peptides, etc.

Chromatography as used herein may be preferably columnar (i.e., wherein the stationary phase is deposited or packed in a column), preferably liquid chromatography, and yet more preferably high-performance liquid chromatograph? (HPLC). While particulars of chromatography are well known in the art, for further guidance see, e.g., Meyer M., 1998, ISBN: 047198373X, and "Practical HPLC Methodology and Applications", Bidlingmeyer, B. A., John Wiley & Sons Inc., 1993.

Exemplary types of chromatography include, without limitation, HPLC, normal phase HPLC (NP-HPLC), reversed phase HPLC (RP-HPLC), ion exchange chromatography (IEC), such as cation or anion exchange chromatography, hydrophilic interaction chromatography (HILIC), hydrophobic interaction chromatography (HIC), size exclusion chromatography (SEC) including gel filtration chromatography or gel permeation chromatography, chromatofocusing, affinity chromatography such as immuno-affinity, immobilized metal affinity chromatography, and the like.

In an embodiment, chromatography, including single-, two- or more-dimensional chromatography, may be used as a peptide fractionation method in conjunction with a further peptide analysis method, such as for example, with a downstream mass spectrometry analysis as described elsewhere in this specification.

Further peptide or polypeptide separation, identification or quantification methods may be used, optionally in conjunction with any of the above described analysis methods, for measuring biomarkers in the present disclosure. Such methods include, without limitation, chemical extraction partitioning, isoelectric focusing (IEF) including capillary isoelectric focusing (CIEF), capillary isotachophoresis (CITP), capillary electrochromatography (CEC), and the like, one-dimensional polyacrylamide gel electrophoresis (PAGE), two-dimensional polyacrylamide gel electrophoresis (2D-PAGE), capillary gel electrophoresis (CGE), capillary zone electrophoresis (CZE), micellar electrokinetic chromatography (MEKC), free flow electrophoresis (FFE), etc.

Point-of-Use Devices

Point-of-use analytical tests have been developed for the routine identification or monitoring of health-related conditions (such as pregnancy, cancer, endocrine disorders, infectious diseases or drug abuse) using a variety of biological samples (such as urine, serum, plasma, blood, saliva). Some of the point-of-use assays are based on highly specific interactions between specific binding pairs, such as antigen/antibody, hapten/antibody, lectin/carbohydrate, apoprotein/cofactor and biotin/(strept)avidin. In some point-of use devices, assays are performed with test strips in which a specific binding pair member is attached to a mobilizable material (such as a metal sol or beads made of latex or glass) or an immobile substrate (such as glass fibers, cellulose strips or nitrocellulose membranes). Other point-of use devices may comprise optical biosensors, photometric biosensors, electrochemical biosensor, or other types of biosensors. Suitable biosensors in point-of-use devices for performing methods of the invention include "cards" or "chips" with optical or acoustic readers. Biosensors can be configured to allow the data collected to be electronically transmitted to the physician for interpretation and thus can form the basis for e-medicine, where diagnosis and monitoring can be done without the need for the patient to be in proximity to a physician or a clinic.

Detection of a biomarker in a synovial fluid can be carried out using a sample capture device, such as a lateral flow device (for example a lateral flow test strip) that allows detection of one or more biomarkers, such as those described herein. The test strips of the present invention include a flow path from an upstream sample application area to a test site. For example, the flow path can be from a sample application area through a mobilization zone to a capture zone. The mobilization zone may contain a mobilizable marker that interacts with an analyte or analyte analog, and the capture zone contains a reagent that binds the analyte or analyte analog to detect the presence of an analyte in the sample.

Examples of migration assay devices, which usually incorporate within them reagents that have been attached to colored labels, thereby permitting visible detection of the assay results without addition of further substances are found, for example, in U.S. Pat. No. 4,770,853 (incorporated herein by reference). There are a number of commercially available lateral-flow type tests and patents disclosing methods for the detection of large analytes (MW greater than 1,000 Daltons) as the analyte flows through multiple zones on a test strip. Examples are found in U.S. Pat. Nos. 5,229,073; 5,591,645; 4,168,146; 4,366,241; 4,855,240; 4,861,711; 5,120,643 (each of which are herein incorporated by reference). Multiple zone lateral flow test strips are disclosed in U.S. Pat. Nos. 5,451,504, 5,451,507, and U.S. Pat. No. 5,798,273 (incorporated by reference herein). U.S. Pat. No. 6,656,744 (incorporated by reference) discloses a lateral flow test strip in which a label binds to an antibody through a streptavidin-biotin interaction.

Flow-through type assay devices were designed, in part, to obviate the need for incubation and washing steps associated with dipstick assays. Flow-through immunoassay devices involve a capture reagent (such as one or more antibodies) bound to a porous membrane or filter to which a liquid sample is added. As the liquid flows through the membrane, target analyte (such as protein) binds to the capture reagent. The addition of sample is followed by (or made concurrent with) addition of detector reagent, such as labeled antibody (e.g., gold-conjugated or colored latex particle-conjugated protein). Alternatively, the detector reagent may be placed on the membrane in a manner that permits the detector to mix with the sample and thereby label the analyte. The visual detection of detector reagent provides an indication of the presence of target analyte in the sample. Representative flow-through assay devices are described in U.S. Pat. Nos. 4,246,339; 4,277,560; 4,632,901; 4,812,293; 4,920,046; and 5,279,935; U.S. Patent Application Publication Nos. 20030049857 and 20040241876; and WO 08/030,546. Migration assay devices usually incorporate within them reagents that have been attached to colored labels, thereby permitting visible detection of the assay results without addition of further substances. See, for example, U.S. Pat. No. 4,770,853; PCT Publication No. WO 88/08534.

There are a number of commercially available lateral flow type tests and patents disclosing methods for the detection of large analytes (MW greater than 1,000 Daltons). U.S. Pat. No. 5,229,073 describes a semiquantitative competitive immunoassay lateral flow method for measuring plasma lipoprotein levels. This method utilizes a plurality of capture zones or lines containing immobilized antibodies to bind both the labeled and free lipoprotein to give a semi-quantitative result. In addition, U.S. Pat. No. 5,591,645 provides a chromatographic test strip with at least two portions. The first portion includes a movable tracer and the second portion includes an immobilized binder capable of binding to the analyte. Additional examples of lateral flow tests for large analytes are disclosed in the following patent documents: U.S. Pat. Nos. 4,168,146; 4,366,241; 4,855,240; 4,861,711; and 5,120,643; WO 97/06439; WO 98/36278; and WO 08/030,546.

Devices described herein generally include a strip of absorbent material (such as a microporous membrane), which, in some instances, can be made of different substances each joined to the other in zones, which may be abutted and/or overlapped. In some examples, the absorbent strip can be fixed on a supporting non-interactive material (such as nonwoven polyester), for example, to provide increased rigidity to the strip. Zones within each strip may differentially contain the specific binding partner(s) and/or other reagents required for the detection and/or quantification of the particular analyte being tested for, for example, one or more proteins disclosed herein. Thus these zones can be viewed as functional sectors or functional regions within the test device.

In general, a fluid sample is introduced to the strip at the proximal end of the strip, for instance by dipping or spotting. A sample is collected or obtained using methods well known to those skilled in the art. The sample containing the particular proteins to be detected may be obtained from any biological source. In a particular example, the biological source is synovial fluid. The sample may be diluted, purified, concentrated, filtered, dissolved, suspended or otherwise manipulated prior to assay to optimize the immunoassay results. The fluid migrates distally through all the functional regions of the strip. The final distribution of the fluid in the individual functional regions depends on the adsorptive capacity and the dimensions of the materials used.

In some embodiments, porous solid supports, such as nitrocellulose, described elsewhere herein are preferably in the form of sheets or strips. The thickness of such sheets or strips may vary within wide limits, for example, from about 0.01 to 0.5 mm, from about 0.02 to 0.45 mm, from about 0.05 to 0.3 mm, from about 0.075 to 0.25 mm, from about 0.1 to 0.2 mm, or from about 0.11 to 0.15 mm. The pore size of such sheets or strips may similarly vary within wide limits, for example from about 0.025 to 15 microns, or more specifically from about 0.1 to 3 microns; however, pore size is not intended to be a limiting factor in selection of the solid support. The flow rate of a solid support, where applicable, can also vary within wide limits, for example from about 12.5 to 90 sec/cm (i.e., 50 to 300 sec/4 cm), about 22.5 to 62.5 sec/cm (i.e., 90 to 250 sec/4 cm), about 25 to 62.5 sec/cm (i.e., 100 to 250 sec/4 cm), about 37.5 to 62.5 sec/cm (i.e., 150 to 250 sec/4 cm), or about 50 to 62.5 sec/cm (i.e., 200 to 250 sec/4 cm).

Another common feature to be considered in the use of assay devices is a means to detect the formation of a complex between an analyte (such as one or more proteins described herein) and a capture reagent (such as one or more antibodies). A detector (also referred to as detector reagent) serves this purpose. A detector may be integrated into an assay device (for example includes in a conjugate pad), or may be applied to the device from an external source.

A detector may be a single reagent or a series of reagents that collectively serve the detection purpose. In some instances, a detector reagent is a labeled binding partner specific for the analyte (such as a gold-conjugated antibody for a particular protein of interest).

In other instances, a detector reagent collectively includes an unlabeled first binding partner specific for the analyte and a labeled second binding partner specific for the first binding partner and so forth. Thus, the detector can be a labeled antibody specific for a protein described herein. The detector can also be an unlabeled first antibody specific for the protein of interest and a labeled second antibody that specifically binds the unlabeled first antibody. In each instance, a detector reagent specifically detects bound analyte of an analyte-capture reagent complex and, therefore, a detector reagent preferably does not substantially bind to or react with the capture reagent or other components localized in the analyte capture area. Such non-specific binding or reaction of a detector may provide a false positive result. Optionally, a detector reagent can specifically recognize a positive control molecule (such as a non-specific human IgG for a labeled Protein A detector, or a labeled Protein G detector, or a labeled anti-human Ab(Fc)) that is present in a secondary capture area.

Flow-Through Device Construction and Design

A flow-through device involves a capture reagent (such as one or more antibodies) immobilized on a solid support, typically, microtiter plate or a membrane (such as, nitrocellulose, nylon, or PVDF). In a simple representative format, the membrane of a flow-through device is placed in functional or physical contact with an absorbent layer, which acts as a reservoir to draw a fluid sample through the membrane. Optionally, following immobilization of a capture reagent, any remaining protein-binding sites on the membrane can be blocked (either before or concurrent with sample administration) to minimize nonspecific interactions.

In operation of a flow-through device, a fluid sample is placed in contact with the membrane. Typically, a flow-through device also includes a sample application area (or reservoir) to receive and temporarily retain a fluid sample of a desired volume. The sample passes through the membrane matrix. In this process, an analyte in the sample (such as one or more protein, for example, one or more proteins described herein) can specifically bind to the immobilized capture reagent (such as one or more antibodies). Where detection of an analyte-capture reagent complex is desired, a detector reagent (such as labeled antibodies that specifically bind one or more proteins) can be added with the sample or a solution containing a detector reagent can be added subsequent to application of the sample. If an analyte is specifically bound by capture reagent, a characteristic attributable to the particular detector reagent can be observed on the surface of the membrane. Optional wash steps can be added at any time in the process, for instance, following application of the sample, and/or following application of a detector reagent.

Lateral Flow Device Construction and Design

Lateral flow devices are commonly known in the art. Briefly, a lateral flow device is an analytical device having as its essence a test strip, through which flows a test sample fluid that is suspected of containing an analyte of interest. The test fluid and any suspended analyte can flow along the strip to a detection zone in which the analyte (if present) interacts with a capture agent and a detection agent to indicate a presence, absence and/or quantity of the analyte.

Numerous lateral flow analytical devices have been disclosed, and include those shown in U.S. Pat. Nos. 4,313,734; 4,435,504; 4,775,636; 4,703,017; 4,740,468; 4,806,311; 4,806,312; 4,861,711; 4,855,240; 4,857,453; 4,943,522; 4,945,042; 4,496,654; 5,001,049; 5,075,078; 5,126,241; 5,451,504; 5,424,193; 5,712,172; 6,555,390; 6,258,548; 6,699,722; 6,368,876 and 7,517,699, each of which is incorporated by reference.

Many lateral flow devices are one-step lateral flow assays in which a biological fluid is placed in a sample area on a bibulous strip (though non-bibulous materials can be used, and rendered bibulous, e.g., by applying a surfactant to the material), and allowed to migrate along the strip until the liquid comes into contact with a specific binding partner (such as an antibody) that interacts with an analyte (such as one or more proteins) in the liquid. Once the analyte interacts with the binding partner, a signal (such as a fluorescent or otherwise visible dye) indicates that the interaction has occurred. Multiple discrete binding partners (such as antibodies) can be placed on the strip (for example in parallel lines) to detect multiple analytes (such as two or more proteins) in the liquid. The test strips can also incorporate control indicators, which provide a signal that the test has adequately been performed, even if a positive signal indicating the presence (or absence) of an analyte is not seen on the strip.

Lateral flow devices have a wide variety of physical formats that are equally well known in the art. Any physical format that supports and/or houses the basic components of a lateral flow device in the proper function relationship is contemplated by this disclosure.

Figure 2:
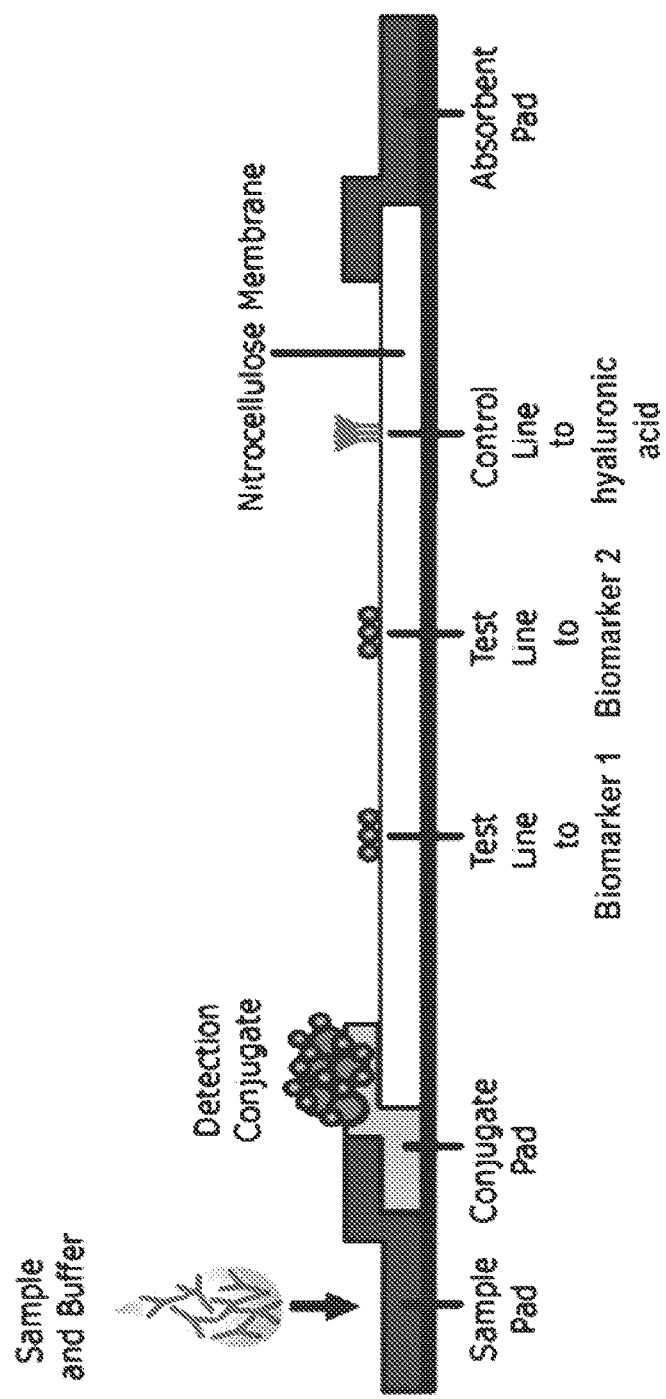
FIG. 2 is a schematic of an exemplary system for detecting a biomarker in a joint fluid. The image shows the basic components of the system and their relationship to each other. The system includes control line useful for the detection of hyaluronic acid in order to ensure that the sample tested is indeed synovial fluid.
Figure 3:
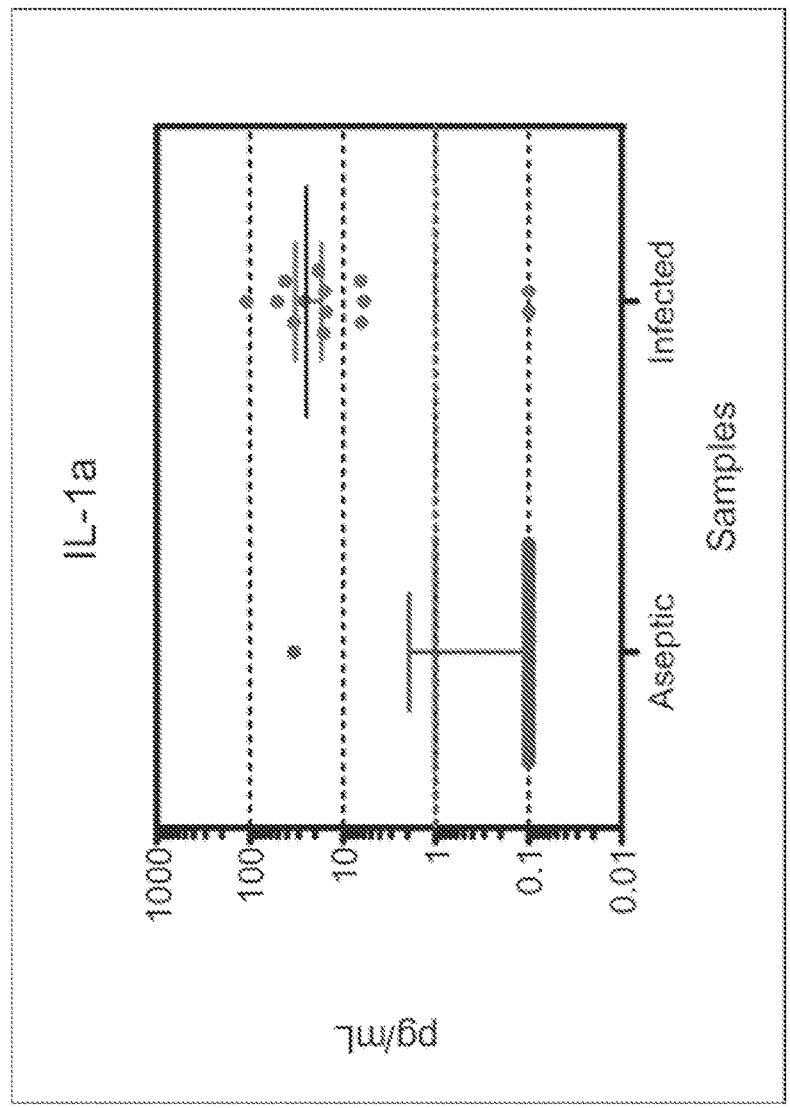
FIG. 3 is an image of a dot plot summarizing the ROC Analysis for Area Under the Curve (AUC) with respect to Interleukin-1α between infected and aseptic groups.
Figure 4:
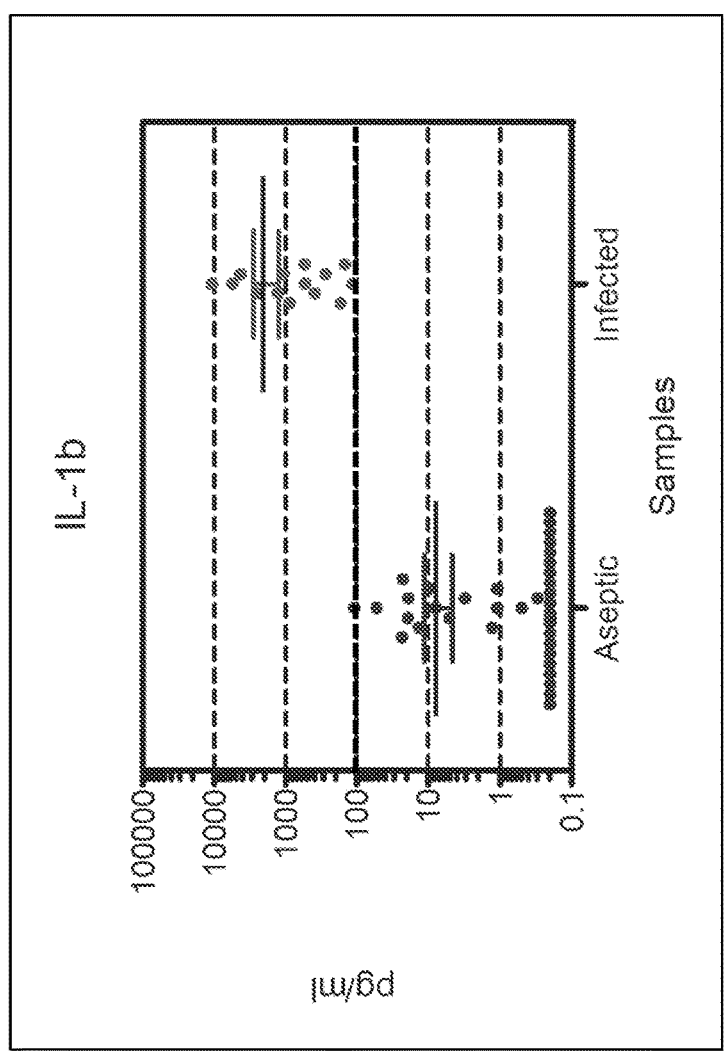
FIG. 4 is an image of a dot plot summarizing the ROC Analysis for Area Under the Curve (AUC) with respect to Interleukin-1β between infected and aseptic groups.
Figure 5:
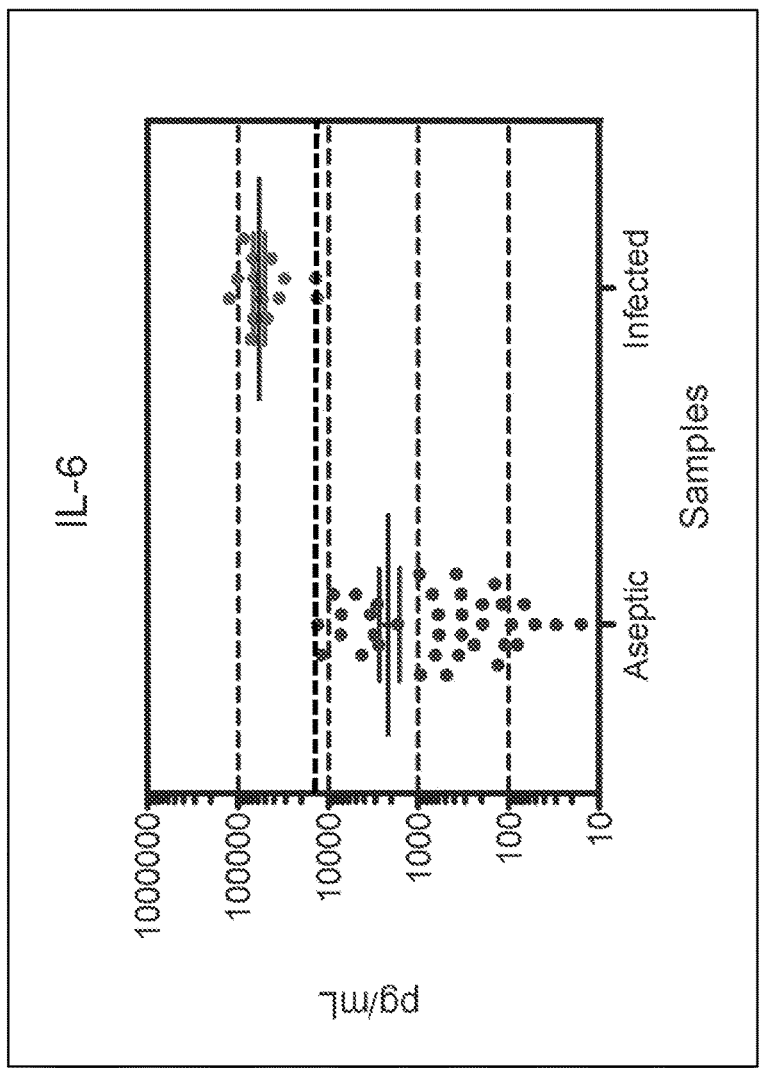
FIG. 5 is an image of a dot plot summarizing the ROC Analysis for Area Under the Curve (AUC) with respect to Interleukin-6 between infected and aseptic groups.
Figure 6:
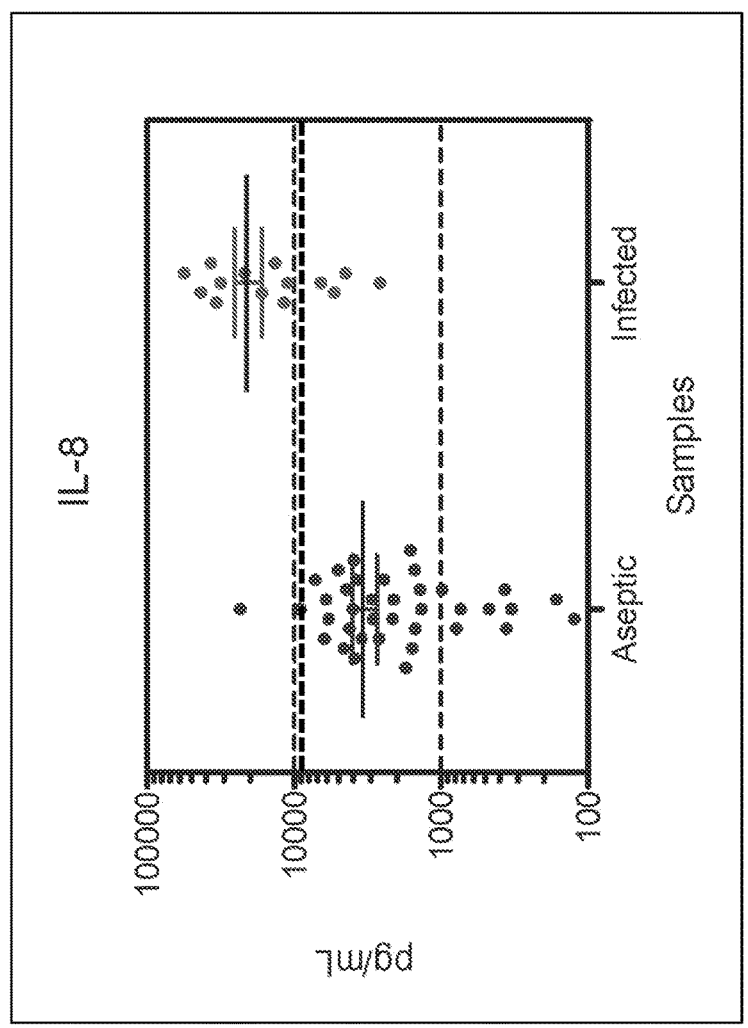
FIG. 6 is an image of a dot plot summarizing the ROC Analysis for Area Under the Curve (AUC) with respect to Interleukin-8 between infected and aseptic groups.
Figure 7:
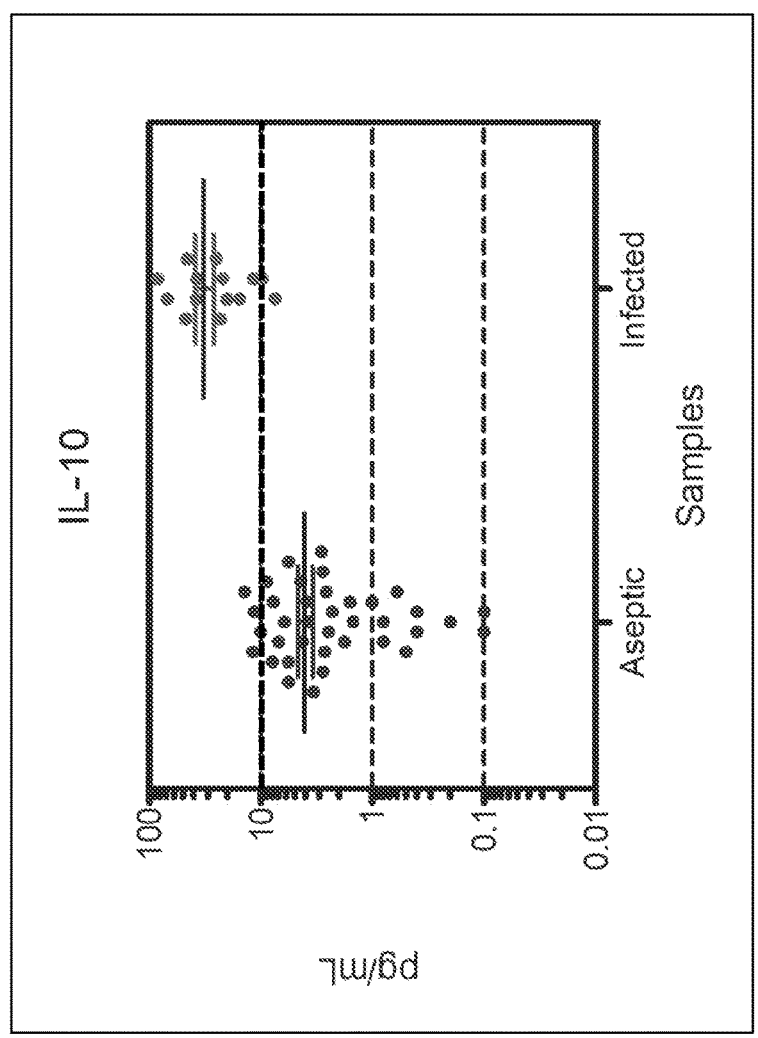
FIG. 7 is an image of a dot plot summarizing the ROC Analysis for Area Under the Curve (AUC) with respect to Interleukin-10 between infected and aseptic groups.
Figure 8:
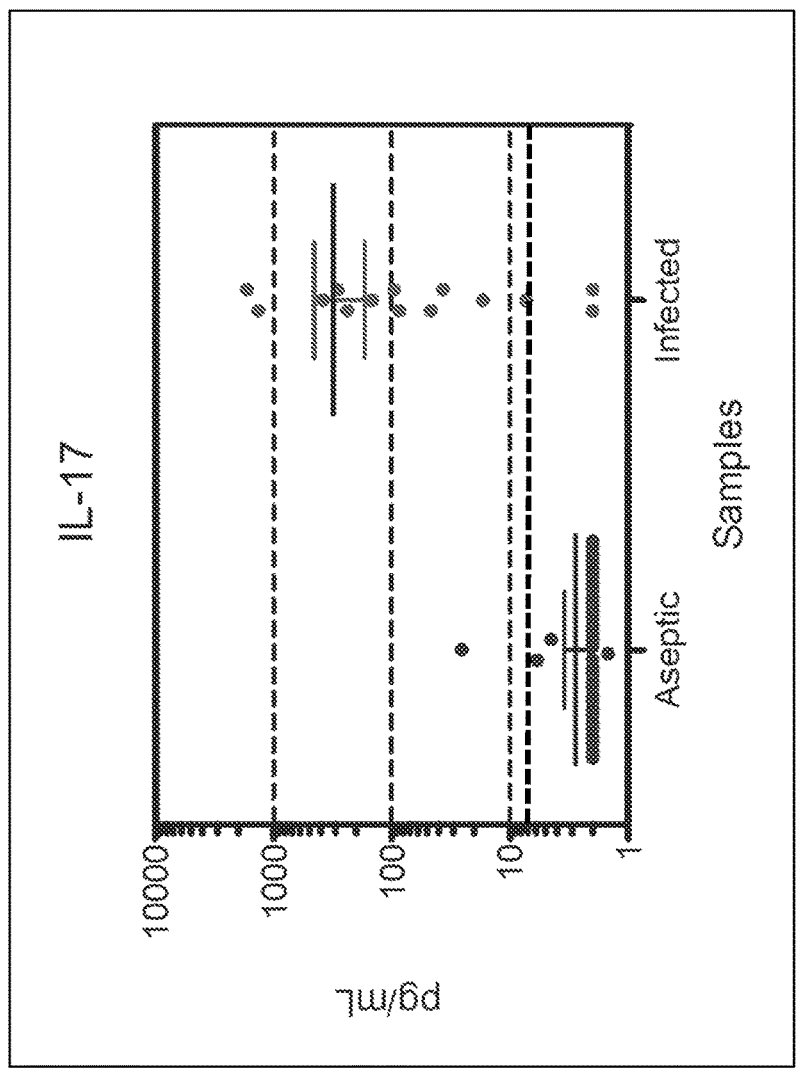
FIG. 8 is an image of a dot plot summarizing the ROC Analysis for Area Under the Curve (AUC) with respect to Interleukin-17 between infected and aseptic groups.
Figure 9:
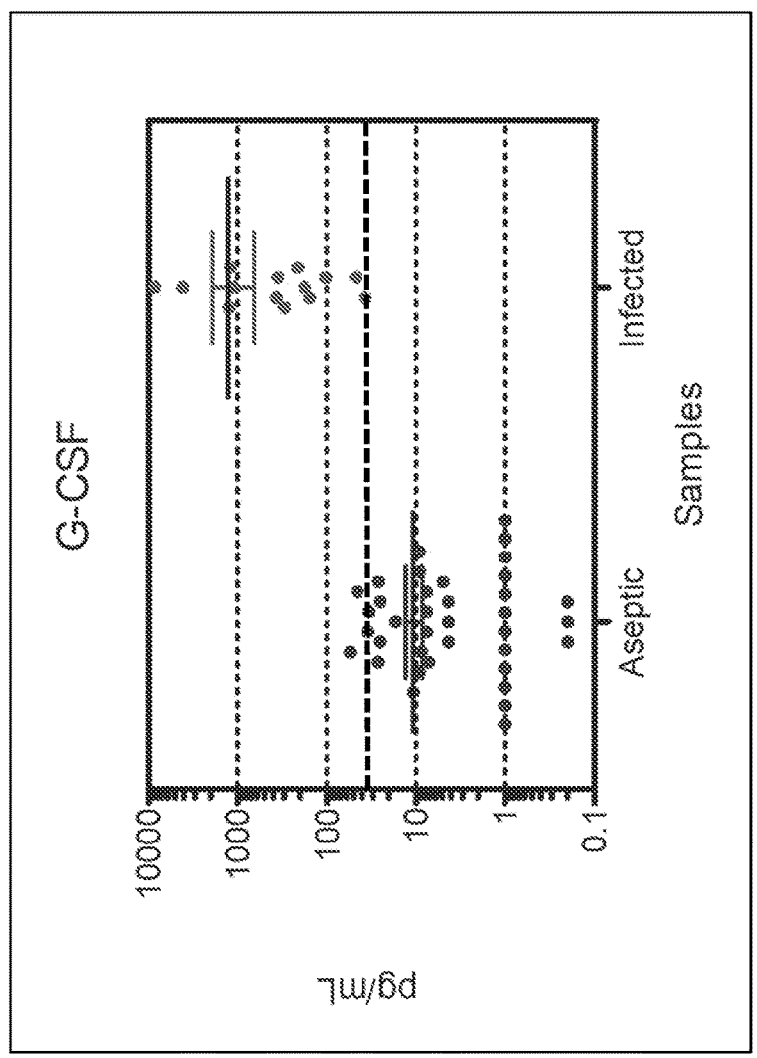
FIG. 9 is an image of a dot plot summarizing the ROC Analysis for Area Under the Curve (AUC) with respect to G-CSF between infected and aseptic groups.
Figure 10:
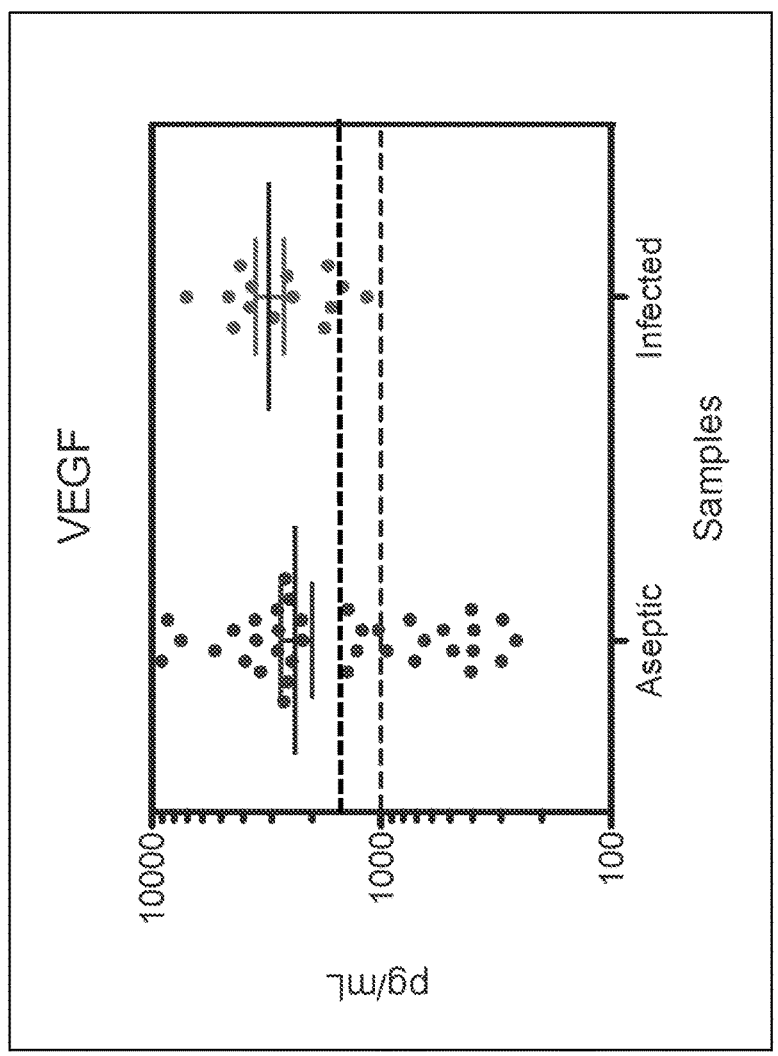
FIG. 10 is an image of a dot plot summarizing the ROC Analysis for Area Under the Curve (AUC) with respect to VEGF between infected and aseptic groups.
Figure 11:
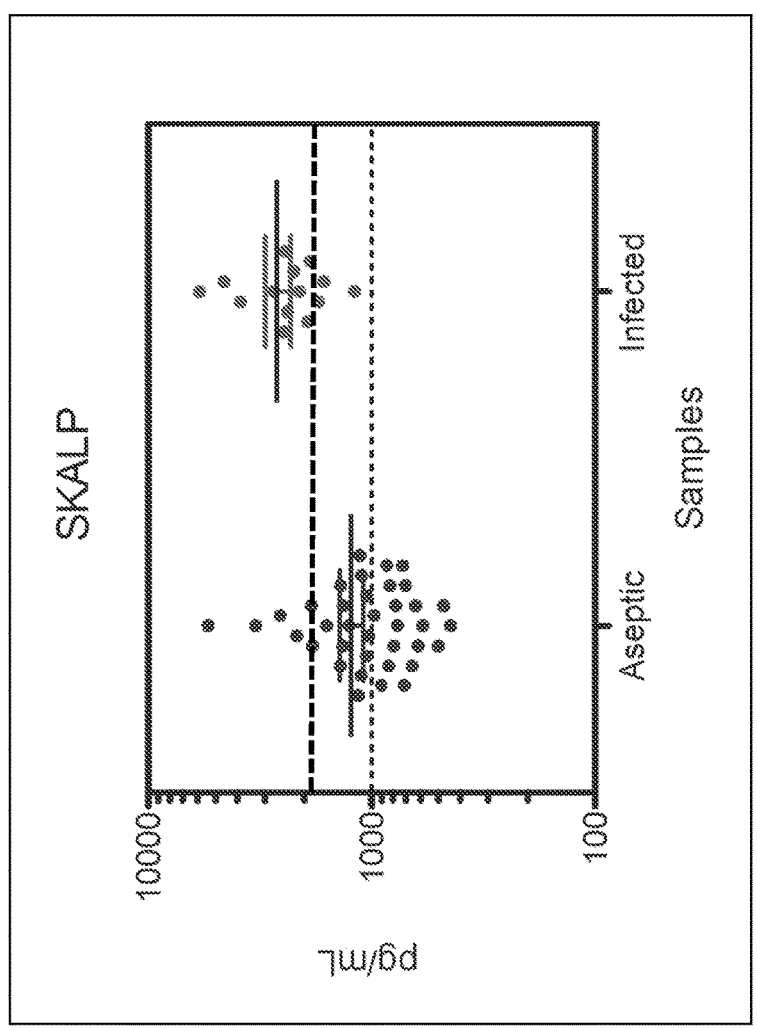
FIG. 11 is an image of a dot plot summarizing the ROC Analysis for Area Under the Curve (AUC) with respect to SKALP between infected and aseptic groups.

The basic components of a particular embodiment of a lateral flow device are illustrated in FIGS. 1 and 2 which comprise a sample pad, a conjugate pad, a migration membrane, and an absorbent pad.

The sample pad (such as the sample pad in FIGS. 1 and 2) is a component of a lateral flow device that initially receives the sample, and may serve to remove particulates from the sample. Among the various materials that may be used to construct a sample pad (such as glass fiber, woven fibers, screen, non-woven fibers, cellosic fibers or paper) or a cellulose sample pad may be beneficial if a large bed volume is a factor in a particular application. Sample pads may be treated with one or more release agents, such as buffers, salts, proteins, detergents, and surfactants. Such release agents may be useful, for example, to promote resolubilization of conjugate-pad constituents, and to block non-specific binding sites in other components of a lateral flow device, such as a nitrocellulose membrane. Representative release agents include, for example, trehalose or glucose (1%-5%), PVP or PVA (0.5%-2%), Tween 20 or Triton X-100 (0.1%-1%), casein (1%-2%), SDS (0.02%-5%), and PEG (0.02%-5%).

With respect to the migration membrane, the types of membranes useful in a lateral flow device include but are not limited to nitrocellulose (including pure nitrocellulose and modified nitrocellulose) and nitrocellulose direct cast on polyester support, polyvinylidene fluoride, or nylon).

The conjugate pad (such as conjugate pad in FIGS. 1 and 2) serves to, among other things, hold a detector reagent. Suitable materials for the conjugate pad include glass fiber, polyester, paper, or surface modified polypropylene.

Detector reagent(s) contained in a conjugate pad is typically released into solution upon application of the test sample. A conjugate pad may be treated with various substances to influence release of the detector reagent into solution. For example, the conjugate pad may be treated with PVA or PVP (0.5% to 2%) and/or Triton X-100 (0.5%). Other release agents include, without limitation, hydroxypropylmethyl cellulose, SDS, Brij and β-lactose. A mixture of two or more release agents may be used in any given application.

With respect to the absorbent pad, the pad acts to increase the total volume of sample that enters the device. This increased volume can be useful, for example, to wash away unbound analyte from the membrane. Any of a variety of materials is useful to prepare an absorbent pad, for example, cellulosic filters or paper. In some device embodiments, an absorbent pad can be paper (i.e., cellulosic fibers). One of skill in the art may select a paper absorbent pad on the basis of, for example, its thickness, compressibility, manufacturability, and uniformity of bed volume. The volume uptake of an absorbent made may be adjusted by changing the dimensions (usually the length) of an absorbent pad.

In operation of the particular embodiment of a lateral flow device, a fluid sample containing an analyte of interest, such as one or more proteins described herein, is applied to the sample pad. In some examples, the sample may be applied to the sample pad by dipping the end of the device containing the sample pad into the sample (such as synovial) or by applying the sample directly onto the sample pad.

From the sample pad, the sample passes, for instance by capillary action, to the conjugate pad. In the conjugate pad, the analyte of interest, such as a protein of interest, may bind (or be bound by) a mobilized or mobilizable detector reagent, such as an antibody (such as antibody that recognizes one or more of the proteins described herein). For example, a protein analyte may bind to a labeled (e.g., gold-conjugated or colored latex particle-conjugated) antibody contained in the conjugate pad. The analyte complexed with the detector reagent may subsequently flow to the test line where the complex may further interact with an analyte-specific binding partner (such as an antibody that binds a particular protein, an anti-hapten antibody, or streptavidin), which is immobilized at the proximal test line. In some examples, a protein complexed with a detector reagent (such as gold-conjugated antibody) may further bind to unlabeled, oxidized antibodies immobilized at the proximal test line. The formation of a complex, which results from the accumulation of the label (e.g., gold or colored latex) in the localized region of the proximal test line, is detected. The control line may contain an immobilized, detector-reagent-specific binding partner, which can bind the detector reagent in the presence or absence of the analyte. Such binding at the control line indicates proper performance of the test, even in the absence of the analyte of interest.

In one embodiment, the control line detects the presence of hyaluronic acid which is a marker for synovial fluid in order to ensure that the test sample is indeed synovial fluid. Therefore, in this situation, the control line is formed by using antibodies to hyaluronic acid (FIG. 2). If the sample is obtained from anything other than the joint (i.e. blood), no line is formed and the test is deemed to be invalid.

The test results may be visualized directly, or may be measured using a reader (such as a scanner). The reader device may detect color, fluorescence, luminescence, radioactivity, or any other detectable marker derived from the labeled reagent from the readout area (for example, the test line and/or control line).

In another embodiment of a lateral flow device, there may be a second (or third, fourth, or more) test line located parallel or perpendicular (or in any other spatial relationship) to test line in test result zone (for example test lines to biomarker 1 and biomarker 2 in FIG. 2). The operation of this particular embodiment is similar to that described elsewhere herein with the additional considerations that (i) a second detector reagent specific for a second analyte, such as another antibody, may also be contained in the conjugate pad, and (ii) the second test line will contain a second specific binding partner having affinity for a second analyte, such as a second protein in the sample. Similarly, if a third (or more) test line is included, the test line will contain a third (or more) specific binding partner having affinity for a third (or more) analyte.

In one embodiment, a comparison of the control line to the test line yields the test result from the diagnostic system of the invention. In some instances, a valid result occurs when the control line is detected at a higher intensity level than the test line. For example, a valid result occurs when the control line is at least 5% or more, for example, 10%, 20%, 30%, 40%, 50%, 60%, 70%, 80%, 90%, 100% or more darker than the test line. In some instances, a valid result occurs when the control line is at least 0.5 fold or more, for example, 1 fold, 2 fold, 3 fold, 4 fold, 5 fold, 6 fold, 7 fold, 8 fold, 9 fold, 10 fold or more darker than the test line.

In one embodiment, the control line is a reference line that insures that the test has been run correctly and that the tested sample is not obtained from anything other than the joint (i.e. blood). For example, the system of the invention is useful in the diagnosis of infection in a joint when the control line is detected at an at least equal intensity than the test line. Preferably, the control line is detected at higher intensity than the test line. In some instances, if the test line is not at least equal in darkness or intensity as the control line then the test is said to have an invalid result. If the test line is at least equal or lighter than the control line then the test is said to have a valid result.

In one embodiment, the control line is a reference line that detects HA, wherein HA is a valid marker for distinguishing synovial fluid from other bodily fluids (e.g., blood). In some instances, HA is detected by using aggrecan to detect the difference between blood and synovial fluid. This is because aggrecan can effectively bind to HA.

Point of Care Diagnostic and Risk Assessment Systems

The system of the invention can be applied to a point-of-care scenario. U.S. Pat. Nos. 6,267,722, 6,394,952 and 6,867,051 disclose and describe systems for diagnosing and assessing certain medical risks, the contents of which are incorporated herein. The systems are designed for use on site at the point of care, where patients are examined and tested, as well as for operation remote from the site. The systems are designed to accept input in the form of patient data, including, but not limited to biochemical test data, physical test data, historical data and other such data, and to process and output information, such as data relating to a medical diagnosis or a disease risk indicator. The patient data may be contained within the system, such as medical records or history, or may be input as a signal or image from a medical test or procedure, for example, immunoassay test data, blood pressure reading, ultrasound, X-ray or MRI, or introduced in any other form. Specific test data can be digitized, processed and input into the medical diagnosis expert system, where it may be integrated with other patient information. The output from the system is a disease risk index or medical diagnosis.

Point of care testing refers to real time diagnostic testing that can be done in a rapid time frame so that the resulting test is performed faster than comparable tests that do not employ this system. For example, the exemplified immunoassay disclosed and described herein can be performed in significantly less time than the corresponding ELISA assay, e.g., in less than half an hour. In addition, point of care testing refers to testing that can be performed rapidly and on site, such as in a doctor's office, at a bedside, in a stat laboratory, emergency room or other such locales, particularly where rapid and accurate results are required.

In an exemplary embodiment, a point of care diagnostic and risk assessment system includes a reader for reading patient data, a test device designed to be read in the reader, and software for analysis of the data. A test strip device in a plastic housing is designed for use with the reader, optionally including a symbology, such as an alphanumeric character bar code or other machine-readable code, and software designed for analysis of the data generated from the test strip are also provided.

In one embodiment, a reader refers to an instrument for detecting and/or quantitating data, such as on test strips. The data may be visible to the naked eye, but does not need to be visible. Such readers are disclosed and described in the above-incorporated U.S. Pat. Nos. 6,267,722, 6,394,952 and 6,867,051. A reflectance reader refers to an instrument adapted to read a test strip using reflected light, including fluorescence, or electromagnetic radiation of any wavelength. Reflectance can be detected using a photodetector or other detector, such as charge coupled diodes (CCD). An exemplary reflectance reader includes a cassette slot adapted to receive a test-strip, light-emitting diodes, optical fibers, a sensing head, including means for positioning the sensing head along the test strip, a control circuit to read the photodetector output and control the on and off operation of the light-emitting diodes, a memory circuit for storing raw and/or processed data, and a photodetector, such as a silicon photodiode detector. It will be appreciated that a color change refers to a change in intensity or hue of color or may be the appearance of color where no color existed or the disappearance of color.

In one embodiment, a sample is applied to a diagnostic immunoassay test strip, and colored or dark bands are produced. The intensity of the color reflected by the colored label in the test region (or detection zone) of the test strip is, for concentration ranges of interest, directly proportional or otherwise correlated with an amount of analyte present in the sample being tested. The color intensity produced is read, in accordance with the present embodiment, using a reader device, for example, a reflectance reader, adapted to read the test strip. The intensity of the color reflected by the colored label in the test region (or detection zone) of the test strip is directly proportional to the amount of analyte present in the sample being tested. In other words, a darker colored line in the test region indicates a greater amount of analyte, whereas a lighter colored line in the test region indicates a smaller amount of analyte. The color intensity produced, i.e., the darkness or lightness of the colored line, is read using a reader device, for example, a reflectance reader, adapted to read the test strip.

A reflectance measurement obtained by the reader device is correlated to the presence and/or quantity of analyte present in the sample. The reader takes a plurality of readings along the strip, and obtains data that are used to generate results that are an indication of the presence and/or quantity of analyte present in the sample. The system may correlate such data with the presence of a disorder, condition or risk thereof.

As mentioned elsewhere herein, in addition to reading the test strip, the reader may (optionally) be adapted to read a symbology, such as a bar code, which is present on the test strip or housing and encodes information relating to the test strip device and/or test result and/or patient, and/or reagent or other desired information. Typically the associated information is stored in a remote computer database, but can be manually stored. Furthermore, the symbology can be imprinted when the device is used and the information encoded therein.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1: System for Detecting Biomarkers in Joint Fluid

Experiments were designed to develop a system for collecting and analyzing joint fluid in a simple and reproducible manner. Analysis of joint fluid is ideally suited for immunoassay. Unlike blood, which is the most commonly tested diagnostic sample, joint fluid does not circulate. Therefore, joint fluid presents a unique picture of what is happening in one specific location of the body (i.e. the joint). Being stationary also prevents dilution of targeted compounds which ensures that the concentration of the proteins is in a range easily measurable by immunoassay. Therefore, joint fluid (e.g., synovial fluid) can be used for the analysis of joint pain.

The system of the invention useful for analyzing joint fluid can be based on a lateral flow system. For example, the lateral flow immunoassay utilizes strips of cellulose membrane onto which antibodies and other reagents can be coated. The sample moves along the strip due to capillary action and reacts with the reagents at different points along the strip. The end result is usually the appearance or absence of a colored line or spot (FIG. 1). Because a lateral flow assay for biomarkers can be in the form of a sandwich assay, the signal results from the formation of an immunocomplex on the membrane.

The advantages of a lateral flow assay include quick results following application of the sample, no instrumentation is required, able to execute the test and read the result in the field itself, and allows for room temperature storage.

The system of the invention is useful for detecting biomarkers. Biomarkers are proteins or other cellular components that relate specifically to injury or to disease and that can be found in body fluids such as synovial fluid. A biomarker designates any indicatory (nucleic acids, enzymes, metabolites and other types of molecules: histamines, hormones, proteins, etc.) present in the body as a biological response to disease. The identification and development of biomarkers make it possible to perform faster, more accurate disease diagnostics and help physicians prescribe new treatments for those patients who are likely to benefit from them. Tests bases on biomarkers often contribute to a faster cure and avoid time-consuming and costly analyses.

To be specific for injury or disease, the presence of the biomarkers in the synovial fluid must depend on the diseased state and should not be present under normal conditions or in different disease states. The use of synovial fluid provides an optimum medium for the use of biomarkers in diagnosing, for example, the source of joint pain because joint fluid is a "closed" system. In an experiment where the concentrations of IL-6 in serum versus synovial fluid from patients with an infected knee were compared, a 1000× amplification in the synovial fluid was observed.

Unlike with the use of blood where the presence of a biomarker can be a result from anywhere in the body, the presence of a biomarker in synovial fluid is a result from a local response.

One of the concerns in sample collection is to ensure that the withdrawn sample is indeed synovial fluid. Therefore, in this situation, the control line is formed by using monoclonal antibodies to hyaluronic acid (FIG. 2). If the sample is from anything other than the joint (i.e. serum), no line is formed and the test is deemed invalid.

Example 2: Synovial Fluid Biomarkers for Periprosthetic Infection

Experiments were designed to evaluate biomarker data from a study of synovial fluid biomarkers for periprosthetic infection (Deirmangian C et al., 2010, Clin Orthop Relat Res 468:2017-2023) that appeared to discriminate between infected and aseptic groups. ROC Analysis for Area Under the Curve (AUC), which is a measure of the degree of separation between the clinical groups at various thresholds, was used to further evaluate the biomarker data. Without wishing to be bound by any particular theory, it is believed that the higher the AUC value, the better the discrimination between the 2 clinical groups, and thereby indicating the predictiveness of the biomarker.

A ROC analysis for selected biomarkers was performed using Prism 5 for Mac OS X. The data output was summarized in Tables 1-9 below and a dot plot for each selected biomarker in FIGS. 3-11, respectively.

TABLE 1

Interleukin-1α

| Parameter | Level |
|---|---|
| Cut-off (pg/mL) | 1.0 |
| Specificity (%) | 97.3 |
| Sensitivity (%) | 85.7 |
| NPV (%) | 94.7 |
| PPV (%) | 92.3 |
| AUC | 0.910 |
| 95% confidence interval | 0.796 to 1.024 |
| P value | <0.0001 |
| Mean of aseptic samples (pg/mL) | 1.0 |
| Mean of infected samples (pg/mL) | 24.9 |
| Fold elevation of infected from aseptic samples | 24.9 |

TABLE 2

Interleukin-1β

| Parameter | Level |
|---|---|
| Cut-off (pg/mL) | 112 |
| Specificity (%) | 100.0 |
| Sensitivity (%) | 100.0 |
| NPV (%) | 100.0 |
| PPV (%) | 100.0 |
| AUC | 1.000 |
| 95% confidence interval | 1.000 to 1.000 |
| P value | <0.0001 |
| Mean of aseptic samples (pg/mL) | 8.0 |
| Mean of infected samples (pg/mL) | 2067.2 |
| Fold elevation of infected from aseptic samples | 258.4 |

TABLE 3

Interleukin-6

| Parameter | Level |
|---|---|
| Cut-off (pg/mL) | 13350 |
| Specificity (%) | 100.0 |
| Sensitivity (%) | 100.0 |
| NPV (%) | 100.0 |
| PPV (%) | 100.0 |
| AUC | 1.000 |
| 95% confidence interval | 1.000 to 1.000 |
| P value | <0.0001 |
| Mean of aseptic samples (pg/mL) | 2171.7 |
| Mean of infected samples (pg/mL) | 59324.8 |
| Fold elevation of infected from aseptic samples | 27.3 |

TABLE 4

Interleukin-8

| Parameter | Level |
|---|---|
| Cut-off (pg/mL) | 8790 |
| Specificity (%) | 97.3 |
| Sensitivity (%) | 71.4 |
| NPV (%) | 90.0 |

TABLE 4-continued

Interleukin-8

| Parameter | Level |
|---|---|
| PPV (%) | 90.9 |
| AUC | 0.923 |
| 95% confidence interval | 0.842 to 1.004 |
| P value | <0.0001 |
| Mean of aseptic samples (pg/mL) | 3402.7 |
| Mean of infected samples (pg/mL) | 21238.8 |
| Fold elevation of infected from aseptic samples | 6.2 |

TABLE 5

Interleukin-10

| Parameter | Level |
|---|---|
| Cut-off (pg/mL) | 10.0 |
| Specificity (%) | 89.2 |
| Sensitivity (%) | 85.7 |
| NPV (%) | 94.3 |
| PPV (%) | 75.0 |
| AUC | 0.975 |
| 95% confidence interval | 0.939 to 1.011 |
| P value | <0.0001 |
| Mean of aseptic samples (pg/mL) | 4.1 |
| Mean of infected samples (pg/mL) | 32.6 |
| Fold elevation of infected from aseptic samples | 8.0 |

TABLE 6

Interleukin-17

| Parameter | Level |
|---|---|
| Cut-off (pg/mL) | 7.2 |
| Specificity (%) | 97.3 |
| Sensitivity (%) | 85.7 |
| NPV (%) | 94.7 |
| PPV (%) | 92.3 |
| AUC | 0.921 |
| 95% confidence interval | 0.810 to 1.032 |
| P value | <0.0001 |
| Mean of aseptic samples (pg/mL) | 2.8 |
| Mean of infected samples (pg/mL) | 314.6 |
| Fold elevation of infected from aseptic samples | 112.4 |

TABLE 7

G-CSF

| Parameter | Level |
|---|---|
| Cut-off (pg/mL) | 35.0 |
| Specificity (%) | 94.6 |
| Sensitivity (%) | 100.0 |
| NPV (%) | 100.0 |
| PPV (%) | 87.5 |
| AUC | 0.994 |
| 95% confidence interval | 0.981 to 1.007 |
| P value | <0.0001 |
| Mean of aseptic samples (pg/mL) | 10.7 |
| Mean of infected samples (pg/mL) | 1283.8 |
| Fold elevation of infected from aseptic samples | 120.0 |

TABLE 8

VEGF

| Parameter | Level |
|---|---|
| Cut-off (pg/mL) | 1500 |
| Specificity (%) | 48.6 |
| Sensitivity (%) | 85.7 |
| NPV (%) | 90.0 |
| PPV (%) | 61.3 |
| AUC | 0.677 |
| 95% confidence interval | 0.528 to 0.825 |
| P value | 0.0302 |
| Mean of aseptic samples (pg/mL) | 2374.5 |
| Mean of infected samples (pg/mL) | 3100.6 |
| Fold elevation of infected from aseptic samples | 1.3 |

TABLE 9

SKALP

| Parameter | Level |
|---|---|
| Cut-off (pg/mL) | 1880 |
| Specificity (%) | 89.2 |
| Sensitivity (%) | 78.6 |
| NPV (%) | 91.7 |
| PPV (%) | 73.3 |
| AUC | 0.900 |
| 95% confidence interval | 0.814 to 0.9855 |
| P value | <0.0001 |
| Mean of aseptic samples (pg/mL) | 1241.1 |
| Mean of infected samples (pg/mL) | 2650.7 |
| Fold elevation of infected from aseptic samples | 2.1 |

The results presented herein demonstrate that the AUC values for the selected biomarkers are high and show desirable discrimination between the 2 clinical groups. The results indicate that the predictiveness of these biomarkers is desirable.

Example 3: Pilot Assay for HNP1-3

The results presented herein demonstrate that HNP1-3 is a biomarker for infection in joint, preferably a replacement joint or periprosthetic joint.

The materials and methods employed in the experiments disclosed herein are now described.

Briefly, components were sourced from HYCULT® Biotech Human HNP1-3 Elisa Kit, catalog HK317. All reagents were brought to room temperature before use. Dilution buffer was prepared by mixing 10 ml of the 10× dilution buffer with 90 ml of deionized $H_2O$. As per the manufactures suggestion, the buffer mixture was allowed to sit for 10 minutes and inspected for crystals/particulate before being used. To make the standard/sample buffer, 90 ml of this dilution buffer was mixed with 10 ml of plasma diluent.

Synovial fluid and serum samples were diluted in sample buffer at both 1:100 and 1:1000. 100 ul of each standard or sample was then added to the assay plate as discussed elsewhere herein. The plate was covered and incubated at RT for 1 hour. The plate was then washed 3× using the biotek automated plate washer program "flat nunc plate" with in-house wash buffer of DPBS with 0.05% tween. This automated washer and wash buffer were used for all wash steps.

100 ul/well of the tracer solution was added, the plate covered, and the plate was then incubated at RT for 1 hour. The 3× wash procedure was repeated, then 100 ul/well of a streptavidin-peroxidase conjugate was added to the plate. The plate was sealed and incubated for 1 hour at RT. After washing 3×, 100 ul/well of TMB substrate was added. The plate was developed in the dark for 30 minutes, then stopped using a stop solution. The assay was then read at 450 nm absorbance using the SPECTRAMAX® plate reader with SOFTMAX® software.

The results of the experiments presented in this Example are now described.

Figure 12:
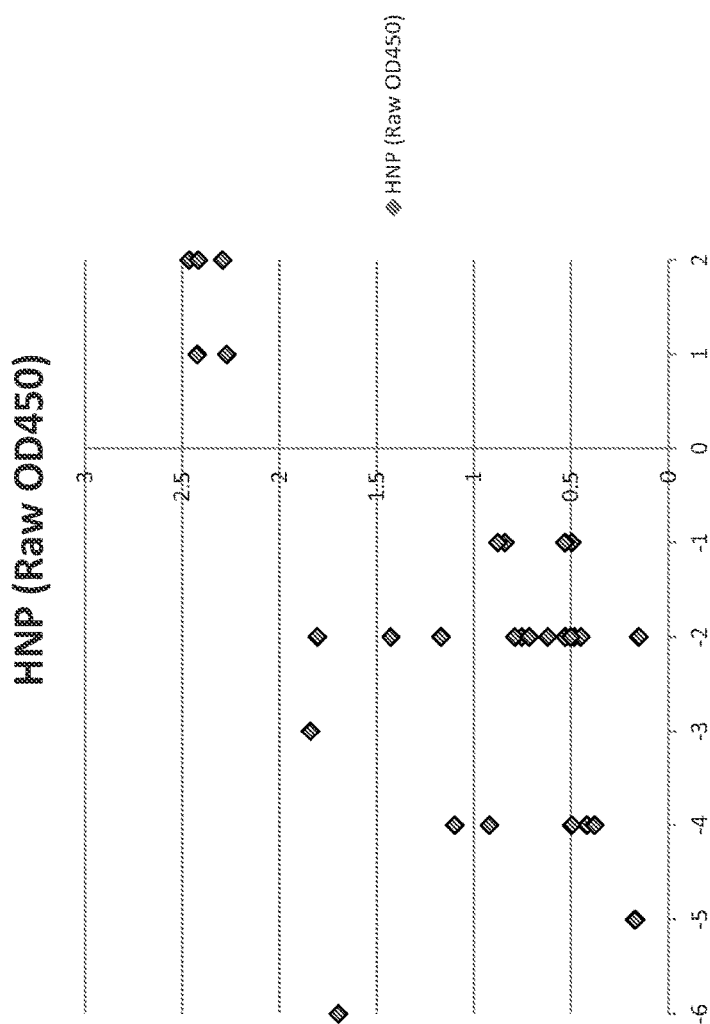
FIG. 12 is an image summarizing the clinical results of HNP1-3. From a clinical standpoint, HNP1-3 showed a clear separation between periprosthetic joint infection positive and negative samples.

From a clinical standpoint, HNP1-3 showed a clear separation between periprosthetic joint infection positive and negative samples (FIG. 12). These negative samples were sourced from multiple patient types and fluids, including serum, psuedogout, metal on metal (MOM), osteoarthritis (OA), and inflamed but not infected.

With separation between known periprosthetic joint infection positive and negative samples, including challenging negatives such as pseudogout and metal on metal, HNP1-3 is a clinically significant biomarker.

The next set of experiments was designed to use an accurate standard curve in order to interpolate dose concentrations and determine cutoff points via ROC analysis. For example, experiments were performed to seek an optimal dilution at which to run synovial fluid samples with the HYCULT® HNP1-3 Elisa kit.

The standard was reconstituted with 0.5 ml of di $H_2O$, yielding a stock concentration of 46 ng/ml (this value was stated on the certificate of analysis provided with this lot of kit). 150 ul of the reconstituted standard was diluted with 540 ul standard diluent to produce the first point in the standard curve, 10,000 pg/ml. The remaining points were then prepared using 1:2 dilutions in sample buffer.

Figure 13A:
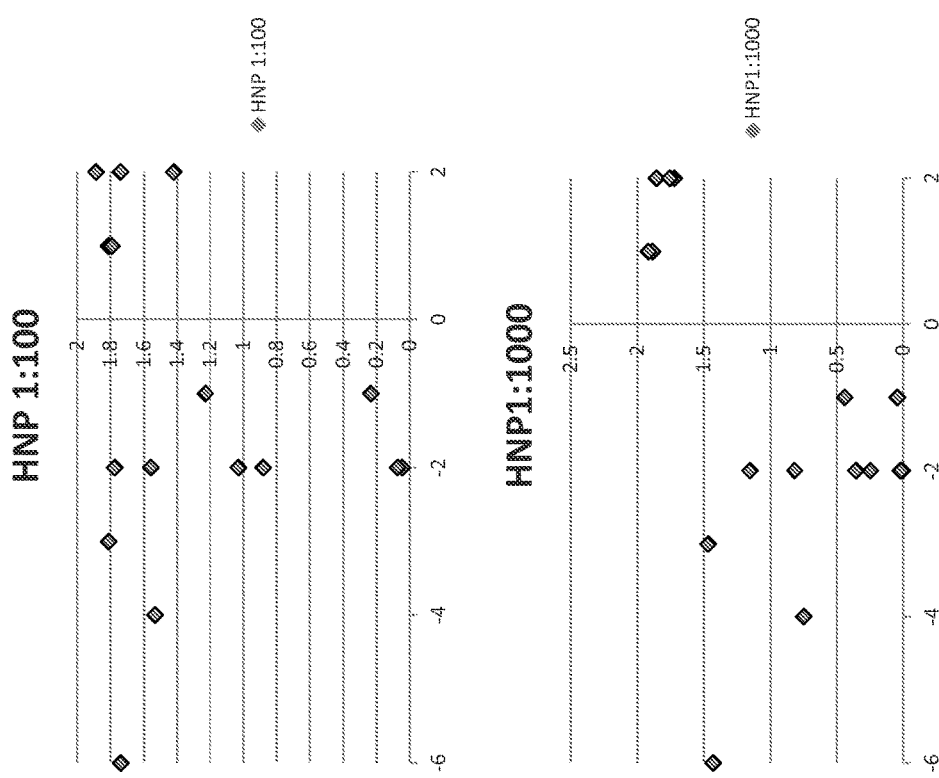
FIGS. 13A and 13B i& are images demonstrating that dilution has a significant effect on the clinical separation between periprosthetic joint infection positive and negative samples.
Figure 13B:
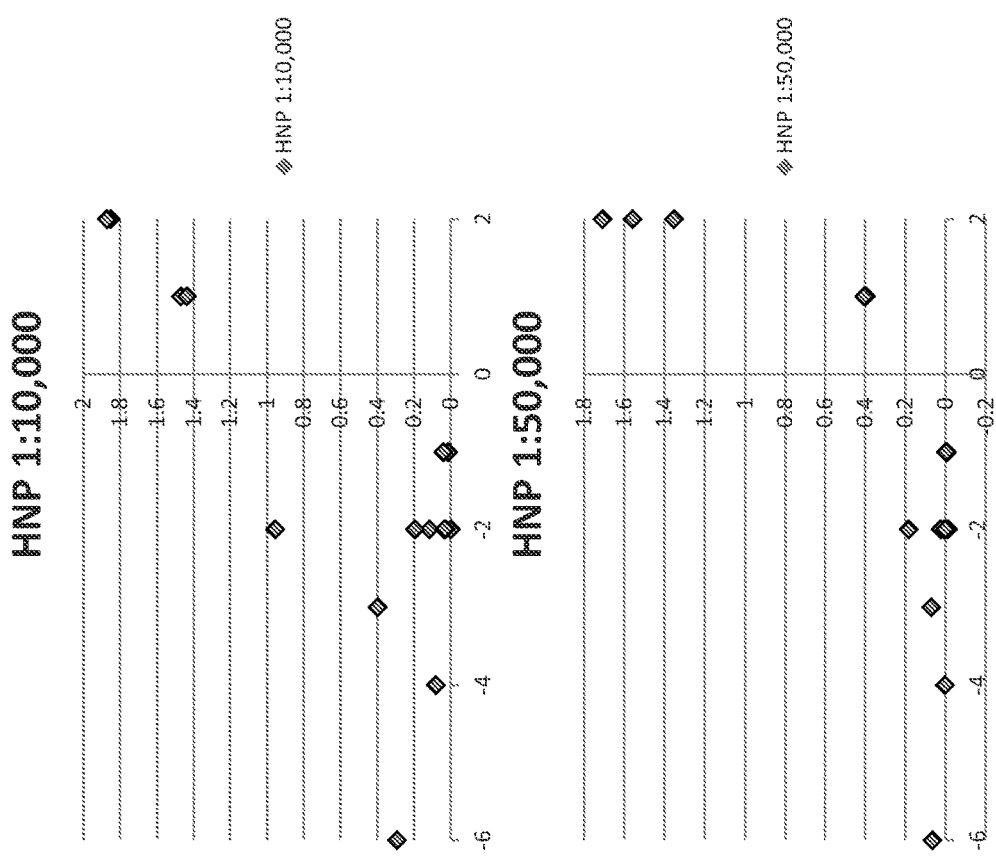

It was observed that dilution has a significant effect on the clinical separation between PJI positive and negative samples (FIG. 13). Dilution of 1:1000 seems insufficient, and for higher dilutions there are tradeoffs in separation, especially for challenging high-value negatives. The results demonstrate that dilution factors yield an optimal dilution at which positive and negative separation is maximized. Without wishing to be bound by any particular theory, it is believed that the desired dilution is between 5,000 and 10,000.

Example 4: HNP1-3 Clinical Study of Synovial Fluid

The commercially available Human HNP1-3 ELISA kit from HYCULT® Biotech was used for determining human HNP1-3 concentrations in synovial fluid. Experiments were performed to correlate HNP1-3 levels with the presence of Periprosthetic Joint Infection (PJI) in synovial fluid synovial fluid from human patients. The human HNP1-3 ELISA is a ready-to-use sandwich type, solid-phase, enzyme-linked immunosorbant assay. Samples, controls and standards were incubated in microplate wells coated with antibodies recognizing human HNP1-3. Biotinylated tracer antibodies provided with the kit bound to the captured human HNP1-3. Streptavidin-peroxidase conjugate then binds to the Biotinylated tracer antibody and reacted with the TMB substrate. The enzyme reaction was stopped by the addition of oxalic acid. The absorbance at 450 nm was measured by a spectrophotometer. Human HNP1-3 concentrations in synovial fluid samples were measured by plotting the absorbance of a standard curve versus the corresponding concentrations of the human HNP1-3 standards.

The materials and methods employed in the experiments disclosed herein are now described.

Materials and Methods

Clinical Sample

Based on the pilot studies regarding assessing the compatibility of the commercial kit with the synovial fluid matrix, a clinical assessment of 9 different synovial fluid sample patient cohorts were used for the clinical study (Table 10). 71 total synovial fluid samples from the in-house collection were tested in this study. The signal detection theory based on ROC curve was used to graphically represent the fraction of true positive rate vs. the false positive rate and to calculate the best cut-off value for diagnostic decision making.

TABLE 10

Sample Cohort Descriptions

| Category | Number of samples | Description | Classification |
|---|---|---|---|
| Pseudo gout | 2 | Challenging native group | −5 |
| Gout | 3 | Challenging native group | −4 |
| Mom | 1 | Challenging Joint group | −3 |
| OA | 15 | Challenging native group | −2 |
| Aseptic | 22 | Negative cohort | −1 |
| Infected-culture positive | 20 | Positive cohort | 1 |
| Infected-culture negative | 3 | Positive cohort | 2 |
| Equivocal infected | 3 | Positive samples that lack sufficient results to make an unambiguous classification as infected. For information only and not included in final analysis | 3 |
| Native-infected | 1 | Non-joint positive group | 4 |
| Total | 70 | | |

Storage Conditions Specified in Kit Manual

Upon receipt, individual components were stored at 2-8° C. (without freezing. Components beyond the expiration date printed on the kit label were not used. The standard, tracer and streptavidin-peroxidase were stable in lyophilized form until the expiration date indicated on the kit label, if stored at 2-8° C. The exact concentration of the standard was indicated on the label of the vial and the Certificate of Analysis. Once reconstituted, tracer and streptavidin-peroxidase were stable for 1 month if stored at 2-8° C. Once reconstituted, streptavidin-peroxidase can have a white blurred appearance. Once reconstituted, standard is stable for 1 month if stored at −20° C. Upon receipt, foil pouch around the plate was vacuum-sealed and un-punctured. Any unused strips were immediately returned to the foil pouch containing the desiccant pack and resealed along the entire edge of the zip-seal. Quality guaranteed for 1 month if stored at 2-8° C.

Sample Preparation

Synovial fluid samples were processed by centrifugation at 2,200 RPM for 10 minutes to remove cell debris and other contaminants. Samples are aliquoted and stored at −80° C. until used in assay. Samples were thawed to room temperature and mixed gently before assay was initiated. Samples were diluted in 1.5 ml polypropylene tubes using the dilution buffer supplied by HYCULT® kit HK317-02. The specified dilution was accomplished for each sample using a vortex to ensure dispersion of synovial fluid. Samples were not diluted according to product insert. Diluted samples were transferred to a round bottom polypropylene 96-well microplate in the order of the experimental plate layout.

Reagent Preparation

All reagents were equilibrated to room temperature prior to use. Wash buffer was prepared by mixing 20 ml of 40× wash buffer supplied with the HK317-02 kit and 780 ml of diH2O. Dilution buffer was prepared by mixing 20 ml of 10× dilution buffer with 180 ml of diH2O. No crystals were observed in the concentrated dilution buffer. Standard dilution buffer was prepared by mixing 10 ml of the 10× plasma diluent with 90 ml of the prepared dilution buffer. Standard solution was prepared by reconstituting lyophilized standard with 0.5 ml of diH20 to get a 46 ng/ml stock concentration. A standard curve was prepared in polypropylene tubes by a serial dilution of the reconstituted standard solution.

Tracer solution was prepared by reconstituting lyophilized Biotinylated tracer antibody with 1 ml of diH20. One part reconstituted tracer was diluted with 11 parts of dilution buffer.

Streptavidin-peroxidase solution was prepared by reconstituting the lyophilized conjugate with 1 ml of diH2O. Required volume of conjugate solution was prepared by diluting 1 part reconstituted conjugate with 23 parts of dilution buffer.

Standard Curve Preparation

Standard solution was prepared by reconstituting lyophilized standard with 0.5 ml of diH20 to get a 46 ng/ml stock concentration. Further dilutions were made using standard dilution buffer. A standard curve was prepared in polypropylene tubes using a 1:2 serial dilution of the reconstituted standard. The first standard dilution of the reconstituted standard was calculated to achieve a 10,000 pg/ml concentration.

Pilot Study and Clinical Study ELISA Protocol 100 ul in duplicate of standard, samples, and controls were transferred into appropriate wells, preferably without touching the side or bottom of the wells. The tray was covered and air bubbles were eliminated by tapping the tray without splashing the liquid onto the cover. The strips or plate were incubated for 1 hour at room temperature. Then the plates were washed with wash buffer. After washing, 100 ul of diluted tracer was added to each well with an incubation time of 1 hour at room temperature. The plates are then washed to remove the tracer solution. After washing, 100 ul of diluted streptavidin-peroxidase was added to each well with an incubation time of 1 hour at room temperature. After the incubation time, streptavidin-peroxidase was removed by washing the plates following by the addition of 100 ul of TMB substrate to each well with an incubation time of 15 minutes at room temperature (avoiding exposing the micro well strips to direct sunlight). The reaction was stopped by adding 100 ul of stop solution and the plate was read within 30 minutes after addition of stop solution at 450 nm using a plate reader, following the instructions provided by the instrument's manufacturer.

The results of the experiments presented in this Example are now described.

Human neutrophil alpha-defensins (also called Human Neutrophil Peptides, HNP) belong to the family of cationic trisulfide-containing microbicidal peptides. There are three highly homologous human defensins stored in azurophilic granules of polymorphonuclear leukocytes, HNP 1-3. They account for about 5% of total PMN protein and comprise about 99% of the total defensin content of the neutrophils with traces of HNP-4. HNP-1, HNP-2 and HNP-3 are encoded by two genes DEFA1 and DEFA3 localized to chromosome 8. DEFA1 and DEFA3 encode identical peptides except the conversion of the first amino acid from alanine in HNP-1 to aspartic acid in HNP-3; HNP-2 represent N-terminally truncated iso-form lacking the first amino acid.

Figure 14:
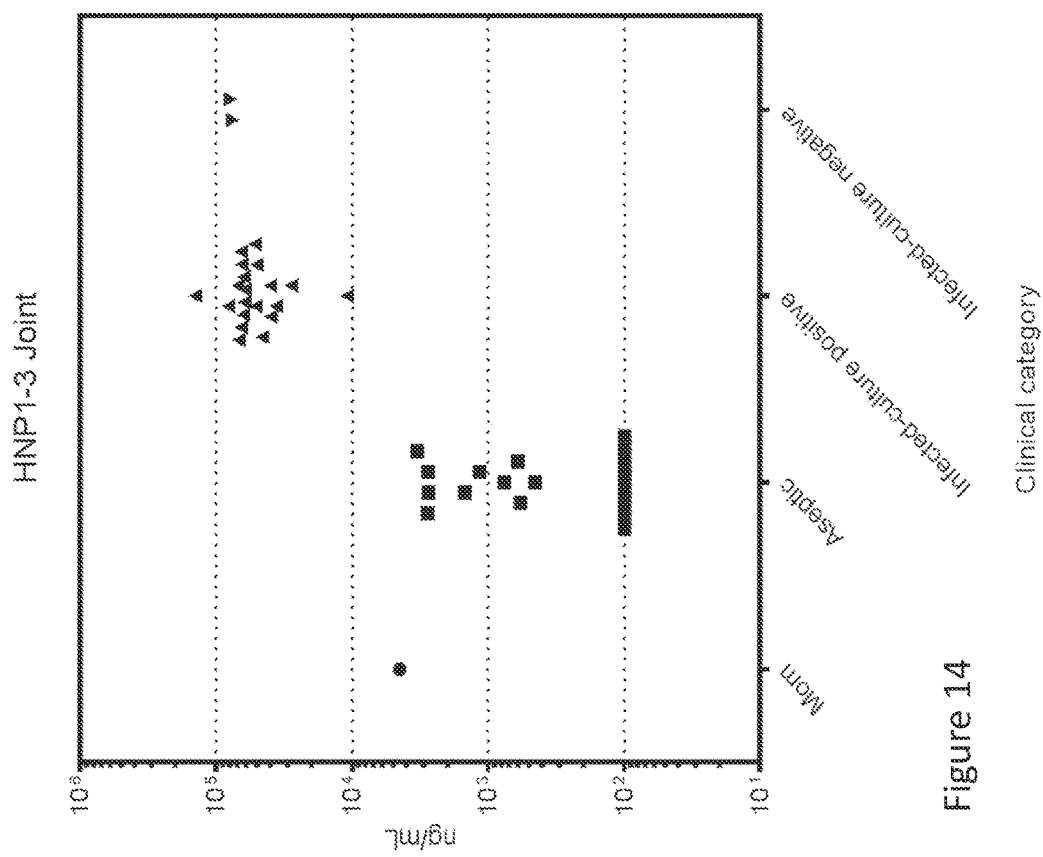
FIG. 14 is an image of a clinical plot showing that HNP1-3 is a biomarker for periprosthetic joint infection in synovial fluid from joint samples.
Figure 15:
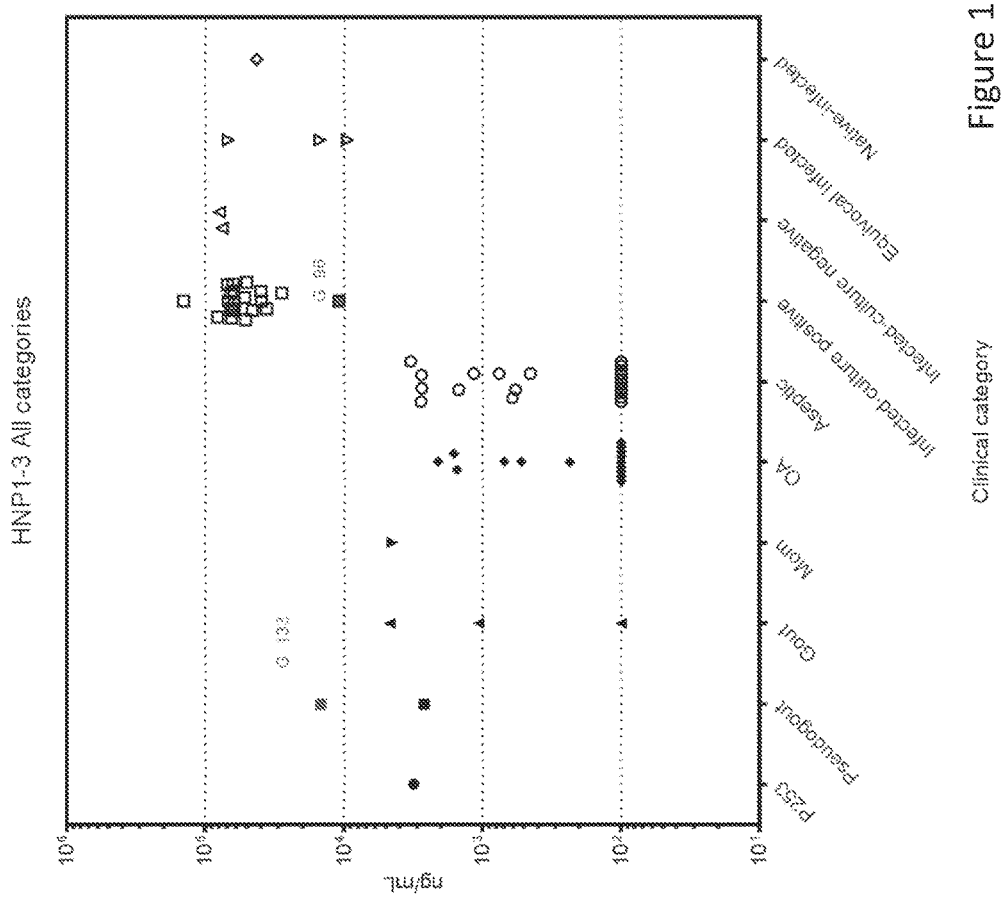
FIG. 15 is an image showing the results from samples tested including synovial fluid from native joints with respect to the presence of HNP1-3 in the samples.

Activation of neutrophils leads to rapid release of HNP. HNP can be measured in plasma during infection and inflammation. Micromolar concentrations of HNP are described in septic blood, while in normal plasma very low levels of HNP are present. The results presented herein correlate high HNP levels with septic synovial fluid. HNP1-3 was found to be a desired biomarker for use in diagnosing periprosthetic joint infection. The ROC analysis of the data derived a cut-off at 7720 ng/ml. The results demonstrate an AUC of 1.0 with 100% specificity and 100% sensitivity with prosthetic joint samples (Table 11). FIG. 14 demonstrates a clinical plot showing that HNP1-3 can be a biomarker for periprosthetic joint infection in synovial fluid from joint samples. FIG. 15 shows the results from samples tested including synovial fluid from native joints.

TABLE 11

Assay performance data

| Biomarker | AUC | Cut-off (derived by ROC analysis on joint samples) | Specificity Joint | Sensitivity Joint | Specificity ALL | Sensitivity ALL |
|---|---|---|---|---|---|---|
| HNP1-3 | 1.000 | 7720 ng/mL | 100.0 | 100.0 | 97.67 | 100.0 |

Example 5: BPI Clinical Study of Synovial Fluid

The commercially available Human BPI ELISA kit from HYCULT® Biotech was used for determining human BPI concentrations in synovial fluid. Experiments were performed to correlate BPI levels with the presence of Periprosthetic Joint Infection (PJI) in synovial fluid synovial fluid from human patients. The human BPI ELISA is a ready-to-use sandwich type, solid-phase, enzyme-linked immunosorbant assay. Samples, controls and standards were incubated in microplate wells coated with antibodies recognizing human BPI. Biotinylated tracer antibodies provided with the kit bound to the captured human BPI. Streptavidin-peroxidase conjugate bound to the Biotinylated tracer antibody and was able to react with the TMB substrate. The enzyme reaction was stopped by the addition of oxalic acid. The absorbance at 450 nm was measured by a spectrophotometer. Human BPI concentrations in synovial fluid samples were measured by plotting the absorbance of a standard curve versus the corresponding concentrations of the human BPI standards.

The materials and methods employed in the experiments disclosed herein are now described.

Materials and Methods
Clinical Sample

Based on the pilot studies regarding assessing the compatibility of the commercial kit with the synovial fluid matrix, a clinical assessment of 9 different synovial fluid sample patient cohorts were used for the clinical study (Table 10). 71 total synovial fluid samples from the in-house collection were tested in this study. The signal detection theory based on ROC curve was used to graphically represent the fraction of true positive rate vs. the false positive rate and to calculate the best cut-off value for diagnostic decision making.

111 different synovial fluid samples from the in-house synovial fluid collection were evaluated. This study was designed to run ELISAs for HNP1-3 and Ela2 alongside BPI in order to expand on the HNP1-3 clinical study discussed elsewhere herein with more samples. There were 51 classified synovial fluid samples tested in this experiment that were also tested in a previous clinical study in order to compare ROC analysis of biomarkers. The signal detection theory based on ROC curve was used to graphically represent the fraction of true positive rate vs. the false positive rate and to calculate the best cut-off value for diagnostic decision making.

TABLE 12

Sample Cohort Descriptions

| Category | Number of samples | Description | Classification |
|---|---|---|---|
| Unclassified | 55 | Insufficient data accompanied with sample to classify | −7 |
| Pseudo gout | 3 | Challenging native group | −5 |
| Gout | 0 | Challenging native group | −4 |
| Mom | 1 | Challenging Joint group | −3 |
| OA | 3 | Challenging native group | −2 |
| Aseptic | 24 | Negative cohort | −1 |
| Infected-culture positive | 15 | Positive cohort | 1 |
| Infected-culture negative | 1 | Positive cohort | 2 |
| Equivocal infected | 8 | Positive samples that lack sufficient results to make an unambiguous classification as infected. For information only and not included in final analysis | 3 |
| Native-infected | 1 | Non-joint positive group | 4 |
| Total | 111 | | |

Reagent Preparation

All reagents were equilibrated to room temperature prior to use. Wash/dilution buffer B was prepared by mixing 20 ml of the 40× wash/dilution buffer A supplied with the HK314-02 kit with 380 ml of diH2O. Alternatively, Wash/dilution buffer B was prepared by mixing 40 ml of 20× wash/dilution buffer B with 360 ml of diH2O. Final wash/dilution buffer was prepared by mixing buffer A and buffer B together.

Standard solution was prepared by reconstituting lyophilized standard with 0.5 ml of diH20 to get a 219 ng/ml stock concentration. A standard curve was prepared in polypropylene tubes by a serial dilution of the reconstituted standard solution.

Tracer solution was prepared by reconstituting lyophilized Biotinylated tracer antibody with 1 ml of diH20. 1 part reconstituted tracer was diluted with 11 parts of dilution buffer.

Streptavidin-peroxidase solution was prepared by reconstituting the lyophilized conjugate with 1 ml of diH2O. Required volume of conjugate solution was prepared by diluting 1 part reconstituted conjugate with 23 parts of dilution buffer.

Standard Curve Preparation

Standard solution was prepared by reconstituting lyophilized standard with 0.5 ml of diH20 to get a 219 ng/ml stock concentration. Further dilutions were made using wash/dilution buffer.

A standard curve was prepared in polypropylene tubes using a 1:2.5 serial dilution of the reconstituted standard.

The first standard dilution of the reconstituted standard was calculated to achieve a 25,000 pg/ml concentration.

The results of the experiments presented in this Example are now described.

The antimicrobial protein BPI (Bacterial Permeability Increasing protein) is a 55 kDa protein found in the primary azurophilic granules of human neutrophils and has also been detected on the surface of neutrophils, small intestinal and oral epithelial cells. BPI is a bactericidal compound that is present in polymorphonuclear cells and in lower levels in the specific granules of eosinophils. BPI possesses high affinity toward the lipid A region of lipopolysaccharides (LPS) that comprise the outer leaflet of the gram-negative bacterial outer membrane. Binding of BPI to the lipid A moiety of LPS exerts multiple anti-infective activities against gram-negative bacteria: 1) cytotoxicity via sequential damage to bacterial outer and inner lipid membranes, 2) neutralization of gram-negative bacterial LPS, 3) opsonization of bacteria to enhance phagocytosis by neutrophils. Airway epithelial cells constitutively express the BPI gene and produce the BPI protein and, therefore, BPI may be a critical determinant in the development of LPS-triggered airway disease. Inflammation induced by LPS possibly contributes to the development of rapid airflow decline, a serious and often fatal complication of hematopoietic cell transplantation. In plasma of healthy individuals BPI is present at levels of <0.5 ng/ml, which increases approximately 10-fold during acute phase responses.

Figure 16:
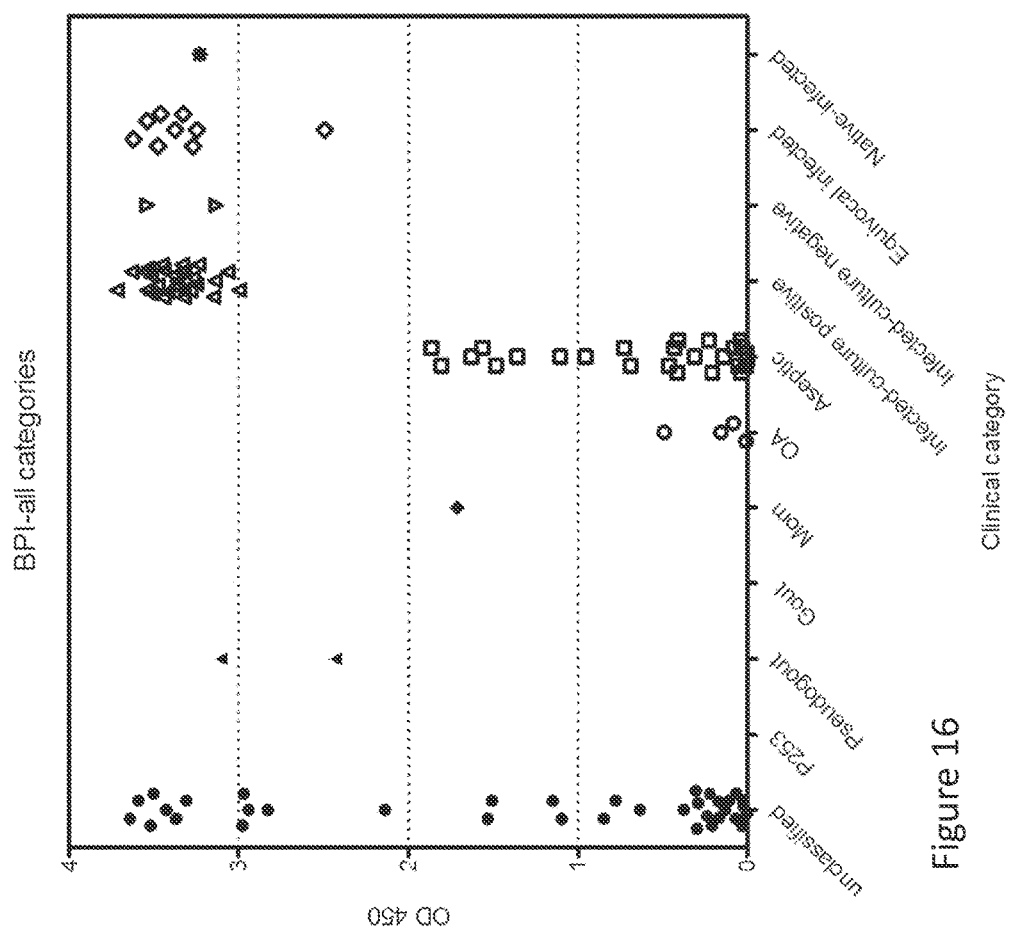
FIG. 16 is an image of a clinical plot showing that BPI is a biomarker for periprosthetic joint infection in synovial fluid from joint samples.
Figure 17:
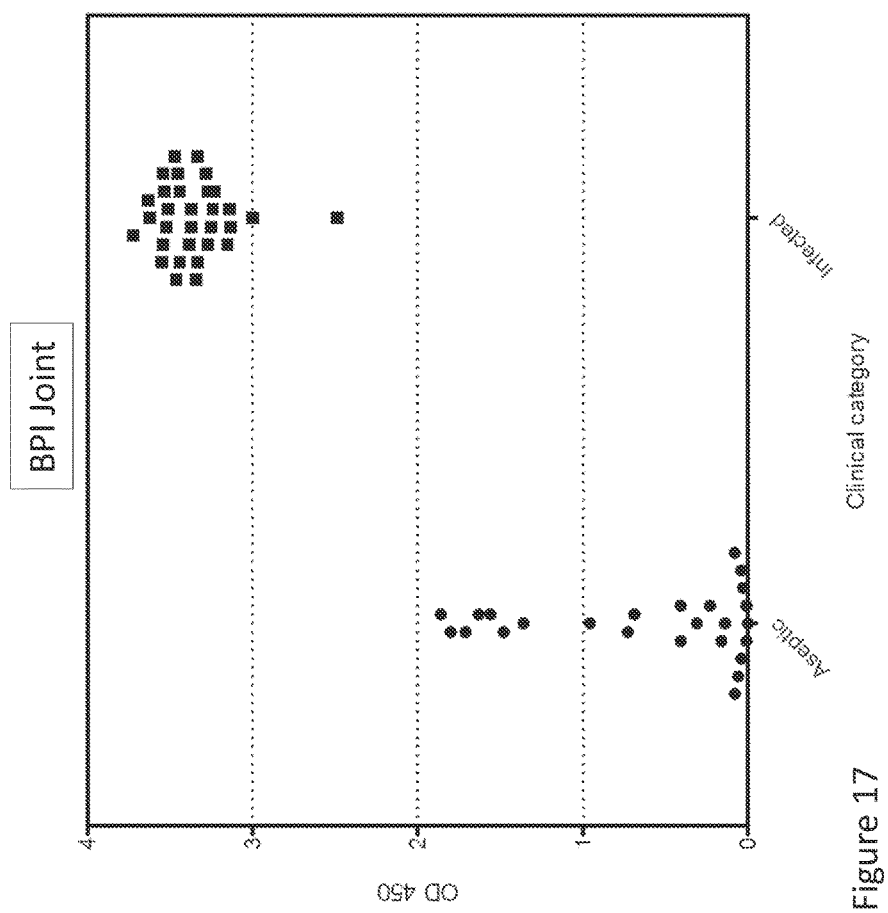
FIG. 17 is an image demonstrating that BPI is a biomarker for periprosthetic joint infection in synovial fluid from joint samples.

The results presented herein demonstrate elevated BPI concentrations in infected synovial fluid samples. For the ROC analysis, a background subtracted signal was used to derive a cut-off of 2.18 O.D. The analysis showed an AUC of 1.0 with 100% specificity and 100% sensitivity with prosthetic joint samples (Table 13). FIGS. 16 and 17 demonstrate clinical plots showing that BPI is a biomarker for periprosthetic joint infection in synovial fluid from joint samples.

TABLE 13

Assay performance data

| Biomarker | AUC | Cut-off (derived by ROC analysis using background subtracted data) | Specificity Joint | Sensitivity Joint |
|---|---|---|---|---|
| BPI | 1.0 | 2.18 O.D. | 100 | 100 |

Example 6: Sepsis Panel Clinical Screen

The following experiments were performed to identify potential biomarkers for periprosthetic joint infection. The entire MILLIPORE® Sepsis Panel III was used to screen an expanded cohort of samples to establish a clinical data set that can be used for ROC and other cutoff analysis.

Briefly, MILLIPORE® Sepsis Panel 3 (HSP3MAG-63k) was used to source all materials for this experiment. After allowing the kit contents to reach room temperature, the magnetic beads were prepared. Each individual bead vial was sonicated for 30 seconds, than vortexed for 1 minute. 150 ul of each bead solution was combined in the bead mixing vial, and the mixture was brought to a total volume of 3.0 ml using the bead diluent.

The standard was reconstituted with 250 ul of diH2O and allowed to sit for 15 minutes at room temperature. Standards were then prepared using a 6-step 1:4 serial dilution, using the assay buffer as a diluent.

Selected synovial fluid samples were then diluted 1:1,000 in assay buffer. 50 ul of assay buffer was added to each well on the assay plate, and then 25 ul/well of sample or standard was added as appropriate. 25 ul/well of thoroughly vortexed bead mixture was then added. The plate was sealed and incubated for 2 hours at 25* at shake setting 5 on the JITTERBUG™ plate shaker.

The plate was washed using the standard LUMINEX® wash protocol (DPBS w/0.05% Tween as wash buffer, BIOTEK® automated washer for all steps: 1 minute incubation on magnet, aspiration and dispense of wash buffer, 30 seconds shaking on the JITTERBUG™, repeated 3×). 25 ul/well of detection antibody cocktail was then added to the plate. After one hour of incubation at 25* at shake setting 5 on the JITTERBUG™ plate shaker, 25 ul/well of Strep-PE detection molecule was added to each well. The plate was incubated for 30 min at 25* at shake setting 5 on the JITTERBUG™ plate shaker.

The full wash protocol was run, then 150 ul/well of MILLIPORE® 1x wash buffer was added. The plate was agitated for 10 minutes to fully resuspend beads, then read on the LX200 unit utilizing BIO-PLEX® software.

The results demonstrate that Elastase 2, Resistin, NGAL, thrombospondin, and Lactoferrin are biomarkers for periprosthetic joint infection.

Example 7: Biomarkers for Joint Infection

Using an established sample bank of synovial fluid that included some problematic samples, experiments were designed to further evaluate additional biomarkers. The series of markers include IL-1β, IL-6, IL-8, TNFα, G-CSF, IL-1a, VEGF, IP-10, BFGF (aka FGF2), CRP, a2M, SKALP, FINE Enzyme assay, LE Strip, Lactoferrin, Lipocalin-2/NGAL, Neutrophil Elastase-2 (ELA2), Resistin, Thrombospondin-1 (TSP-1), HNP1-3, and BPI. Each marker was evaluated with a limited set of positive and negative samples and evaluated with a larger cohort (Table 10) if there was good separation between the samples. The overall assay performance is listed in Table 14.

TABLE 14

ROC analysis

| Biomarker | AUC | Cut-off (derived by ROC analysis on joint samples) | Cut-off Range (same unit as cutoff) | Specificity Joint | Sensitivity Joint | Specificity ALL | Sensitivity ALL |
|---|---|---|---|---|---|---|---|
| HNP1-3 | 1.000 | 7720 ng/mL | 3334-10946 | 100.0 | 100.0 | 97.67 | 100.0 |
| ELA-2 | 1.000 | 942 ng/mL | 721-19000 | 100.0 | 100.0 | 97.67 | 100.0 |
| NGAL | 0.998 | 1,644 ng/mL | 1100-3200 | 95.65 | 100.0 | 93.02 | 100.0 |
| Resistin | 0.996 | 82.9 ng/mL | 53-112 | 95.65 | 100.0 | 93.02 | 100.0 |

TABLE 14-continued

ROC analysis

| Biomarker | AUC | Cut-off (derived by ROC analysis on joint samples) | Cut-off Range (same unit as cutoff) | Specificity Joint | Sensitivity Joint | Specificity ALL | Sensitivity ALL |
|---|---|---|---|---|---|---|---|
| Thrombospondin | 0.996 | 136 ng/mL | 131-141 | 95.65 | 100.0 | 92.86 | 100.0 |
| Lactoferrin | 0.996 | 2,993 ng/mL | 1200-4700 | 95.65 | 100.0 | 93.02 | 100.0 |
| IL-1β (MSD) | 0.991 | 33.25 pg/mL | 30-35 | 95.65 | 100.0 | 97.67 | 100.0 |
| IL-8 (MSD) | 0.989 | 6794 pg/ml | 6725-6860 | 95.65 | 100.0 | 97.67 | 100.0 |
| CRP | 0.975 | 11412 ng/mL | 11000-12000 | 95.65 | 91.30 | 93.02 | 91.67 |
| TNFα (MSD) | 0.960 | 66.42 pg/mL | 65-88 | 100.0 | 82.61 | | |
| IL-6 (MSD) | 0.940 | 3472 pg/mL | 1965-5000 | 95.65 | 91.30 | | |
| HNE | 0.926 | 552.8 ng/mL | 521-584 | 100.0 | 95.45 | 97.67 | 95.65 |
| a2M | 0.855 | 73.45 pg/mL | 70-76 | 78.26 | 77.27 | 72.09 | 78.3 |
| VEGF | 0.851 | 2565 pg/mL | 2500-3300 | 82.61 | 78.26 | | |
| FGF2 | 0.785 | 2.25 pg/mL | 1-12 | 95.65 | 65.22 | | |
| G-CSF | 0.712 | 94.35 pg/mL | 74-100 | 73.91 | 73.91 | | |
| SKALP | 0.675 | 3721 pg/mL | 2100-3800 | 84.21 | 52.94 | | |
| IP-10 | 0.582 | 5003 pg/mL | 4500-5800 | 78.26 | 56.52 | | |
| LBP | | | | | | | |
| Orsomucoid | | | | | | | |

Example 8: Detection of Hyaluronic Acid in Synovial Fluid

Hyaluronic acid (HA) is a large carbohydrate polymer that is a major component of synovial fluid. HA increases the viscosity of the synovial fluid and thereby increases its quality as a lubricant. While HA is found in a variety of tissues (including connective, epithelial, and neural), the concentration of hyaluronic acid is greatly increased in synovial fluid relative to other tissues, including serum. As such, the quantitation of HA in biological samples could serve as a means to distinguish synovial fluid from contaminating serum.

A series of human synovial fluid (from an internal collection) and serum samples (purchased from Bioreclamation) were probed for the presence of HA using a QUANTIKINE® ELISA kit produced by R&D Systems (cat# DHYAL0).

Figure 18:
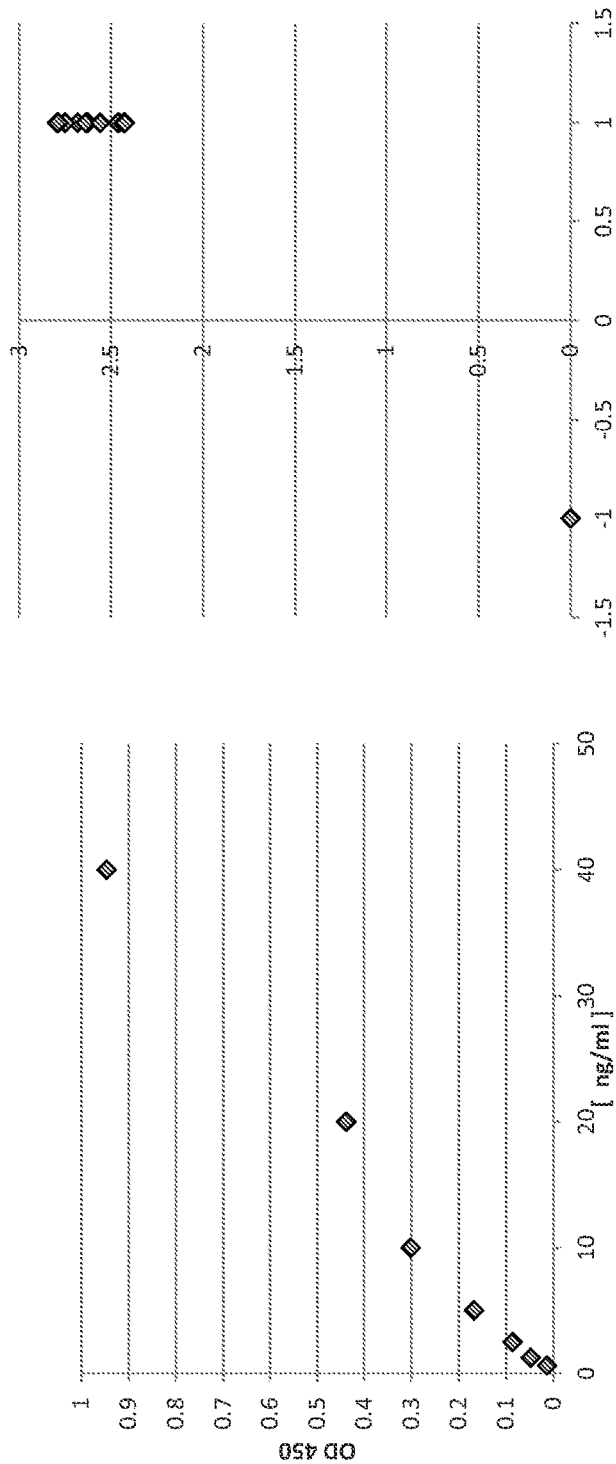
FIG. 18 is an image showing the measure of HA for serum versus synovial fluid. In the right panel, (−1) denotes serum, (1) denotes synovial fluid.

The results presented herein demonstrate that when diluted 1:10 or 1:100, synovial fluid samples produce an OD signal that was well above the signal generated by the 40 ng/mL standard, the highest standard recommended by the R&D protocol. As these levels were at the maximum absorbance at 450 nm, synovial fluid sample could not be differentiated form one another for the concentration of HA, unlike the serum samples, where some variation could be observed. Nonetheless, there was a clear separation in the signal generated by serum or synovial fluid sample (FIG. 18). FIG. 18 depicts a representative standard curve from (left) and a comparison of OD450 signal for synovial and serum samples (right; −1 indicated a serum sample, 1 a synovial fluid sample).

Next, synovial fluid samples were diluted well beyond 1:100. Even at 1:100,000, raw signal for synovial samples were detectable above background, though a 1:50,000 dilution was adequate to bring the samples into range. Synovial fluid samples were found to have HA concentrations ranging from 0.529 ug/ml to 2.575 ug/ml. Even at a 1:1,000 dilution, HA levels in serum were not detectable. For both a "high" and "low" SF sample, dilution with serum produces equal and expected changes in the concentration of HA.

The results presented herein demonstrate that HA is a valid marker for distinguishing synovial fluid from serum. In some instances, the sensitivity of this assay prefers that synovial fluid be diluted 1:50,000 any yet still allows for very clear detection of whether or not any synovial fluid is present in a sample.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of treating joint pain in a subject, the method comprising;
    applying a fluid sample obtained from the joint to a system comprising a device, cartridge or strip having a flow path through which a fluid sample can move, the flow path comprising:
    a) a first region comprising a first detection reagent that specifically binds a human neutrophil α-defensin; and
    b) a second region comprising an internal control detector reagent; and
    treating the subject with an anti-bacterial agent if greater than 5,000 ng/ml of human neutrophil α-defensin is detected in the fluid sample, or treating the subject for aseptic-inflammation if less than 5,000 ng/ml of human neutrophil α-defensin is detected in the fluid sample.

2. The method of claim 1, wherein the joint is a replacement joint or a prosthetic joint.

3. The method of claim 1, wherein the internal control detector reagent specifically binds hyaluronic acid, mucopolysaccharide, glucosamine, chondroitin sulfate, cartilage oligomeric matrix protein, lumican, lubricin, or a combination thereof.

4. The method of claim 1, wherein the α-defensin in the fluid sample is detected at a concentration that is at least about twice the concentration of the α-defensin in a synovial fluid sample from a normal joint.

5. The method of claim 1, wherein the first detection reagent detects the α-defensin at a concentration that is at least about 7,000 ng/ml.

6. The method of claim 1, wherein the flow path further comprises a second detection reagent that specifically binds a second biomarker of joint infection.

7. The method of claim 1, further comprising:
   mixing the fluid sample obtained from the joint with an assay buffer; and
   applying the fluid sample and assay buffer mixture to the system.

8. The method of claim 7, wherein the assay buffer dilutes the fluid sample to enhance the ability to pipette and transfer the fluid sample.

9. The method of claim 7, wherein the assay buffer comprises a reagent that lyses cellular components present in the fluid sample.

10. The method of claim 9, wherein the reagent is a non-ionic surfactant.

11. The method of claim 7, wherein the assay buffer comprises a reagent that preserves the fluid sample and stabilizes biomarkers present in the fluid sample.

12. The method of claim 7, wherein the assay buffer comprises a reagent that inhibits an interfering component present in the fluid sample.

13. The method of claim 7, wherein the assay buffer maintains a pH in the range of about 6-8.

14. The method of claim 7, wherein with the assay buffer dilutes the fluid sample by a factor of between about 5,000 and about 10,000.

\* \* \* \* \*